(12) United States Patent
Mushegian et al.

(10) Patent No.: US 9,102,750 B2
(45) Date of Patent: *Aug. 11, 2015

(54) BRANCHIOSTOMA DERIVED FLUORESCENT PROTEINS

(71) Applicant: Stowers Institute for Medical Research, Kansas City, MO (US)

(72) Inventors: Arcady Mushegian, Leawood, KS (US); Congrong Yu, Leawood, KS (US); Joel Schwartz, Overland Park, KS (US); Limei Ma, Leawood, KS (US)

(73) Assignee: Stowers Institute for Medical Research, Kansas City, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/171,932

(22) Filed: Feb. 4, 2014

(65) Prior Publication Data

US 2014/0220629 A1 Aug. 7, 2014

Related U.S. Application Data

(62) Division of application No. 12/311,076, filed as application No. PCT/US2007/079333 on Sep. 24, 2007, now Pat. No. 8,680,235.

(60) Provisional application No. 60/826,735, filed on Sep. 22, 2006, provisional application No. 60/891,886, filed on Feb. 27, 2007.

(51) Int. Cl.
*C07K 14/435* (2006.01)

(52) U.S. Cl.
CPC .............................. *C07K 14/43504* (2013.01)

(58) Field of Classification Search
None
See application file for complete search history.

(56) References Cited

U.S. PATENT DOCUMENTS

| | | | | |
|---|---|---|---|---|
| 8,609,393 | B2 * | 12/2013 | Israelsson | 435/252.3 |
| 8,680,235 | B2 * | 3/2014 | Mushegian et al. | 530/350 |
| 2009/0286314 | A1 * | 11/2009 | Israelsson | 435/348 |
| 2010/0168396 | A1 * | 7/2010 | Mushegian et al. | 530/387.9 |
| 2014/0011272 | A1 * | 1/2014 | Israelsson | 435/348 |
| 2014/0220629 | A1 * | 8/2014 | Mushegian et al. | 435/69.1 |

FOREIGN PATENT DOCUMENTS

| | | | |
|---|---|---|---|
| CN | 1982456 | * | 6/2007 |
| EP | 2021362 A1 | * | 2/2009 |
| WO | WO 2007/142852 A1 | * | 12/2007 |
| WO | WO 2008/094316 A2 | * | 8/2008 |

OTHER PUBLICATIONS

Baumann et al, Biology Direct 2008, 3:28 12 pages.*
Deheyne et al, Biol. Bull., 2007, 213/2:95-100.*
Yu et al, Nature, 2007, 445(7128):613-617.*

* cited by examiner

*Primary Examiner* — Nita M Minnifield
(74) *Attorney, Agent, or Firm* — Bryan Cave LLP

(57) ABSTRACT

The present invention provides compositions, combinations, methods, sequences and kits for use of novel fluorescent proteins derived from the genus *Branchiostoma*. Specifically, polynucleotide and polypeptide sequences encoding fluorescent proteins isolated from *Branchiostoma floridae*, including harmonized sequences, which permit enhanced expression of the encoded polypeptides in mammalian cells in vivo are provided.

10 Claims, 32 Drawing Sheets

FIG. 1

```
Seq. ID No. 25   -----atgcctctgccgcaaccacatccaccttcacgctccat      44
Seq. ID No. 22   aagcttatgcctctgccgcaaccacatccaccacctgcacggcagcat   50

Seq. ID No. 25   caacggccacgagttgacattgacaggaggaaaagcgaccgaacg       94
Seq. ID No. 22   caacggccacgagttgacattgacaggcggcaaggcgacccaacg      100

Seq. ID No. 25   ccggctcgctggtgaccacagcgaaatccaccaaggtgccctgaagttc  144
Seq. ID No. 22   ccggcagcttgaccacagcgaagagagccaaggcaccaaggcccctgaagttc  150

Seq. ID No. 25   tctccctacttgatgatccccacctcggtacggtactaccagtacct    194
Seq. ID No. 22   agccctacttgatgatccccacctgggctggcttactaccagtacct    200

Seq. ID No. 25   ccctacccgaccggaccctgccgcttccagcctccatgttcagaagat   244
Seq. ID No. 22   gccctaccgacacgaccggacccccttccagccagcatgctgaggccac  250

Seq. ID No. 25   cgggtatgcagtcaccgctgttcgacttgaagacgagcaagctg       294
Seq. ID No. 22   gcggctacgccgtgtacaggtacagcttcgactcgaggaccgcaagctg  300
```

FIG. 1 (CONT.)

| | |
|---|---|
| Seq. ID No. 25 | actaccgagtttaagtactcctacgaggttccatatcaagccgacat 344 |
| Seq. ID No. 22 | accaccgagttcaagtacagctacgaggcacatcaagccgacat 350 |
| Seq. ID No. 25 | gaagctgatggaagcggttccctgacgacggcccagtcatgaccagcc 394 |
| Seq. ID No. 22 | gaagctgatggcacggccttcccgacgacggcccctgatgaccagcc 400 |
| Seq. ID No. 25 | agattgtcgaccaggggctgcggtccaagaagacgtatcttaacaac 444 |
| Seq. ID No. 22 | agatcgtgaccaggggctgcggtgagcaagaagacctgaacaac 450 |
| Seq. ID No. 25 | aaccatcgtcgaccgtgacttcgactgagttacaacctgcagaatgggaa 494 |
| Seq. ID No. 22 | aaccatcgtgaccgtgacttcgactgagctacaacctgcagacggcaa 500 |
| Seq. ID No. 25 | gcgctacaggcccgagtgtcgagccactacatcttcgacaagccttt 544 |
| Seq. ID No. 22 | gaggtacaggccaggtgagcagccactacatcttcgacaagccttca 550 |
| Seq. ID No. 25 | cagccgatctcatcaagaagagccgtcttcgtgtaccgsaagtgccac 594 |
| Seq. ID No. 22 | gccgacctgatgaagaagaagcccgtgttcgtgtacagggaagtgccac 600 |
| Seq. ID No. 25 | gtgaaggcttccaagaaccgaagtcacctggagaggagaaggcgtt 644 |
| Seq. ID No. 22 | gtgaaggccagcaagaaccgagtgacctggagaggagaaggccttc 650 |

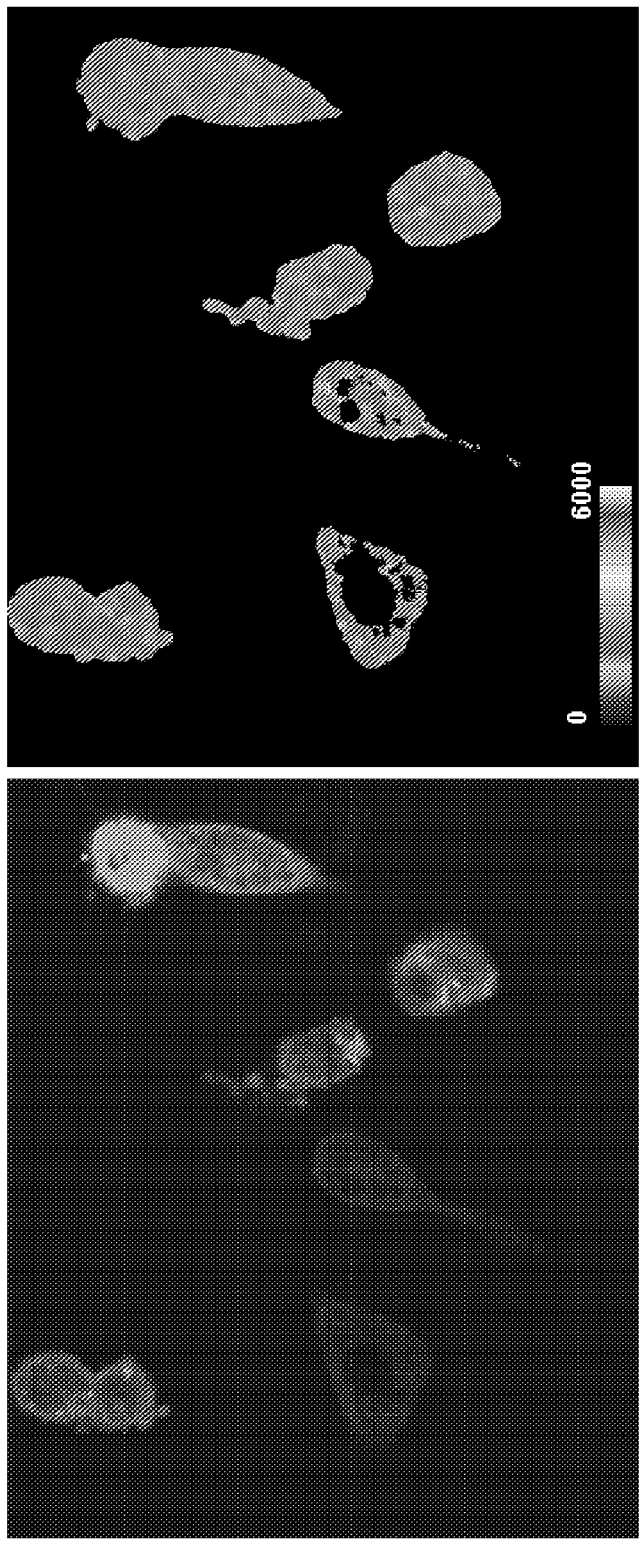

FIG. 21

```
SEQ ID NO: 4   ----------------MSKGEELFTGIVPVLIELDGDVHGHKFSVRGEGEGDADYGKLELKFICTTGK-LPVPWPTLVTTLGYG--IQCFARYPEHMKMNDFFKS
SEQ ID NO: 5   ----------------MEGGPALFQSDMTFKIFIDGEVNGQKFTIVADGSSKFPHGDFNVHAVCETGK-LPMSWKPICHLIQYG--EPFFARYPDGIS--HFAQE
SEQ ID NO: 6   ----------MSAIKPDMKINLRMEGNVNGHHFVIDGDGTGKPFEGKQSMDLEVKEGGPLPFAFDILTTAFHYG--NRVFAEYPDHIQ--DYFKQ
SEQ ID NO: 7   ----------GGAIKPDMKINLRMEGNVNGHHFVIDGDGTGKPFEGKQSMDLEVKEGGPLPFAFDILTTAXHYG--NRVFAEYPDHIQ--DYFKQ
SEQ ID NO: 8   ----------MSVIKSDMKIKLRMEGTVNGHKFVIEGEGEGKPYEGTQTMNLKVKEGAPLPFAYDILTTAFQYG--NRVFTKYPKDIP--DYFKQ
SEQ ID NO: 9   ----------MSVIKSDMKIKLRMEGTVNGHKFVIEGEGEGKPYEGTQSMDLTVKEGAPLPFAYDILTTVFHYG--NRVFAKYPKDIP--DYFKQ
SEQ ID NO:10   ----------MSVIKSVMKIKLRMEGAVNGHNFVIVGEGEGKPYEGTQSMDLTVKEGAPLPFAYDILTTVFHYG--NRVFAKYPKDIP--DYFKQ
SEQ ID NO:11   ----------MSVIKPEMKIKLCMRGTVNGHNFVIEGEGKGNPYEGTQILDLNVTEGAPLPFAYDILTTVFQYG--NRAFTKYPADIQ--DYFKQ
SEQ ID NO:12   ----------MSVIKSVMKIKLRMDGIVNGHKFVITGEGEGKPFEGTHTIILKVKEGGPLPFAYDILTTAFQYG--NRVFTKYPKDIP--DYFKQ
SEQ ID NO:13   ----------MSALKEEMKINLTMEGVVNGLPFKIRGDGKGKPYQGSQELTLTVVKGGPLPFSVDILTTMFQYG--NRAFVNYPEDIP--DIFKQ
SEQ ID NO:14   ----------MSVIATQMTYKYYMSGTVNGHYFEVEGDGKGKPYEGEQTVRLTVTKGGPLPFAWDILSPQSQYG--SIPFTKYPEDIP--DVVKQ
SEQ ID NO:15   ----------MVSKGEENNMAIIKEFMRFKVRMEGSVNGHEFEIEGEGEGRPYEGFQTAKLKVTKGGPLPFAWDILSPQFTYG--SKAYVKFPADIP--DYFKL
SEQ ID NO:16   ----------MVSKGEEVIKEFMRFKHMEGSVNGHEFEIEGEGEGRPYEGTQTARLKVTKGGPLPFAWDILSPQIMYG--SKAYVKFPADIP--DYLKL
SEQ ID NO: 7   XRGSHHHHHHGSRSSKNVIKEFXRFKVRXEGTVNGHEFEIEGEGEGRPYEGHNTVKLKVTKGGPLPFAWDILSPQF--X----SKVYVKEPADIP--DYKKL
SEQ ID NO: 8   ----------MAHSKHGLKEEMTMKYHMEGXVNGHKFVITGEGIGYPFKGKQTINLXVIEGGPLPFSEDILSA-----GXXDRIFTEYPQDIV--DYFKN
SEQ ID NO: 9   ----------MASLLTETMPFKTTIEGTVNGHCFKCIGXGEGNPFEGTQEMKIEVIEGGPLPFAFHILSTSCMYG--SKTFIKYVSGIP--DYFKQ
SEQ ID NO:20   ----------MD-AKLGLKEVMPTKINLEGLVGDHAFSMEGVGEGNILEGTQCEVKISVTKGAPLPFAFDIVSVAFSYG--NRAYTGYPEEIS--DYFLQ
SEQ ID NO:21   ----------MPAMKIECR-TGTLNGVEFLVGGGEGTPEQGRMTNKMKSTKGA-LTFSPYLLSHVMGYG--FYHFGTYPSGYE--NPFLH
SEQ ID NO: 3   ----------MSVPTNLDLH-YGSINGMEFDMVGGGSGNPKDGSLSVNVKSTKGA-LRVSPLLVGPHLGYG--HYQYLPFPDG-P--SPFQA
SEQ ID NO: 2   ----------MSLPTTHDLH-FGSVNGAEFDLVGGGKGNPNDGTLETSVKSTRGA-LPCSPLLIGPNLGYG--FYQYLPFPGG-A--SPFQT
SEQ ID NO: 1   ----------MPLPATHDIHLHGSINGHEFDMVGGGKGDPNAGSLVTTAKSTKGA-LKFSPYLMIPHLGYG--YYQYLPYPDG-P--SPFQA

SEQ ID NO: 4   AM--PEG--YIQERTIFFQDDGKYKTRGEV--KFEGDTLVNRIE-KGMDFKEDGNILGHKLEYNFNSHNVVIMPDKANNGLKVNFKIRHNIEGG---VQ
SEQ ID NO: 5   CF--PEG--LSIDRTVKFENDGTMTSHHTY--ELDDTCVVSRITVNCDGFQPDGPIMRDQLV-DILPNETHMFP-HGPNAVRQLAFIGFTTADGGLMMGH
SEQ ID NO: 6   SF--PKG--YSWERSLTFEDGGICIARNDI--TMEGDTFYNKVRFHGVNFPANGPVMQKKTL-KWEPSTEKMY--VRDGVLTGDITMALLLEGNAHYRCD
SEQ ID NO: 7   SF--PKG--YSWERSLTFEDGGICIARNDI--TMEGDTFYNKVRFHGVNFPANGPVMQKKTL-KWEPSTEKMY--VRDGVLTGDITMALLLEGNAHYRCD
SEQ ID NO: 8   SF--PEG--YSWERSMTFEDGGICTATSDI--TLEGDCFIYEIRFDGVNFPPNGPVMQKKTL-KWEPSTEKMY--VRDGVLKGDVNMALLLEGGGHYRCD
SEQ ID NO: 9   TF--PEG--YSWERSMTYEDGGICTATNDI--TMEGDCFIYKIRFDGVNFPPNGPVMQKKTL-KWEPSTEKMY--VRDGVLKGDVNMALLLEGGGHYRCD
SEQ ID NO:10   TF--PEG--YSWERSMTYEDGGICTATNDI--TMEGDCFIYKIRFDGVNFPPNGPVMQKKTL-KWEPSTEKMY--VRDGVLKGDINMALLLEGGGHYRCD
SEQ ID NO:11   TF--PEG--YIHWERSMTYEDGQGICTATSNI--SMRGDCFFYDIRFDGVNFPPNGPVMQKKTL-KWEPSTEKMY--VRDGVLKGDVNMALLLEGGGHYRCD
SEQ ID NO:12   SF--PEG--YSWERSMTFEDQGVCTVTSDI--KLEGDCFFYEIRFYGVNFPSSGPVMQKKTL-KWEPSTENMY--VRDGVLLGDVSRTLLLEGDKHHRCN
SEQ ID NO:13   TCSGPNG--GYSWQRTMTYEDGGVCIATSNI--SVVGDTFNVDIHFMGANFPLDGPVMQKRTM-KWEPSTEIMF--ERDGMLRGDIAMSLLLKGGGHYRCD
SEQ ID NO:14   SF--PEG--YIWERIMNFEDGAVCTVSNDS--SIQGNCFIYHVKFSGLNFPPNGPVMQKKTQ-GWEPNTERLF--ARDGVLIGNNFMALKLEGGGHYLCE
SEQ ID NO:15   SF--PEG--FKWERVMNFEDGGVVTVTQDS--SL-QDGEFIYKVKLRGTNFPSDGPVMKKMT-GWEASSERMY--PEDGALKGEIKMRLKLKDGGHYTSE
SEQ ID NO:16   SF--PEG--FKWERVMNFEDGGVVTVTQDS--SL-QDGEFIYKVKVRGTNFPSDGPVMKKMT-GWEASSERMY--PEDGALKGEMKMRLRLKDGGHYDAE
SEQ ID NO:17   SF--PEG--FKKERVXNFEDGGVVTVTQDS--SLQDGCFIYKVKFIGVNFPSDGPVXQKKTX-GWEASTERLY--PRDGVLKGEIHKALKLKDGGHYLVE
SEQ ID NO:18   SC--PAG--YTWGRSFLFEDGAVCICNVDITVSVKENCIYHKSIFNGMNFPADGPVMKKMTT-NWEASCHEKIMPVPKQG-LKGDVSMYLLLKDGGRYRCQ
SEQ ID NO:19   SF--PEG--FTWERTTYEDGELTAHQDT--SLDGDCLVYKVKILGNNFPADGPVMQNKVG-RWEPGTEIVY--EVDGVLRGQSLMALKCPGGRHLTCH
SEQ ID NO:20   SF--PEG--FTYERNIRYQDGGTAIVKSDI--SLEDGKFIVNVDFKAKDLRMGPVMQQDIV-GMQPSYESMY--TNVISVIGECIIAFKLQTGKHFTYH
```

FIG. 21 (CONT.)

```
SEQ ID NO:21  AI--NNG-GYTNTRIEKYEDGGVLHVSFSY--RYEAGRVIGDFKVVGTGFPEDSVIFTDKII-RSNATVEHLHP-MGDNVLVGSFARTFSLRDGGYYSFV
SEQ ID NO: 3  AV--NNG-GYQMHRSFNFEDGAVLTATYNY--SYSGGKIQEFHLVGSCFPDDSPVMTNALT-GLDRSVAKLMC-VSDDKLAEFVDWTYRTSSGGRYRAT
SEQ ID NO: 2  AI--TDG-GYQVHRVFKFEDGGVLSCNFRY--TYEGGKIKGEFQLIGSGFPAGGPVMSGGLT-TLDRSVAKLQC-SDDCTITGTNNWSFCTTDGKRHQAD
SEQ ID NO: 1  SM--LEGSGYAVYRVFDFEDGGKLITEFKY--SYEGSHIKADMKLMGSGFPDDGPVMTSQIV-DQDGCVSKKTY-LNNNTIVDSFDWSYNLQNGKRYRAR

SEQ ID NO: 4  LADHYQTNVPLGDGPVLIPINHYLSFQTAISKDRNETRDHMVFLEFFSACGHTHGMDELYK----------------------
SEQ ID NO: 5  FDSKMTFNGSR----AIEIPGPHFVTIITKQMRDTSDKRDH----VCQREVAYAHSVPRITSAIGSDED
SEQ ID NO: 6  FRTTYKAKEKG----VKLPGYHFVDHCIEILSHDKDYNKV----KLYEHAVAHSGLPDNARR-------
SEQ ID NO: 7  FRTTYKAKEKG----VKLPGYHFVDHCIEILSHDKDYNKV----KLYEHAVAHSGLPD----------
SEQ ID NO: 8  FKTTYKAKKGV----ELPDYHFVDHRIBILSHDKDYNNV----KLYEHAVARSSLLPMTAAHHHHHH--
SEQ ID NO: 9  FKTTYKAKKGV----ELPDYHFVDHRIEILSHDKDYNKV----KLYEHAEAHSGLPRLAKAHHHHHH--
SEQ ID NO:10  FKTTYKAKKEG----VKLPDYHFVDHRIEILSHDKDYNEV----KLYEHAEAHSGLPRLAKAHHHHHH--
SEQ ID NO:11  FKTTYKAKKDV----RLPDYHFVDHRIEILKHDKDYNKV----KLYENAVARYSMLPSQAK-------
SEQ ID NO:12  FRSTYGAKKGV----VLPEYHFVDHRIEILSHDKDYNTV----EVYENAVARPSMLPVKAK-------
SEQ ID NO:13  FETIYKPNKVV----KMPDYHFVDHCIEITSQQDYNVV----ELTEVAEARYSSLEKIGKSKA-----
SEQ ID NO:14  FKSTYKAKKPV----KMPGYHFVDRKLDVTNHNKDYTSV----EQREISIARKPVVA-----------
SEQ ID NO:15  VKTTYKAKKPV----QLPGAYIVGIKLDITSHNEDYTIV----EQYERAEGRHSTGGMDELYK------
SEQ ID NO:16  VKTTYMAKKPV----QLPGAYKTDIKLDITSHNEDYTIV----EQYERAEGRHSTGA------------
SEQ ID NO:17  FKSIYXAKKPV----QLPGYYYVDSKLDITSHNEDYTIV----EQYERTEGRHHLFL-------------
SEQ ID NO:18  FDTVYKAKSVP----SKMPEWHFIQHKLLREDRSDAKNQKW--QLTEHAIAFPSALA--------------
SEQ ID NO:19  LHTTYRSKKPA----SALKMPGFHFEDHRIBIMEEVEKGKCY--KQYEAAVGRYCDAAPSKLGHN-----
SEQ ID NO:20  MRTVYKSKKPV----ETMPLYHFIQHRLVKTNVDTASGYV----VQHETAIAAHSTIKKIEGSLP-----
SEQ ID NO:21  VDSHMHFKSAIHPSILQNGGPMFAFRRVEELHSNTELGIV----EYQHAFKTPIAFA------------
SEQ ID NO: 3  VQTNFTFAKPI-AAGLKNNMPMFVFRQLEVTGSKTEIGLQ----EQQKAFSTVL---------------
SEQ ID NO: 2  VQTNYTFAKPL-PAGLKEKMPIFLGHQIEVKASKTEITLS------EKVKAFID---------------
SEQ ID NO: 1  VSSHYIFDKPF-SADLMKKQPVFVYRKCHVKASKTEVTLD------EREKAFYELA-------------
```

FIG. 22

SEQUENCE LISTING

<160> NUMBER OF SEQ ID NOS: 38

<210> SEQ ID NO 1
<211> LENGTH: 219
<212> TYPE: PRT
<213> ORGANISM: Branchiostoma floridae

<400> SEQUENCE: 1

```
Met Pro Leu Pro Ala Thr His Asp Ile His Leu His Gly Ser Ile Asn
1               5                   10                  15

Gly His Glu Phe Asp Met Val Gly Gly Lys Gly Asp Pro Asn Ala
            20                  25                  30

Gly Ser Leu Val Thr Thr Ala Lys Ser Thr Lys Gly Ala Leu Lys Phe
            35                  40                  45

Ser Pro Tyr Leu Met Ile Pro His Leu Gly Tyr Gly Tyr Tyr Gln Tyr
        50                  55                  60

Leu Pro Tyr Pro Asp Gly Pro Ser Pro Phe Gln Ala Ser Met Leu Glu
65                  70                  75                  80

Gly Ser Gly Tyr Ala Val Tyr Arg Val Phe Asp Phe Glu Asp Gly Gly
                85                  90                  95

Lys Leu Thr Thr Glu Phe Lys Tyr Ser Tyr Glu Gly Ser His Ile Lys
            100                 105                 110

Ala Asp Met Lys Leu Met Gly Ser Gly Phe Pro Asp Asp Gly Pro Val
            115                 120                 125

Met Thr Ser Gln Ile Val Asp Gln Asp Gly Cys Val Ser Lys Lys Thr
        130                 135                 140

Tyr Leu Asn Asn Asn Thr Ile Val Asp Ser Phe Asp Trp Ser Tyr Asn
145                 150                 155                 160

Leu Gln Asn Gly Lys Arg Tyr Arg Ala Arg Val Ser Ser His Tyr Ile
                165                 170                 175

Phe Asp Lys Pro Phe Ser Ala Asp Leu Met Lys Lys Gln Pro Val Phe
            180                 185                 190

Val Tyr Arg Lys Cys His Val Lys Ala Ser Lys Thr Glu Val Thr Leu
        195                 200                 205

Asp Glu Arg Glu Lys Ala Phe Tyr Glu Leu Ala
    210                 215
```

<210> SEQ ID NO 2
<211> LENGTH: 216
<212> TYPE: PRT
<213> ORGANISM: Branchiostoma floridae

<400> SEQUENCE: 2

```
Met Ser Leu Pro Thr Thr His Asp Leu His Ile Phe Gly Ser Val Asn
1               5                   10                  15

Gly Ala Glu Phe Asp Leu Val Gly Gly Lys Gly Asn Pro Asn Asp
            20                  25                  30

Gly Thr Leu Glu Thr Ser Val Lys Ser Thr Arg Gly Ala Leu Pro Cys
            35                  40                  45

Ser Pro Leu Leu Ile Gly Pro Asn Leu Gly Tyr Gly Phe Tyr Gln Tyr
        50                  55                  60

Leu Pro Phe Pro Gly Gly Ala Ser Pro Phe Gln Thr Ala Ile Thr Asp
65                  70                  75                  80

Gly Gly Tyr Gln Val His Arg Val Phe Lys Phe Glu Asp Gly Gly Val
                85                  90                  95

Leu Ser Cys Asn Phe Arg Tyr Thr Tyr Glu Gly Gly Lys Ile Lys Gly
```

```
                    100                 105                 110
Glu Phe Gln Leu Ile Gly Ser Gly Phe Pro Ala Gly Gly Pro Val Met
            115                 120                 125

Ser Gly Gly Leu Thr Thr Leu Asp Arg Ser Val Ala Lys Leu Gln Cys
            130                 135                 140

Ser Asp Asp Cys Thr Ile Thr Gly Thr Asn Asn Trp Ser Phe Cys Thr
145                 150                 155                 160

Thr Asp Gly Lys Arg His Gln Ala Asp Val Gln Thr Asn Tyr Thr Phe
                165                 170                 175

Ala Lys Pro Leu Pro Ala Gly Leu Lys Glu Lys Met Pro Ile Phe Leu
            180                 185                 190

Gly His Gln Ile Glu Val Lys Ala Ser Lys Thr Glu Ile Thr Leu Ser
            195                 200                 205

Glu Lys Val Lys Ala Phe Ile Asp
            210                 215

<210> SEQ ID NO 3
<211> LENGTH: 218
<212> TYPE: PRT
<213> ORGANISM: Branchiostoma floridae

<400> SEQUENCE: 3

Met Ser Val Pro Thr Asn Leu Asp Leu His Ile Tyr Gly Ser Ile Asn
1               5                   10                  15

Gly Met Glu Phe Asp Met Val Gly Gly Ser Gly Asn Pro Lys Asp
            20                  25                  30

Gly Ser Leu Ser Val Asn Val Lys Ser Thr Lys Gly Ala Leu Arg Val
        35                  40                  45

Ser Pro Leu Leu Val Gly Pro His Leu Gly Tyr Gly His Tyr Gln Tyr
    50                  55                  60

Leu Pro Phe Pro Asp Gly Pro Ser Pro Phe Gln Ala Ala Val Asn Asn
65                  70                  75                  80

Gly Gly Tyr Gln Met His Arg Ser Phe Asn Phe Glu Asp Gly Ala Val
                85                  90                  95

Leu Thr Ala Thr Tyr Asn Tyr Ser Tyr Ser Gly Gly Lys Ile Gln Gly
            100                 105                 110

Glu Phe His Leu Val Gly Ser Cys Phe Pro Asp Asp Ser Pro Val Met
            115                 120                 125

Thr Asn Ala Leu Thr Gly Leu Asp Arg Ser Val Ala Lys Leu Met Cys
            130                 135                 140

Val Ser Asp Asp Lys Leu Ala Glu Phe Val Asp Trp Thr Tyr Arg Thr
145                 150                 155                 160

Ser Ser Gly Gly Arg Tyr Arg Ala Thr Val Gln Thr Asn Phe Thr Phe
                165                 170                 175

Ala Lys Pro Ile Ala Ala Gly Leu Lys Asn Asn Met Pro Met Phe Val
            180                 185                 190

Phe Arg Gln Leu Glu Val Thr Gly Ser Lys Thr Glu Ile Gly Leu Gln
            195                 200                 205

Glu Gln Gln Lys Ala Phe Ser Thr Val Leu
            210                 215

<210> SEQ ID NO 4
<211> LENGTH: 238
<212> TYPE: PRT
<213> ORGANISM: Aequorea macrodactyla
```

```
<400> SEQUENCE: 4

Met Ser Lys Gly Glu Glu Leu Phe Thr Gly Ile Val Pro Val Leu Ile
1               5                   10                  15

Glu Leu Asp Gly Asp Val His Gly His Lys Phe Ser Val Arg Gly Glu
                20                  25                  30

Gly Glu Gly Asp Ala Asp Tyr Gly Lys Leu Glu Ile Lys Phe Ile Cys
            35                  40                  45

Thr Thr Gly Lys Leu Pro Val Pro Trp Pro Thr Leu Val Thr Thr Leu
        50                  55                  60

Gly Tyr Gly Ile Gln Cys Phe Ala Arg Tyr Pro Glu His Met Lys Met
65                  70                  75                  80

Asn Asp Phe Phe Lys Ser Ala Met Pro Glu Gly Tyr Ile Gln Glu Arg
                85                  90                  95

Thr Ile Phe Phe Gln Asp Gly Lys Tyr Lys Thr Arg Gly Glu Val
            100                 105                 110

Lys Phe Glu Gly Asp Thr Leu Val Asn Arg Ile Glu Leu Lys Gly Met
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Met Pro Asp Lys Ala Asn Asn Gly
145                 150                 155                 160

Leu Lys Val Asn Phe Lys Ile Arg His Asn Ile Glu Gly Gly Val
                165                 170                 175

Gln Leu Ala Asp His Tyr Gln Thr Asn Val Pro Leu Gly Asp Gly Pro
            180                 185                 190

Val Leu Ile Pro Ile Asn His Tyr Leu Ser Phe Gln Thr Ala Ile Ser
        195                 200                 205

Lys Asp Arg Asn Glu Thr Arg Asp His Met Val Phe Leu Glu Phe Phe
    210                 215                 220

Ser Ala Cys Gly His Thr His Gly Met Asp Glu Leu Tyr Lys
225                 230                 235

<210> SEQ ID NO 5
<211> LENGTH: 237
<212> TYPE: PRT
<213> ORGANISM: Anthomedusae sp. DC-2005

<400> SEQUENCE: 5

Met Glu Gly Gly Pro Ala Leu Phe Gln Ser Asp Met Thr Phe Lys Ile
1               5                   10                  15

Phe Ile Asp Gly Glu Val Asn Gly Gln Lys Phe Thr Ile Val Ala Asp
                20                  25                  30

Gly Ser Ser Lys Phe Pro His Gly Asp Phe Asn Val His Ala Val Cys
            35                  40                  45

Glu Thr Gly Lys Leu Pro Met Ser Trp Lys Pro Ile Cys His Leu Ile
        50                  55                  60

Gln Tyr Gly Glu Pro Phe Phe Ala Arg Tyr Pro Asp Gly Ile Ser His
65                  70                  75                  80

Phe Ala Gln Glu Cys Phe Pro Glu Gly Leu Ser Ile Asp Arg Thr Val
                85                  90                  95

Arg Phe Glu Asn Asp Gly Thr Met Thr Ser His His Thr Tyr Glu Leu
            100                 105                 110

Asp Asp Thr Cys Val Val Ser Arg Ile Thr Val Asn Cys Asp Gly Phe
        115                 120                 125
```

```
Gln Pro Asp Gly Pro Ile Met Arg Asp Gln Leu Val Asp Ile Leu Pro
        130                 135                 140

Asn Glu Thr His Met Phe Pro His Gly Pro Asn Ala Val Arg Gln Leu
145                 150                 155                 160

Ala Phe Ile Gly Phe Thr Thr Ala Asp Gly Leu Met Met Gly His
                165                 170                 175

Phe Asp Ser Lys Met Thr Phe Asn Gly Ser Arg Ala Ile Glu Ile Pro
                180                 185                 190

Gly Pro His Phe Val Thr Ile Ile Thr Lys Gln Met Arg Asp Thr Ser
                195                 200                 205

Asp Lys Arg Asp His Val Cys Gln Arg Glu Val Ala Tyr Ala His Ser
210                 215                 220

Val Pro Arg Ile Thr Ser Ala Ile Gly Ser Asp Glu Asp
225                 230                 235

<210> SEQ ID NO 6
<211> LENGTH: 226
<212> TYPE: PRT
<213> ORGANISM: Lobophyllia hemprichii

<400> SEQUENCE: 6

Met Ser Ala Ile Lys Pro Asp Met Lys Ile Asn Leu Arg Met Glu Gly
1               5                   10                  15

Asn Val Asn Gly His His Phe Val Ile Asp Gly Asp Gly Thr Gly Lys
                20                  25                  30

Pro Phe Glu Gly Lys Gln Ser Met Asp Leu Glu Val Lys Glu Gly Gly
                35                  40                  45

Pro Leu Pro Phe Ala Phe Asp Ile Leu Thr Thr Ala Phe His Tyr Gly
50                  55                  60

Asn Arg Val Phe Ala Glu Tyr Pro Asp His Ile Gln Asp Tyr Phe Lys
65                  70                  75                  80

Gln Ser Phe Pro Lys Gly Tyr Ser Trp Glu Arg Ser Leu Thr Phe Glu
                85                  90                  95

Asp Gly Gly Ile Cys Ile Ala Arg Asn Asp Ile Thr Met Glu Gly Asp
                100                 105                 110

Thr Phe Tyr Asn Lys Val Arg Phe His Gly Val Asn Phe Pro Ala Asn
                115                 120                 125

Gly Pro Val Met Gln Lys Lys Thr Leu Lys Trp Glu Pro Ser Thr Glu
130                 135                 140

Lys Met Tyr Val Arg Asp Gly Val Leu Thr Gly Asp Ile Thr Met Ala
145                 150                 155                 160

Leu Leu Leu Glu Gly Asn Ala His Tyr Arg Cys Asp Phe Arg Thr Thr
                165                 170                 175

Tyr Lys Ala Lys Glu Lys Gly Val Lys Leu Pro Gly Tyr His Phe Val
                180                 185                 190

Asp His Cys Ile Glu Ile Leu Ser His Asp Lys Asp Tyr Asn Lys Val
                195                 200                 205

Lys Leu Tyr Glu His Ala Val Ala His Ser Gly Leu Pro Asp Asn Ala
210                 215                 220

Arg Arg
225

<210> SEQ ID NO 7
<211> LENGTH: 222
<212> TYPE: PRT
<213> ORGANISM: Lobophyllia hemprichii
```

<220> FEATURE:
<221> NAME/KEY: misc_feature
<222> LOCATION: (61)..(61)
<223> OTHER INFORMATION: Xaa can be any naturally occurring amino acid

<400> SEQUENCE: 7

Gly Gly Ala Ile Lys Pro Asp Met Lys Ile Asn Leu Arg Met Glu Gly
1               5                   10                  15

Asn Val Asn Gly His His Phe Val Ile Asp Gly Asp Gly Thr Gly Lys
            20                  25                  30

Pro Phe Glu Gly Lys Gln Ser Met Asp Leu Glu Val Lys Glu Gly Gly
        35                  40                  45

Pro Leu Pro Phe Ala Phe Asp Ile Leu Thr Thr Ala Xaa His Tyr Gly
    50                  55                  60

Asn Arg Val Phe Ala Glu Tyr Pro Asp His Ile Gln Asp Tyr Phe Lys
65                  70                  75                  80

Gln Ser Phe Pro Lys Gly Tyr Ser Trp Glu Arg Ser Leu Thr Phe Glu
                85                  90                  95

Asp Gly Gly Ile Cys Ile Ala Arg Asn Asp Ile Thr Met Glu Gly Asp
            100                 105                 110

Thr Phe Tyr Asn Lys Val Arg Phe His Gly Val Asn Phe Pro Ala Asn
        115                 120                 125

Gly Pro Val Met Gln Lys Lys Thr Leu Lys Trp Glu Pro Ser Thr Glu
    130                 135                 140

Lys Met Tyr Val Arg Asp Gly Val Leu Thr Gly Asp Ile Thr Met Ala
145                 150                 155                 160

Leu Leu Leu Glu Gly Asn Ala His Tyr Arg Cys Asp Phe Arg Thr Thr
                165                 170                 175

Tyr Lys Ala Lys Glu Lys Gly Val Lys Leu Pro Gly Tyr His Phe Val
            180                 185                 190

Asp His Cys Ile Glu Ile Leu Ser His Asp Lys Asp Tyr Asn Lys Val
        195                 200                 205

Lys Leu Tyr Glu His Ala Val Ala His Ser Gly Leu Pro Asp
    210                 215                 220

<210> SEQ ID NO 8
<211> LENGTH: 231
<212> TYPE: PRT
<213> ORGANISM: Artificial
<220> FEATURE:
<223> OTHER INFORMATION: Bacterial and Plant Plastid Code

<400> SEQUENCE: 8

Met Ser Val Ile Lys Ser Asp Met Lys Ile Lys Leu Arg Met Glu Gly
1               5                   10                  15

Thr Val Asn Gly His Lys Phe Val Ile Glu Gly Glu Gly Glu Gly Lys
            20                  25                  30

Pro Tyr Glu Gly Thr Gln Thr Met Asn Leu Lys Val Lys Glu Gly Ala
        35                  40                  45

Pro Leu Pro Phe Ala Tyr Asp Ile Leu Thr Thr Ala Phe Gln Tyr Gly
    50                  55                  60

Asn Arg Val Phe Thr Lys Tyr Pro Lys Asp Ile Pro Asp Tyr Phe Lys
65                  70                  75                  80

Gln Ser Phe Pro Glu Gly Tyr Ser Trp Glu Arg Ser Met Thr Phe Glu
                85                  90                  95

Asp Gly Gly Ile Cys Thr Ala Thr Ser Asp Ile Thr Leu Glu Gly Asp
            100                 105                 110

Cys Phe Ile Tyr Glu Ile Arg Phe Asp Gly Val Asn Phe Pro Pro Asn
            115                 120                 125

Gly Pro Val Met Gln Lys Lys Thr Leu Lys Trp Glu Pro Ser Thr Glu
        130                 135                 140

Lys Met Tyr Val Arg Asp Gly Val Leu Lys Gly Asp Val Asn Met Ala
145                 150                 155                 160

Leu Leu Leu Glu Gly Gly His Tyr Arg Cys Asp Phe Lys Thr Thr
                165                 170                 175

Tyr Lys Ala Lys Lys Gly Val Glu Leu Pro Asp Tyr His Phe Val Asp
            180                 185                 190

His Arg Ile Glu Ile Leu Ser His Asp Lys Asp Tyr Asn Asn Val Lys
            195                 200                 205

Leu Tyr Glu His Ala Val Ala Arg Ser Ser Leu Leu Pro Met Thr Ala
        210                 215                 220

Ala His His His His His His
225                 230

<210> SEQ ID NO 9
<211> LENGTH: 231
<212> TYPE: PRT
<213> ORGANISM: Artificial
<220> FEATURE:
<223> OTHER INFORMATION: Bacterial and Plant Plastid Code

<400> SEQUENCE: 9

Met Ser Val Ile Lys Ser Asp Met Lys Ile Lys Leu Arg Met Glu Gly
1               5                   10                  15

Thr Val Asn Gly His Lys Phe Val Ile Glu Gly Glu Gly Glu Gly Lys
            20                  25                  30

Pro Tyr Glu Gly Thr Gln Ser Met Asp Leu Thr Val Lys Glu Gly Ala
        35                  40                  45

Pro Leu Pro Phe Ala Tyr Asp Ile Leu Thr Thr Val Phe His Tyr Gly
    50                  55                  60

Asn Arg Val Phe Ala Lys Tyr Pro Lys Asp Ile Pro Asp Tyr Phe Lys
65                  70                  75                  80

Gln Thr Phe Pro Glu Gly Tyr Ser Trp Glu Arg Ser Met Thr Tyr Glu
                85                  90                  95

Asp Gly Gly Ile Cys Thr Ala Thr Asn Asp Ile Thr Met Glu Gly Asp
            100                 105                 110

Cys Phe Ile Tyr Lys Ile Arg Phe Asp Gly Val Asn Phe Pro Pro Asn
        115                 120                 125

Gly Pro Val Met Gln Lys Lys Thr Leu Lys Trp Glu Pro Ser Thr Glu
    130                 135                 140

Lys Met Tyr Val Arg Asp Gly Val Leu Lys Gly Asp Val Asn Met Ala
145                 150                 155                 160

Leu Leu Leu Glu Gly Gly Gly His Tyr Arg Cys Asp Phe Lys Thr Thr
                165                 170                 175

Tyr Lys Ala Lys Lys Gly Val Glu Leu Pro Asp Tyr His Phe Val Asp
            180                 185                 190

His Arg Ile Glu Ile Leu Ser His Asp Lys Asp Tyr Asn Lys Val Lys
            195                 200                 205

Leu Tyr Glu His Ala Glu Ala His Ser Gly Leu Pro Arg Leu Ala Lys
        210                 215                 220

Ala His His His His His His
225                 230

<210> SEQ ID NO 10
<211> LENGTH: 232
<212> TYPE: PRT
<213> ORGANISM: Artificial
<220> FEATURE:
<223> OTHER INFORMATION: Bacterial and Plant Plastid Code

<400> SEQUENCE: 10

Met Ser Val Ile Lys Ser Val Met Lys Ile Lys Leu Arg Met Glu Gly
1               5                   10                  15

Ala Val Asn Gly His Asn Phe Val Ile Val Gly Glu Gly Glu Gly Lys
            20                  25                  30

Pro Tyr Glu Gly Thr Gln Ser Met Asp Leu Thr Val Lys Glu Gly Ala
        35                  40                  45

Pro Leu Pro Phe Ala Tyr Asp Ile Leu Thr Thr Val Phe His Tyr Gly
    50                  55                  60

Asn Arg Val Phe Ala Lys Tyr Pro Lys Asp Ile Pro Asp Tyr Phe Lys
65                  70                  75                  80

Gln Thr Phe Pro Glu Gly Tyr Ser Trp Glu Arg Ser Met Thr Phe Glu
                85                  90                  95

Asp Gly Gly Ile Cys Thr Ala Thr Asn Asp Ile Thr Met Glu Gly Asp
            100                 105                 110

Cys Phe Ile Tyr Lys Ile Arg Phe Asp Gly Val Asn Phe Pro Pro Asn
        115                 120                 125

Gly Pro Val Met Gln Lys Lys Thr Leu Lys Trp Glu Pro Ser Thr Glu
    130                 135                 140

Lys Met Tyr Val Arg Asp Gly Val Leu Lys Gly Asp Ile Asn Met Ala
145                 150                 155                 160

Leu Leu Leu Glu Gly Gly Gly His Tyr Arg Cys Asp Phe Lys Thr Thr
                165                 170                 175

Tyr Lys Ala Lys Lys Glu Gly Val Lys Leu Pro Asp Tyr His Phe Val
            180                 185                 190

Asp His Arg Ile Glu Ile Leu Ser His Asp Lys Asp Tyr Asn Glu Val
        195                 200                 205

Lys Leu Tyr Glu His Ala Glu Ala His Ser Gly Leu Pro Arg Leu Ala
    210                 215                 220

Lys Ala His His His His His His
225                 230

<210> SEQ ID NO 11
<211> LENGTH: 225
<212> TYPE: PRT
<213> ORGANISM: Galaxea fascicularis

<400> SEQUENCE: 11

Met Ser Val Ile Lys Pro Glu Met Lys Ile Lys Leu Cys Met Arg Gly
1               5                   10                  15

Thr Val Asn Gly His Asn Phe Val Ile Glu Gly Glu Gly Lys Gly Asn
            20                  25                  30

Pro Tyr Glu Gly Thr Gln Ile Leu Asp Leu Asn Val Thr Glu Gly Ala
        35                  40                  45

Pro Leu Pro Phe Ala Tyr Asp Ile Leu Thr Thr Val Phe Gln Tyr Gly
    50                  55                  60

Asn Arg Ala Phe Thr Lys Tyr Pro Ala Asp Ile Gln Asp Tyr Phe Lys
65                  70                  75                  80

-continued

```
Gln Thr Phe Pro Glu Gly Tyr His Trp Glu Arg Ser Met Thr Tyr Glu
                85                  90                  95

Asp Gln Gly Ile Cys Thr Ala Thr Ser Asn Ile Ser Met Arg Gly Asp
            100                 105                 110

Cys Phe Phe Tyr Asp Ile Arg Phe Asp Gly Val Asn Phe Pro Pro Asn
            115                 120                 125

Gly Pro Val Met Gln Lys Lys Thr Leu Lys Trp Glu Pro Ser Thr Glu
            130                 135                 140

Lys Met Tyr Val Arg Asp Gly Val Leu Lys Gly Asp Val Asn Met Ala
145                 150                 155                 160

Leu Leu Leu Glu Gly Gly Gly His Tyr Arg Cys Asp Phe Lys Thr Thr
                165                 170                 175

Tyr Lys Ala Lys Lys Asp Val Arg Leu Pro Asp Tyr His Phe Val Asp
            180                 185                 190

His Arg Ile Glu Ile Leu Lys His Asp Lys Asp Tyr Asn Lys Val Lys
            195                 200                 205

Leu Tyr Glu Asn Ala Val Ala Arg Tyr Ser Met Leu Pro Ser Gln Ala
    210                 215                 220

Lys
225

<210> SEQ ID NO 12
<211> LENGTH: 225
<212> TYPE: PRT
<213> ORGANISM: Montastraea cavernosa

<400> SEQUENCE: 12

Met Ser Val Ile Lys Ser Val Met Lys Ile Lys Leu Arg Met Asp Gly
1               5                   10                  15

Ile Val Asn Gly His Lys Phe Met Ile Thr Gly Glu Gly Glu Gly Lys
            20                  25                  30

Pro Phe Glu Gly Thr His Thr Ile Ile Leu Lys Val Lys Glu Gly Gly
            35                  40                  45

Pro Leu Pro Phe Ala Tyr Asp Ile Leu Thr Thr Ala Phe Gln Tyr Gly
    50                  55                  60

Asn Arg Val Phe Thr Lys Tyr Pro Lys Asp Ile Pro Asp Tyr Phe Lys
65                  70                  75                  80

Gln Ser Phe Pro Glu Gly Tyr Ser Trp Glu Arg Ser Met Thr Phe Glu
                85                  90                  95

Asp Gln Gly Val Cys Thr Val Thr Ser Asp Ile Lys Leu Glu Gly Asp
            100                 105                 110

Cys Phe Phe Tyr Glu Ile Arg Phe Tyr Gly Val Asn Phe Pro Ser Ser
            115                 120                 125

Gly Pro Val Met Gln Lys Lys Thr Leu Lys Trp Glu Pro Ser Thr Glu
            130                 135                 140

Asn Met Tyr Val Arg Asp Gly Val Leu Gly Asp Val Ser Arg Thr
145                 150                 155                 160

Leu Leu Leu Glu Gly Asp Lys His Arg Cys Asn Phe Arg Ser Thr
                165                 170                 175

Tyr Gly Ala Lys Lys Gly Val Val Leu Pro Glu Tyr His Phe Val Asp
            180                 185                 190

His Arg Ile Glu Ile Leu Ser His Asp Lys Asp Tyr Asn Thr Val Glu
            195                 200                 205

Val Tyr Glu Asn Ala Val Ala Arg Pro Ser Met Leu Pro Val Lys Ala
    210                 215                 220
```

Lys
225

<210> SEQ ID NO 13
<211> LENGTH: 231
<212> TYPE: PRT
<213> ORGANISM: Discosoma sp. SSAL-2002

<400> SEQUENCE: 13

Met Ser Ala Leu Lys Glu Glu Met Lys Ile Asn Leu Thr Met Glu Gly
1               5                   10                  15

Val Val Asn Gly Leu Pro Phe Lys Ile Arg Gly Asp Gly Lys Gly Lys
            20                  25                  30

Pro Tyr Gln Gly Ser Gln Glu Leu Thr Leu Thr Val Lys Gly Gly
        35                  40                  45

Pro Leu Pro Phe Ser Tyr Asp Ile Leu Thr Thr Met Phe Gln Tyr Gly
    50                  55                  60

Asn Arg Ala Phe Val Asn Tyr Pro Glu Asp Ile Pro Asp Ile Phe Lys
65                  70                  75                  80

Gln Thr Cys Ser Gly Pro Asn Gly Gly Tyr Ser Trp Gln Arg Thr Met
                85                  90                  95

Thr Tyr Glu Asp Gly Gly Val Cys Thr Ala Thr Ser Asn Ile Ser Val
            100                 105                 110

Val Gly Asp Thr Phe Asn Tyr Asp Ile His Phe Met Gly Ala Asn Phe
        115                 120                 125

Pro Leu Asp Gly Pro Val Met Gln Lys Arg Thr Met Lys Trp Glu Pro
    130                 135                 140

Ser Thr Glu Ile Met Phe Glu Arg Asp Gly Met Leu Arg Gly Asp Ile
145                 150                 155                 160

Ala Met Ser Leu Leu Leu Lys Gly Gly Gly His Tyr Arg Cys Asp Phe
                165                 170                 175

Glu Thr Ile Tyr Lys Pro Asn Lys Val Val Lys Met Pro Asp Tyr His
            180                 185                 190

Phe Val Asp His Cys Ile Glu Ile Thr Ser Gln Gln Asp Tyr Tyr Asn
        195                 200                 205

Val Val Glu Leu Thr Glu Val Ala Glu Ala Arg Tyr Ser Ser Leu Glu
    210                 215                 220

Lys Ile Gly Lys Ser Lys Ala
225                 230

<210> SEQ ID NO 14
<211> LENGTH: 221
<212> TYPE: PRT
<213> ORGANISM: Acropora hyacinthus

<400> SEQUENCE: 14

Met Ser Val Ile Ala Thr Gln Met Thr Tyr Lys Val Tyr Met Ser Gly
1               5                   10                  15

Thr Val Asn Gly His Tyr Phe Glu Val Glu Gly Asp Gly Lys Gly Lys
            20                  25                  30

Pro Tyr Glu Gly Glu Gln Thr Val Arg Leu Thr Val Thr Lys Gly Gly
        35                  40                  45

Pro Leu Pro Phe Ala Trp Asp Ile Leu Ser Pro Gln Ser Gln Tyr Gly
    50                  55                  60

Ser Ile Pro Phe Thr Lys Tyr Pro Glu Asp Ile Pro Asp Tyr Val Lys
65                  70                  75                  80

Gln Ser Phe Pro Glu Gly Tyr Thr Trp Glu Arg Ile Met Asn Phe Glu
                85                  90                  95

Asp Gly Ala Val Cys Thr Val Ser Asn Asp Ser Ser Ile Gln Gly Asn
            100                 105                 110

Cys Phe Ile Tyr His Val Lys Phe Ser Gly Leu Asn Phe Pro Pro Asn
        115                 120                 125

Gly Pro Val Met Gln Lys Lys Thr Gln Gly Trp Glu Pro Asn Thr Glu
    130                 135                 140

Arg Leu Phe Ala Arg Asp Gly Val Leu Ile Gly Asn Asn Phe Met Ala
145                 150                 155                 160

Leu Lys Leu Glu Gly Gly His Tyr Leu Cys Glu Phe Lys Ser Thr
                165                 170                 175

Tyr Lys Ala Lys Lys Pro Val Lys Met Pro Gly Tyr His Phe Val Asp
            180                 185                 190

Arg Lys Leu Asp Val Thr Asn His Asn Lys Asp Tyr Thr Ser Val Glu
        195                 200                 205

Gln Arg Glu Ile Ser Ile Ala Arg Lys Pro Val Val Ala
    210                 215                 220

<210> SEQ ID NO 15
<211> LENGTH: 236
<212> TYPE: PRT
<213> ORGANISM: Artificial
<220> FEATURE:
<223> OTHER INFORMATION: Bacterial and Plant Plastid Code

<400> SEQUENCE: 15

Met Val Ser Lys Gly Glu Glu Asn Asn Met Ala Ile Ile Lys Glu Phe
1               5                   10                  15

Met Arg Phe Lys Val Arg Met Glu Gly Ser Val Asn Gly His Glu Phe
            20                  25                  30

Glu Ile Glu Gly Glu Gly Glu Gly Arg Pro Tyr Glu Gly Phe Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Thr Tyr Gly Ser Lys Ala Tyr Val Lys His
65                  70                  75                  80

Pro Ala Asp Ile Pro Asp Tyr Phe Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Met Arg Leu Lys Leu Lys Asp Gly Gly
                165                 170                 175

His Tyr Thr Ser Glu Val Lys Thr Thr Tyr Lys Ala Lys Lys Pro Val
            180                 185                 190

Gln Leu Pro Gly Ala Tyr Ile Val Gly Ile Lys Leu Asp Ile Thr Ser
        195                 200                 205

His Asn Glu Asp Tyr Thr Ile Val Glu Gln Tyr Glu Arg Ala Glu Gly
    210                 215                 220

```
Arg His Ser Thr Gly Gly Met Asp Glu Leu Tyr Lys
225                 230                 235

<210> SEQ ID NO 16
<211> LENGTH: 226
<212> TYPE: PRT
<213> ORGANISM: Discosoma sp. LW-2004

<400> SEQUENCE: 16

Met Val Ser Lys Gly Glu Glu Val Ile Lys Glu Phe Met Arg Phe Lys
1               5                   10                  15

Glu His Met Glu Gly Ser Val Asn Gly His Glu Phe Glu Ile Glu Gly
            20                  25                  30

Glu Gly Glu Gly Arg Pro Tyr Glu Gly Thr Gln Thr Ala Arg Leu Lys
        35                  40                  45

Val Thr Lys Gly Gly Pro Leu Pro Phe Ala Trp Asp Ile Leu Ser Pro
    50                  55                  60

Gln Ile Met Tyr Gly Ser Lys Ala Tyr Val Lys His Pro Ala Asp Ile
65                  70                  75                  80

Pro Asp Tyr Leu Lys Leu Ser Phe Pro Glu Gly Phe Lys Trp Glu Arg
                85                  90                  95

Val Met Asn Phe Glu Asp Gly Gly Val Val Thr Val Thr Gln Asp Ser
            100                 105                 110

Ser Leu Gln Asp Gly Glu Phe Ile Tyr Lys Val Lys Val Arg Gly Thr
        115                 120                 125

Asn Phe Pro Ser Asp Gly Pro Val Met Gln Lys Lys Thr Met Gly Trp
130                 135                 140

Glu Ala Ser Ser Glu Arg Met Tyr Pro Glu Asp Gly Ala Leu Lys Gly
145                 150                 155                 160

Glu Met Lys Met Arg Leu Arg Leu Lys Asp Gly Gly His Tyr Asp Ala
                165                 170                 175

Glu Val Lys Thr Thr Tyr Met Ala Lys Lys Pro Val Gln Leu Pro Gly
            180                 185                 190

Ala Tyr Lys Thr Asp Ile Lys Leu Asp Ile Thr Ser His Asn Glu Asp
        195                 200                 205

Tyr Thr Ile Val Glu Gln Tyr Glu Arg Ala Glu Gly Arg His Ser Thr
    210                 215                 220

Gly Ala
225

<210> SEQ ID NO 17
<211> LENGTH: 234
<212> TYPE: PRT
<213> ORGANISM: Discosoma sp.
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid
<220> FEATURE:
```

<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (145)..(145)
<223> OTHER INFORMATION: Xaa can be any naturally occurring amino acid
<220> FEATURE:
<221> NAME/KEY: misc_feature
<222> LOCATION: (150)..(150)
<223> OTHER INFORMATION: Xaa can be any naturally occurring amino acid
<220> FEATURE:
<221> NAME/KEY: misc_feature
<222> LOCATION: (191)..(191)
<223> OTHER INFORMATION: Xaa can be any naturally occurring amino acid

<400> SEQUENCE: 17

Xaa Arg Gly Ser His His His His His Gly Ser Arg Ser Lys
1               5                   10                  15

Asn Val Ile Lys Glu Phe Xaa Arg Phe Lys Val Arg Xaa Glu Gly Thr
            20                  25                  30

Val Asn Gly His Glu Phe Glu Ile Glu Gly Glu Gly Arg Pro
        35                  40                  45

Tyr Glu Gly His Asn Thr Val Lys Leu Lys Val Thr Lys Gly Pro
50                  55                  60

Leu Pro Phe Ala Trp Asp Ile Leu Ser Pro Gln Phe Xaa Ser Lys Val
65                  70                  75                  80

Tyr Val Lys His Pro Ala Asp Ile Pro Asp Tyr Lys Lys Leu Ser Phe
                85                  90                  95

Pro Glu Gly Phe Lys Trp Glu Arg Val Xaa Asn Phe Glu Asp Gly Gly
            100                 105                 110

Val Val Thr Val Thr Gln Asp Ser Ser Leu Gln Asp Gly Cys Phe Ile
        115                 120                 125

Tyr Lys Val Lys Phe Ile Gly Val Asn Phe Pro Ser Asp Gly Pro Val
130                 135                 140

Xaa Gln Lys Lys Thr Xaa Gly Trp Glu Ala Ser Thr Glu Arg Leu Tyr
145                 150                 155                 160

Pro Arg Asp Gly Val Leu Lys Gly Glu Ile His Lys Ala Leu Lys Leu
                165                 170                 175

Lys Asp Gly Gly His Tyr Leu Val Glu Phe Lys Ser Ile Tyr Xaa Ala
            180                 185                 190

Lys Lys Pro Val Gln Leu Pro Gly Tyr Tyr Val Asp Ser Lys Leu
        195                 200                 205

Asp Ile Thr Ser His Asn Glu Asp Tyr Thr Ile Val Glu Gln Tyr Glu
210                 215                 220

Arg Thr Glu Gly Arg His His Leu Phe Leu
225                 230

<210> SEQ ID NO 18
<211> LENGTH: 229
<212> TYPE: PRT
<213> ORGANISM: Zoanthus sp.
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (65)..(66)

<223> OTHER INFORMATION: Xaa can be any naturally occurring amino acid

<400> SEQUENCE: 18

```
Met Ala His Ser Lys His Gly Leu Lys Glu Glu Thr Met Lys Tyr
1               5                   10                  15

His Met Glu Gly Xaa Val Asn Gly His Lys Phe Val Ile Thr Gly Glu
                20                  25                  30

Gly Ile Gly Tyr Pro Phe Lys Gly Lys Gln Thr Ile Asn Leu Xaa Val
            35                  40                  45

Ile Glu Gly Gly Pro Leu Pro Phe Ser Glu Asp Ile Leu Ser Ala Gly
50                  55                  60

Xaa Xaa Asp Arg Ile Phe Thr Glu Tyr Pro Gln Asp Ile Val Asp Tyr
65                  70                  75                  80

Phe Lys Asn Ser Cys Pro Ala Gly Tyr Thr Trp Gly Arg Ser Phe Leu
                85                  90                  95

Phe Glu Asp Gly Ala Val Cys Ile Cys Asn Val Asp Ile Thr Val Ser
            100                 105                 110

Val Lys Glu Asn Cys Ile Tyr His Lys Ser Ile Phe Asn Gly Met Asn
        115                 120                 125

Phe Pro Ala Asp Gly Pro Val Met Lys Lys Met Thr Thr Asn Trp Glu
130                 135                 140

Ala Ser Cys Glu Lys Ile Met Pro Val Pro Lys Gln Gly Ile Leu Lys
145                 150                 155                 160

Gly Asp Val Ser Met Tyr Leu Leu Leu Lys Asp Gly Gly Arg Tyr Arg
                165                 170                 175

Cys Gln Phe Asp Thr Val Tyr Lys Ala Lys Ser Val Pro Ser Lys Met
            180                 185                 190

Pro Glu Trp His Phe Ile Gln His Lys Leu Leu Arg Glu Asp Arg Ser
        195                 200                 205

Asp Ala Lys Asn Gln Lys Trp Gln Leu Thr Glu His Ala Ile Ala Phe
210                 215                 220

Pro Ser Ala Leu Ala
225
```

<210> SEQ ID NO 19
<211> LENGTH: 232
<212> TYPE: PRT
<213> ORGANISM: Artificial
<220> FEATURE:
<223> OTHER INFORMATION: Bacterial and Plant Plastid

<400> SEQUENCE: 19

```
Met Ala Ser Leu Leu Thr Glu Thr Met Pro Phe Lys Thr Thr Ile Glu
1               5                   10                  15

Gly Thr Val Asn Gly His Cys Phe Lys Cys Ile Gly Lys Gly Glu Gly
                20                  25                  30

Asn Pro Phe Glu Gly Thr Gln Glu Met Lys Ile Glu Val Ile Glu Gly
            35                  40                  45

Gly Pro Leu Pro Phe Ala Phe His Ile Leu Ser Thr Ser Cys Met Tyr
50                  55                  60

Gly Ser Lys Thr Phe Ile Lys Tyr Val Ser Gly Ile Pro Asp Tyr Phe
65                  70                  75                  80

Lys Gln Ser Phe Pro Glu Gly Phe Thr Trp Glu Arg Thr Thr Thr Tyr
                85                  90                  95

Glu Asp Gly Gly Phe Leu Thr Ala His Gln Asp Thr Ser Leu Asp Gly
            100                 105                 110
```

```
Asp Cys Leu Val Tyr Lys Val Lys Ile Leu Gly Asn Asn Phe Pro Ala
            115                 120                 125

Asp Gly Pro Val Met Gln Asn Lys Val Gly Arg Trp Glu Pro Gly Thr
130                 135                 140

Glu Ile Val Tyr Glu Val Asp Gly Val Leu Arg Gly Gln Ser Leu Met
145                 150                 155                 160

Ala Leu Lys Cys Pro Gly Gly Arg His Leu Thr Cys His Leu His Thr
                165                 170                 175

Thr Tyr Arg Ser Lys Lys Pro Ala Ser Ala Leu Lys Met Pro Gly Phe
            180                 185                 190

His Phe Glu Asp His Arg Ile Glu Ile Met Glu Glu Val Glu Lys Gly
            195                 200                 205

Lys Cys Tyr Lys Gln Tyr Glu Ala Ala Val Gly Arg Tyr Cys Asp Ala
210                 215                 220

Ala Pro Ser Lys Leu Gly His Asn
225             230

<210> SEQ ID NO 20
<211> LENGTH: 233
<212> TYPE: PRT
<213> ORGANISM: Renilla reniformis

<400> SEQUENCE: 20

Met Asp Leu Ala Lys Leu Gly Leu Lys Glu Val Met Pro Thr Lys Ile
1               5                   10                  15

Asn Leu Glu Gly Leu Val Gly Asp His Ala Phe Ser Met Glu Gly Val
            20                  25                  30

Gly Glu Gly Asn Ile Leu Glu Gly Thr Gln Glu Val Lys Ile Ser Val
        35                  40                  45

Thr Lys Gly Ala Pro Leu Pro Phe Ala Phe Asp Ile Val Ser Val Ala
50                  55                  60

Phe Ser Tyr Gly Asn Arg Ala Tyr Thr Gly Tyr Pro Glu Glu Ile Ser
65                  70                  75                  80

Asp Tyr Phe Leu Gln Ser Phe Pro Glu Gly Phe Thr Tyr Glu Arg Asn
                85                  90                  95

Ile Arg Tyr Gln Asp Gly Gly Thr Ala Ile Val Lys Ser Asp Ile Ser
            100                 105                 110

Leu Glu Asp Gly Lys Phe Ile Val Asn Val Asp Phe Lys Ala Lys Asp
        115                 120                 125

Leu Arg Arg Met Gly Pro Val Met Gln Gln Asp Ile Val Gly Met Gln
130                 135                 140

Pro Ser Tyr Glu Ser Met Tyr Thr Asn Val Thr Ser Val Ile Gly Glu
145                 150                 155                 160

Cys Ile Ile Ala Phe Lys Leu Gln Thr Gly Lys His Phe Thr Tyr His
                165                 170                 175

Met Arg Thr Val Tyr Lys Ser Lys Lys Pro Val Glu Thr Met Pro Leu
            180                 185                 190

Tyr His Phe Ile Gln His Arg Leu Val Lys Thr Asn Val Asp Thr Ala
        195                 200                 205

Ser Gly Tyr Val Val Gln His Glu Thr Ala Ile Ala Ala His Ser Thr
210                 215                 220

Ile Lys Lys Ile Glu Gly Ser Leu Pro
225                 230
```

<210> SEQ ID NO 21
<211> LENGTH: 222
<212> TYPE: PRT
<213> ORGANISM: Pontellina plumata

<400> SEQUENCE: 21

```
Met Pro Ala Met Lys Ile Glu Cys Arg Ile Thr Gly Thr Leu Asn Gly
1               5                   10                  15

Val Glu Phe Glu Leu Val Gly Gly Glu Gly Thr Pro Glu Gln Gly
            20                  25                  30

Arg Met Thr Asn Lys Met Lys Ser Thr Lys Gly Ala Leu Thr Phe Ser
            35                  40                  45

Pro Tyr Leu Leu Ser His Val Met Gly Tyr Gly Phe Tyr His Phe Gly
        50                  55                  60

Thr Tyr Pro Ser Gly Tyr Glu Asn Pro Phe Leu His Ala Ile Asn Asn
65                  70                  75                  80

Gly Gly Tyr Thr Asn Thr Arg Ile Glu Lys Tyr Glu Asp Gly Gly Val
                85                  90                  95

Leu His Val Ser Phe Ser Tyr Arg Tyr Glu Ala Gly Arg Val Ile Gly
            100                 105                 110

Asp Phe Lys Val Val Gly Thr Gly Phe Pro Glu Asp Ser Val Ile Phe
        115                 120                 125

Thr Asp Lys Ile Ile Arg Ser Asn Ala Thr Val Glu His Leu His Pro
130                 135                 140

Met Gly Asp Asn Val Leu Val Gly Ser Phe Ala Arg Thr Phe Ser Leu
145                 150                 155                 160

Arg Asp Gly Gly Tyr Tyr Ser Phe Val Val Asp Ser His Met His Phe
                165                 170                 175

Lys Ser Ala Ile His Pro Ser Ile Leu Gln Asn Gly Gly Pro Met Phe
            180                 185                 190

Ala Phe Arg Arg Val Glu Glu Leu His Ser Asn Thr Glu Leu Gly Ile
        195                 200                 205

Val Glu Tyr Gln His Ala Phe Lys Thr Pro Ile Ala Phe Ala
    210                 215                 220
```

<210> SEQ ID NO 22
<211> LENGTH: 657
<212> TYPE: DNA
<213> ORGANISM: Branchiostoma floridae

<400> SEQUENCE: 22

```
atgcccctgc cgccacccca cgacatccac ctgcacggca gcatcaacgg ccacgagttc      60
gacatggtgg cggcggcaa gggcgacccc aacgccggca gcctggtgac caccgccaag     120
agcaccaagg gcgccctgaa gttcagcccc tacctgatga tccccacct gggctacggc     180 tactaccagt acctgcccta ccccgacggc cccagcccct ccaggccag catgctggag     240 ggcagcggct acgccgtgta cagggtgttc gacttcgagg acggcggcaa gctgaccacc     300
gagttcaagt acagctacga gggcagccac atcaaggccg acatgaagct gatgggcagc     360
ggcttccccg acgacggccc cgtgatgacc agccagatcg tggaccagga cggctgcgtg     420
agcaagaaga cctacctgaa caacaacacc atcgtggaca gcttcgactg gagctacaac     480
ctgcagaacg gcaagaggta cagggccagg gtgagcagcc actacatctt cgacaagccc     540
ttcagcgccg acctgatgaa gaagcagccc gtgttcgtgt acaggaagtg ccacgtgaag     600
gccagcaaga ccgaggtgac cctggacgag agggagaagg ccttctacga gctggcc        657
```

<210> SEQ ID NO 23
<211> LENGTH: 669
<212> TYPE: DNA
<213> ORGANISM: Branchiostoma floridae

<400> SEQUENCE: 23

```
atgagcctgc ccaccaccca cgacctgcac atcttcggca gcgtgaacgg cgccgagttc      60
gacctggtgg cggcggcaa gggcaacccc aacgacggca ccctggagac cagcgtgaag     120
agcacccgcg gcgccctgcc ctgcagcccc ctgctgatcg gccccaacct gggctacggc     180
ttctaccagt acctgccctt ccccggcggc gccagcccct ccagaccgc catcaccgac     240
ggcggctacc aggtgcaccg cgtgttcaag ttcgaggacg cggcgtgct gagctgcaac     300
ttccgctaca cctacgaggg cggcaagatc aagggcgagt ccagctgat cggcagcggc     360
ttccccgccg gcggccccgt gatgagcggc ggcctgacca ccctggaccg cagcgtggcc     420
aagctgcagt gcagcgacga ctgcaccatc accggcacca caactggag cttctgcacc     480
accgacggca agcgccacca ggccgacgtg cagaccaact acaccttcgc caagcccctg     540
cccgccggcc tgaaggagaa gatgcccatc ttcctgggcc accagatcga ggtgaaggcc     600
agcaagaccg agatcaccct gagcgagaag gtgaaggcct tcatcgacac cgtgggcagc     660
ggtaccgga                                                              669
```

<210> SEQ ID NO 24
<211> LENGTH: 663
<212> TYPE: DNA
<213> ORGANISM: ABranchiostoma floridae

<400> SEQUENCE: 24

```
atgagcgtgc ccaccaacct ggacctgcac atctacggca gcatcaacgg catggagttc      60
gacatggtgg cggcggcag cggcaacccc aaggacggca gcctgagcgt gaacgtgaag     120
agcaccaagg gcgccctgcg cgtgagcccc ctgctggtgg gccccacct gggctacggc     180
cactaccagt acctgccctt ccccgacggc cccagcccct ccaggccgc cgtgaacaac     240
ggcggctacc agatgcaccg cagcttcaac ttcgaggacg cgccgtgct gaccgccacc     300
tacaactaca gctacagcgg cggcaagatc cagggcgagt ccacctggt gggcagctgc     360
ttccccgacg cagcccccgt gatgaccaac gccctgaccg gcctggaccg cagcgtggcc     420
aagctgatgt gcgtgagcga cgacaagctg gccgagttcg tggactggac ctaccgcacc     480
agcagcggcg gccgctaccg cgccaccgtg cagaccaact tcaccttcgc caagcccatc     540
gccgccggcc tgaagaacaa catgcccatg ttcgtgttcc gccagctgga ggtgaccggc     600
agcaagaccg agatcggcct gcaggagcag cagaaggcct tcagcaccgt gctgggtacc     660
gga                                                                    663
```

<210> SEQ ID NO 25
<211> LENGTH: 659
<212> TYPE: DNA
<213> ORGANISM: Branchiostoma floridae

<400> SEQUENCE: 25

```
atgcctctgc ccgcaaccca cgacatccac cttcacggct ccatcaacgg ccacgagttc      60
gacatggtgg ggggaggaaa aggcgacccg aacgccggct cgctggtgac cacagcgaaa     120
tccaccaagg gtgccctgaa gttctctccc tacttgatga tccccaccct cgggtacggg     180
tactaccagt acctcccccta cccggacgga ccctcgcctt ccaggcctc catgttggaa     240
```

```
ggatcggggt atgcagtcta ccgcgtgttc gactttgaag acggaggcaa gctgactacc    300
gagtttaagt actcctacga gggttcccat atcaaggccg acatgaagct gatgggaagc    360
ggtttccctg acgacggccc agtcatgacc agccagattg tcgaccagga cggctgcgtg    420
tccaagaaga cgtatcttaa caacaacacc atcgtggaca gcttcgactg gagttacaac    480
ctgcagaatg ggaagcgcta cagggcccga gtgtcgagcc actacatctt cgacaagccc    540 tttttcagccg atctcatgaa gaagcagccg tcttcgtgt accgaagtgc cacgtgaagg    600
cttccaagac cgaagtcacc ctggacgaga gggagaaggc gttctacgag ctggcttag    659

<210> SEQ ID NO 26
<211> LENGTH: 657
<212> TYPE: DNA
<213> ORGANISM: Branchiostoma floridae

<400> SEQUENCE: 26
atgtctctcc ctacgactca cgaccttcac atcttcggct ccgtcaatgg cgcggagttc     60
gacctggtgg gaggcggaaa gggcaacccg aacgatggaa cgctggagac cagtgtgaaa    120
tccacccggg gcgccctgcc ctgctccccg ctgctgatcg acccaacctg gggtacggc    180 ttctaccagt acctgccctt ccctggcggc gcctcaccct ccaaaccgc catcacggac    240 ggagggtacc aggttcaccg tgtgttcaag tttgaagacg gcggagtgct gagttgcaac    300
ttccgctaca cctacgaggg cggcaagatc aaaggggagt ccagctgat cgggtcaggt    360 ttccccgccg gcggtccgt gatgtccggc ggactgacca ccctggacag gagcgtggcc    420
aaactgcagt gctcggacga ctgcaccatc accggcacta caactggag cttctgcacc    480 accgatggga gcgccacca gcggatgtg cagacgaact acaccttcgc caagccgctc    540
ccggccggtc tcaaggagaa gatgccgatc ttcctggggc accagatcga ggtcaaggcg    600
tccaagaccg agatcaccct gagcgagaaa gtgaaggcct tcatcgacac tgtgtga       657

<210> SEQ ID NO 27
<211> LENGTH: 657
<212> TYPE: DNA
<213> ORGANISM: Branchiostoma floridae

<400> SEQUENCE: 27
atgtctgtcc cgacaaacct cgacttgcac atctatggct ccatcaacgg tatggagttt     60
gacatggtgg gcggtgggag tggcaaccca aaggacggat cgctgagcgt aaacgtgaag    120
tctaccaaag gtgccctgcg cgtttctcct ctgctggtgg gcccgcatct ggggtacggc    180
cactaccagt acctaccctt ccctgacggt ccgtcgcctt ccaggcagc cgtgaacaac    240 ggcgggtatc aaatgcatcg ctcttttcaac ttcgaggacg gtgccgtgct gactgccacc    300
tacaactact cctacagcgg cggcaagatc cagggagagt ttcatctggt gggcagctgt    360
ttccccgacg atagtccggt gatgaccaac gcgctgaccg gtctggacag gagcgtggcc    420
aagctgatgt gcgtgtccga tgacaagctt gccgagttcg tggactggac ctaccgcacc    480
agcagcggcg ggcgctaccg tgccacggtg cagaccaact tcaccttcgc aaagcccatc    540
gcagctggct tgaagaataa catgccgatg ttcgtgttcc gtcagctgga agtcaccggc    600
tccaaaaccg agatcggcct tcaggagcag caaaaggcgt tctccaccgt tctgtga       657

<210> SEQ ID NO 28
<211> LENGTH: 243
<212> TYPE: PRT
```

```
<213> ORGANISM: Artificial
<220> FEATURE:
<223> OTHER INFORMATION: Synthetic Construct

<400> SEQUENCE: 28

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Ser
225                 230                 235                 240

Gly Leu Arg

<210> SEQ ID NO 29
<211> LENGTH: 219
<212> TYPE: PRT
<213> ORGANISM: Branchiostoma floridae
<220> FEATURE:
<221> NAME/KEY: misc_feature
<222> LOCATION: (135)..(135)
<223> OTHER INFORMATION: Xaa can be any naturally occurring amino acid
<220> FEATURE:
<221> NAME/KEY: misc_feature
<222> LOCATION: (172)..(172)
<223> OTHER INFORMATION: Xaa can be any naturally occurring amino acid
<220> FEATURE:
<221> NAME/KEY: misc_feature
<222> LOCATION: (192)..(192)
<223> OTHER INFORMATION: Xaa can be any naturally occurring amino acid

<400> SEQUENCE: 29

Met Pro Leu Pro Ala Thr His Glu Ile His Leu His Gly Ser Ile Asn
1               5                   10                  15

Gly His Glu Phe Asp Leu Ala Gly Gly Gly Lys Gly Asp Pro Asn Ala
            20                  25                  30
```

```
Gly Ser Leu Val Thr Thr Ala Lys Ser Thr Gln Gly Pro Leu Lys Phe
            35                  40                  45

Ser Pro His Leu Met Ile Pro His Leu Gly Tyr Gly Tyr Tyr Gln Tyr
    50                  55                  60

Leu Pro Tyr Pro Asp Gly Pro Ser Pro Phe Gln Ala Thr Met Leu Glu
 65                  70                  75                  80

Gly Ser Gly Tyr Thr Val His Arg Val Phe Asp Phe Glu Asp Gly Gly
                85                  90                  95

Lys Leu Ser Ile Glu Phe Lys Tyr Ser Tyr Glu Gly Ser His Ile Lys
            100                 105                 110

Ala Asp Met Lys Phe Thr Gly Thr Gly Phe Pro Glu Asp Gly Pro Val
            115                 120                 125

Met Thr Ser Gln Ile Val Xaa Gln Asp Gly Cys Val Ser Lys Asn Thr
            130                 135                 140

Tyr Leu Asn Asp Asn Thr Ile Val Asp Asn Phe Asp Trp Thr Tyr Asn
145                 150                 155                 160

Leu Gln Asn Gly Lys Arg Tyr Arg Ala Arg Val Xaa Ser His Tyr Ile
                165                 170                 175

Phe Asp Lys Pro Phe Ser Ala Asp Leu Met Lys Lys Gln Pro Val Xaa
            180                 185                 190

Val Tyr Arg Lys Cys Tyr Val Lys Ala Thr Lys Thr Glu Ile Asn Leu
            195                 200                 205

Asp Glu Arg Glu Lys Ala Phe Tyr Glu Leu Ala
            210                 215

<210> SEQ ID NO 30
<211> LENGTH: 219
<212> TYPE: PRT
<213> ORGANISM: Branchiostoma floridae
<220> FEATURE:
<221> NAME/KEY: misc_feature
<222> LOCATION: (178)..(178)
<223> OTHER INFORMATION: Xaa can be any naturally occurring amino acid
<220> FEATURE:
<221> NAME/KEY: misc_feature
<222> LOCATION: (182)..(182)
<223> OTHER INFORMATION: Xaa can be any naturally occurring amino acid

<400> SEQUENCE: 30

Met Pro Leu Pro Ala Thr His Asp Ile His Leu His Gly Ser Ile Asn
  1               5                  10                  15

Gly His Glu Phe Asp Met Val Gly Gly Lys Gly Asp Pro Asn Ala
                20                  25                  30

Gly Ser Leu Val Thr Thr Ala Lys Ser Thr Lys Gly Pro Leu Lys Phe
            35                  40                  45

Ser Pro Tyr Leu Met Ile Pro His Leu Gly Tyr Gly Tyr Tyr Gln Tyr
    50                  55                  60

Leu Pro Tyr Pro Asp Gly Pro Ser Pro Phe Gln Ala Thr Met Leu Glu
 65                  70                  75                  80

Gly Ser Gly Tyr Ala Val His Arg Val Phe Asp Phe Glu Asp Gly Gly
                85                  90                  95

Lys Leu Ser Ile Glu Phe Lys Tyr Ser Tyr Glu Gly Ser His Ile Lys
            100                 105                 110

Ala Asp Met Lys Phe Thr Gly Thr Gly Phe Pro Glu Asp Gly Pro Val
            115                 120                 125

Met Thr Ser Gln Ile Val Asp Gln Asp Gly Cys Val Ser Lys Asn Thr
            130                 135                 140
```

Tyr Leu Asn Asp Asn Thr Ile Val Asp Ser Phe Asp Trp Thr Tyr Asn
145                 150                 155                 160

Leu Gln Asn Gly Lys Arg Tyr Arg Ala Arg Val Thr Ser His Tyr Ile
            165                 170                 175

Phe Xaa Lys Pro Phe Xaa Ala Asp Leu Met Lys Lys Gln Pro Val Phe
        180                 185                 190

Val Tyr Arg Lys Cys His Val Lys Ala Ser Lys Thr Glu Val Thr Leu
        195                 200                 205

Asp Glu Arg Glu Lys Ala Phe Tyr Glu Leu Ala
        210                 215

<210> SEQ ID NO 31
<211> LENGTH: 218
<212> TYPE: PRT
<213> ORGANISM: Branchiostoma floridae

<400> SEQUENCE: 31

Met Ser Leu Pro Thr Thr His Asp Leu His Ile Phe Gly Ser Val Asn
1               5                   10                  15

Gly Ala Glu Phe Asp Leu Val Gly Gly Lys Gly Asn Pro Asn Asp
            20                  25                  30

Gly Thr Leu Glu Thr Ser Val Lys Ser Thr Arg Gly Ala Leu Pro Cys
        35                  40                  45

Ser Pro Leu Leu Ile Gly Pro Asn Leu Gly Tyr Gly Phe Tyr Gln Tyr
50                  55                  60

Leu Pro Phe Pro Gly Gly Ala Ser Pro Phe Gln Thr Ala Ile Thr Asp
65                  70                  75                  80

Gly Gly Tyr Gln Val His Arg Val Phe Lys Phe Glu Asp Gly Gly Val
            85                  90                  95

Leu Asn Cys Asn Phe Arg Tyr Thr Tyr Glu Gly Gly Lys Ile Lys Gly
        100                 105                 110

Glu Phe Gln Leu Leu Gly Ser Gly Phe Pro Ala Gly Gly Pro Val Met
        115                 120                 125

Ser Gly Gly Leu Thr Thr Leu Asp Arg Ser Val Ala Lys Leu Gln Cys
130                 135                 140

Ser Asp Asp Cys Thr Ile Thr Gly Thr Asn Asn Trp Ser Phe Cys Thr
145                 150                 155                 160

Thr Asp Gly Lys Arg His Gln Ala Asp Val Gln Thr Asn Tyr Thr Phe
            165                 170                 175

Ala Lys Pro Leu Pro Ala Gly Leu Lys Glu Lys Met Pro Val Phe Leu
        180                 185                 190

Gly His Gln Ile Glu Val Lys Ala Ser Lys Thr Glu Ile Asn Leu Ser
        195                 200                 205

Glu Lys Val Lys Ala Phe Ile Asp Thr Val
        210                 215

<210> SEQ ID NO 32
<211> LENGTH: 9
<212> TYPE: PRT
<213> ORGANISM: Artificial
<220> FEATURE:
<223> OTHER INFORMATION: "Linker" refers to a peptide or polypeptide
      linker sequence

<400> SEQUENCE: 32

Arg Ala Arg Asp Pro Arg Val Ala Thr
1               5

<210> SEQ ID NO 33
<211> LENGTH: 996
<212> TYPE: DNA
<213> ORGANISM: Branchiostoma floridae
<220> FEATURE:
<221> NAME/KEY: misc_feature
<222> LOCATION: (927)..(927)
<223> OTHER INFORMATION: n is a, c, g, or t
<220> FEATURE:
<221> NAME/KEY: misc_feature
<222> LOCATION: (968)..(968)
<223> OTHER INFORMATION: n is a, c, g, or t

<400> SEQUENCE: 33

| | | |
|---|---|---|
| ccgagttcat acgagaccaa caaagatccg cgcaaccatg cctctgccag caactcacga | 60 |
| gatccacctc cacggttcca tcaacggcca cgagttcgac ctggctggtg gtggaaaagg | 120 |
| cgacccaaac gccggctcgc tggtgaccac agcgaaatcc acccagggtc ccctgaagtt | 180 |
| ctctccccac ttgatgatcc cccacctcgg gtacgggtac taccagtacc tcccctaccc | 240 |
| ggacggaccc tcgcctttcc aggccaccat gttggaagga tcggggtata cagtccaccg | 300 |
| cgtgtrtgac ttcgaagacg gaggcaagct gtccatcgag ttcaagtacr cctacgaggg | 360 |
| ttcccatatt aaggccgaca tgaagttcac gggaaccggt ttccctgagg atgggccggt | 420 |
| catgaccagc cagattgtcg acaggacggc tgcgrgtcca agaacaccta cctcaacgac | 480 |
| aacaccatcg tggacaactt cgactggact tacaacctgc agaagggaag cgctacaggg | 540 |
| cccgagtgcg agccactaca tcttcgacaa gcccttttca gccgatctca tgaagaagca | 600 |
| gccggtctcg ttaccgcaag tgctacgtga aggctaccaa gaccgagatc aacctcgacg | 660 |
| agagggagaa ggcgttctat gagctggctt aggcaacata tcaggtcatt ctccaagcag | 720 |
| atgttgggca gaaaatcgtc cacaaggttg acagttcccc cgtttaatag tagccatgct | 780 |
| tggttagtac ataacagtat cattatatac caaccatgca tgtgggtcgg ggggtaggta | 840 |
| ctatcggtaa agcttacttt tctcaacatc tgcttggcaa gattcctgta tggtcgtctt | 900 |
| aggtcggctt gaaacagact gcgggananatt cctccatggc aggcttttttg actgggcttt | 960 |
| ttcaacanaa acgtacgact tcagactatt gggaac | 996 |

<210> SEQ ID NO 34
<211> LENGTH: 1081
<212> TYPE: DNA
<213> ORGANISM: Branchiostoma floridae

<400> SEQUENCE: 34

| | | |
|---|---|---|
| tgtcttcccg agttcatccg agaccagcaa agatccgcgc aaccatgcct ctgcccgcaa | 60 |
| cccacgacat ccacctcacg gctccatcaa cggccacgag ttcgacatgg tggggggagga | 120 |
| aaaggcgacc cgaacgccgg ctcgctggtg accacagcga atccaccaa gggtcccctg | 180 |
| aagttctctc cctacttgat gatccccac ctcgggtacg ggtactacca gtacctcccc | 240 |
| tacccggacg gaccctcgcc tttccaggcc accatgttgg aaggatcggg gtatgcagtc | 300 |
| caccgcgtgt ttgacttcga agacggaggc aagctgtcca tcgagtttaa gtactcctac | 360 |
| gagggttccc atattaaggc cgacatgaag ttcacgggaa ccggtttccc tgaggacggg | 420 |
| ccggtcatga ccagccagat tgtcgaccag gacggctgcg tgtccaagaa cacctacctt | 480 |
| aacgacaaca ccatcgtgga cagcttcgac tggacttaca acctgcagaa tgggaagcgc | 540 |
| tacagggccc gagtgacgag ccactacatc ttcgcaagcc ctttcagccg atctcatgaa | 600 |
| gaagcagccg gtcttcgtgt accgcaagtg ccacgtgaag gcttccaaga ccgaagtcac | 660 |

```
cctggacgag agggagaagg cgttctacga gctggcttag gcaacaratc aggtcattct    720
ccaagcagat gttgggcaga aaarcgtcca gaaggttgac agttcccccgt tagtaccccat  780
gcttggttag tacataacag tatcattata taccaaccat gcatgtgggt cggggggtag    840
gtactgtcgg taaagctttc ttttctcaac atctgcttgg aaagattcct gtatggtcgt    900
cttagatagg cttgaaacag cctgcggcaa attcctccat ggcaggcttt ttgatgggct    960
tttcaacaaa aacgtacgac ttcagactat tggaaccagt acagtcagta agacacacga   1020
tcagaaacaa gacatgatat tctgagaaag ccagacaaaa agcctctatg gcggctactg   1080
c                                                                   1081
```

<210> SEQ ID NO 35
<211> LENGTH: 825
<212> TYPE: DNA
<213> ORGANISM: Branchiostoma floridae
<220> FEATURE:
<221> NAME/KEY: misc_feature
<222> LOCATION: (811)..(811)
<223> OTHER INFORMATION: n is a, c, g, or t

<400> SEQUENCE: 35

```
aagctgtctt cccgagttca tccgagacca gcaaagatcc gcgcaaccat gtctctccct     60
acgactcacg accttcacat cttcggctcc gtcaatggcg cggagttcga cctggtggga   120
ggcggaaagg gcaacccgaa cgatggaacg ctggagacca gtgtgaaatc caccccgggc   180
gccctgccct gctccccgct gctgatcgga cccaacctgg ggtacggctt ctaccagtac   240
ctgcccttcc ctggcggcgc ctcgcccttc caaaccgcca tcacggacgg agggtaccag   300
gttcaccgtg tgttcaagtt tgaagacggc ggtgtgctga attgcaactt ccgctacacc   360
tacgagggcg gcaagatcaa aggggagttc cagctgctcg ggtcaggttt ccctgccggc   420
ggtcctgtga tgtccggcgg actgaccacc ctggacagga gcgtggccaa actgcagtgc   480
tcggacgact gcaccatcac cggcactaac aactggagct tctgcaccac cgatgggaag   540
cgccaccagg cggatgtgca gacgaactac accttcgcca agccgctccc ggccggtctc   600
aaggagaaga tgccggtctt cctggggcac cagatcgagg tcaaggcgtc caagaccgag   660
atcaacctga gcgagaaagt gaaggccttc atcgacactg tgtgaagttc aagttactat    720
agccgactgt gttaagccca gatccagtcc tgttacatgt atcactataa accctaaggt    780
tctgctggcg gctactgcaa caaaagcgta ntcattactt cttat                    825
```

<210> SEQ ID NO 36
<211> LENGTH: 4
<212> TYPE: PRT
<213> ORGANISM: Branchiostoma floridae

<400> SEQUENCE: 36

Leu Gly Tyr Gly
1

<210> SEQ ID NO 37
<211> LENGTH: 669
<212> TYPE: DNA
<213> ORGANISM: Branchiostoma floridae

<400> SEQUENCE: 37

```
atgagcctgc ccaccaccca cgacctgcac atcttcggca cgtgaacgg cgccgagttc      60
gacctggtgg gcggcggcat gggcaacccc aacgacggca ccctggagac cagcgtgaag   120
```

```
agcacccgcg gcgctctgcc ctgcagcccc ctgctgatcg gccccaacct gggctacggc    180
ttctaccagt acctgccctt ccccggcggc gccagcccct tccagaccgc catcaccgac    240
ggcggctacc aggtgcaccg cgtgttcaag ttcgaggacg gcggcgtgct gagctgcaac    300
ttccgctaca cctacgaggg cggcaagatc aagggcgagt ccagctgat cggcagcggc     360 ttccccgccg gcgccccgt gatgagcggc ggcctgacca ccctggaccg cagcgtggcc     420
aagctgcagt gcagcgacga ctgcaccatc accggcacca acaactggag cttctgcacc    480
accgacggca gcgccacca ggccgacgtg cagaccaact acaccttcgc caagcccctg     540
cccgccggcc tgaaggagaa gatgcccatc ttcctgggcc accagatcga ggtgaaggcc    600
agcaagaccg agatcaccct gagcgagaag gtgaaggcct tcatcgacac cgtgggcagc    660
ggtaccgga                                                            669
```

```
<210> SEQ ID NO 38
<211> LENGTH: 216
<212> TYPE: PRT
<213> ORGANISM: Branchiostoma floridae

<400> SEQUENCE: 38

Met Ser Leu Pro Thr Thr His Asp Leu His Ile Phe Gly Ser Val Asn
1               5                   10                  15

Gly Ala Glu Phe Asp Leu Val Gly Gly Met Gly Asn Pro Asn Asp
                20                  25                  30

Gly Thr Leu Glu Thr Ser Val Lys Ser Thr Arg Gly Ala Leu Pro Cys
            35                  40                  45

Ser Pro Leu Leu Ile Gly Pro Asn Leu Gly Tyr Gly Phe Tyr Gln Tyr
        50                  55                  60

Leu Pro Phe Pro Gly Gly Ala Ser Pro Phe Gln Thr Ala Ile Thr Asp
65                  70                  75                  80

Gly Gly Tyr Gln Val His Arg Val Phe Lys Phe Glu Asp Gly Gly Val
                85                  90                  95

Leu Ser Cys Asn Phe Arg Tyr Thr Tyr Glu Gly Gly Lys Ile Lys Gly
            100                 105                 110

Glu Phe Gln Leu Ile Gly Ser Gly Phe Pro Ala Gly Gly Pro Val Met
        115                 120                 125

Ser Gly Gly Leu Thr Thr Leu Asp Arg Ser Val Ala Lys Leu Gln Cys
130                 135                 140

Ser Asp Asp Cys Thr Ile Thr Gly Thr Asn Asn Trp Ser Phe Cys Thr
145                 150                 155                 160

Thr Asp Gly Lys Arg His Gln Ala Asp Val Gln Thr Asn Tyr Thr Phe
                165                 170                 175

Ala Lys Pro Leu Pro Ala Gly Leu Lys Glu Lys Met Pro Ile Phe Leu
            180                 185                 190

Gly His Gln Ile Glu Val Lys Ala Ser Lys Thr Glu Ile Thr Leu Ser
        195                 200                 205

Glu Lys Val Lys Ala Phe Ile Asp
210                 215
```

BRANCHIOSTOMA DERIVED FLUORESCENT PROTEINS

CROSS-REFERENCE TO RELATED APPLICATIONS

This application is a divisional application of and claims benefit to U.S. patent application Ser. No. 12/311,076, filed Mar. 18, 2009. The '076 application is the U.S. National Stage of International Application No. PCT/US2007/079333, filed Sep. 24, 2007, which claims priority to U.S. Provisional Application No. 60/826,735, filed Sep. 22, 2006 and U.S. Provisional Application No. 60/891,886, filed Feb. 27, 2007.

INCORPORATION BY REFERENCE OF SEQUENCE LISTING

This application contains references to amino acids and/or nucleic acid sequences that have been filed concurrently herewith as sequence listing text file "0361706.txt", file size of 65 KB, created on Feb. 3, 2014. The aforementioned sequence listing is hereby incorporated by reference in its entirety pursuant to 37 C.F.R. §1.52(e)(5).

BACKGROUND OF INVENTION

A. Field of the Invention

The present invention relates to novel fluorescent proteins and nucleic acid sequences derived from the genus *Branchiostoma*. Specifically, the invention includes fluorescent protein compositions, methods of use, and transgenic organisms encompassing the fluorescent proteins.

B. Description of Related Art

Fluorescent proteins are used extensively as markers in many biotechnological applications. These proteins become spontaneously fluorescent due to autocatalytic chromophore generation and have been found in several aquatic species including jellyfish, coral, and sea pansies. The first fluorescent protein to be used as a research tool was green fluorescent protein (GFP), initially isolated from *Aequorea victoria* (jellyfish). Since the initial discovery of GFP, numerous fluorescent proteins have been generated by either altering the sequence of GFP or isolation from other bioluminescent species.

The crystal structure of GFP (Ormo, M. et al., Science 273: 1392-1395, 1996) combined with mutation experiments (Li, S., et al., J Biol. Chem. 272(45): 28545-28549, 1997) have elucidated the essential domains required for the fluorescent activity of GFP. The chromophore of GFP is the result of spontaneous cyclization and oxidation of the amino acids Ser65/Thr65, Tyr66, and Gly67. Based on the crystal structure, the GFP protein structure consists of an 11-stranded beta barrel with a coaxial helix, collectively termed the β-can, in which the chromophore forms from the central helix (Ormo, M. et al., Science 273: 1392-1395, 1996). While most fluorescent proteins identified to date share the same 1.3-can polypeptide fold, substantial differences in the chromophore structure do exist (Labas, Y. A. et al., PNAS 99(7) 4256-4261, Apr. 2, 2002).

Inherent coding underlies many limitations encountered in the use of common fluorescent proteins. Despite extensive use, the expression of fluorescent proteins in mammalian cells is highly variable at best, often requiring a strong promoter and decreased incubation temperature (Ogawa, H., et al., Proc. Natl. Acad. Sci. 92: 11899-11903, 1995). Fluorescent proteins exhibit a slow maturation rate and decreased expression efficiency in non-homologous cells, including mammalian cells. To enhance fluorescent proteins used in mammalian cells, attempts have been made to harmonize, or humanize, fluorescent proteins by replacing one or more species-specific codons with codons more frequently used in human genes to produce specific amino acids (U.S. Patent Application No. 2005/0014223A1, filed: Apr. 1, 2004; U.S. Patent Application No. 005968750A, filed: Oct. 9, 1998; Yang, T., et al., Nucleic Acids Research 24(22): 4592-4593). Harmonizing fluorescent proteins improves translation efficiency and maturation rate in host cells, resulting in better expression and brighter fluorescence. Further optimization of fluorescent protein coding sequences by modifying specific amino acids may result in altered folding properties, shifted excitation/emission spectra, and altered incubation temperature sensitivity (Nagai, T. et al., Nature Biotechnology 20(1): 87-90, January, 2002).

While fluorescent proteins are useful, the use is limited by incompatible species differences. Fluorescent proteins are not expressed or well-folded at temperatures suitable for growing mammalian cells (typically about 37° C.). Modifying the amino acid sequence of GFP has produced derivatives with enhanced fluorescence in non-homologous cells at incubation temperatures above 30° C. (U.S. Patent Application No. 2004/0138420A1, filed: Jan. 14, 2005). Furthermore, amino acid substitutions corresponding to F64, either S65 or E222, and/or 5175 has increased fluorescence detection in mammalian cells at lower levels of GFP expression. Nevertheless, despite numerous attempts at optimizing existing fluorescent proteins for use in mammalian cells, the use of fluorescent proteins in mammalian cells is still limited due to the inability to fully overcome these drawbacks. The fluorescent proteins of the present invention inherently possess characteristics that overcome the limitations and drawbacks faced using available fluorescent proteins of the art.

SUMMARY OF INVENTION

In the present invention, novel fluorescent proteins (LanFPs) derived from *Branchiostoma floridae*, Lancelet, are disclosed. The invention includes nucleic acid and amino acid sequences encoding fluorescent proteins derived from *Branchiostoma* species and compositions, combinations, methods, and kits for the use thereof. Previously, fluorescent proteins from *Branchiostoma* were believed to be unknown. Since the Lancelet is phylogenetically close in relation to vertebrates, LanFPs have inherent characteristics that known fluorescent proteins, derived from other less closely related organisms, have been optimized to gain. For example, unlike the fluorescent proteins in the art, fluorescent proteins derived from Lancelet fluoresce efficiently at temperatures optimal for mammalian cells. These novel fluorescent proteins provide an alternative to the existing fluorescent proteins for use with mammalian cells.

The fluorescent proteins of the invention include amino acid coding sequences of SEQ ID NO: 1 (LanFP1), SEQ ID NO: 2 (LanFP2), SEQ ID NO: 3 (LanFP3), SEQ ID NO: 29 (LanFP4), SEQ ID NO: 30 (LanFP5), SEQ ID NO: 31 (LanFP6), and SEQ ID NO: 38 (mutant of LanFP2). The isolated *Branchiostoma* fluorescent proteins of the invention, or LanFPs, are characterized by emitting fluorescence at a higher intensity than GFP. LanFPs exhibit at least two, three, five, seven, or more times greater cellular fluorescence than GFP under normal conditions in a cell, including the GFPs encoded by SEQ ID NO: 4 and SEQ ID NO: 28.

Further the LanFPs are characterized as having a chromophore region at amino acid positions 56-61 of SEQ ID NO: 1 (LanFP1), SEQ ID NO: 2 (LanFP2), SEQ ID NO: 3

(LanFP3), SEQ ID NO: 29 (LanFP4), SEQ ID NO: 30 (LanFP5), SEQ ID NO: 31 (LanFP6), and SEQ ID NO: 38 (mutant of LanFP2). This chromophore region is similar to, but distinct from, the chromophore region of GFP, with the two compared in FIG. 12. The LanFP chromophore includes amino acid residues LGYG (SEQ ID NO: 36) and may minimally include the residues GYG. This LanFP chromophore region may be flanked by leucine, histidine, asparagine, tyrosine, phenylalanine, combinations thereof, or by other amino acids that have similar charges and tertiary folding characteristics. The chromophore region may be altered by mutation or harmonization to optimize its function in a host cell or organism. "Optimization", or "to optimize" means altering the protein to enhance expression level, maturation rate, emission spectrum, color, length of expression, or any combination thereof.

The amino acid sequences encoding *Branchiostoma* fluorescent polypeptides have at least about 50%, 55%, 60%, 65%, 70%, 75%, 80%, 85%, 90%, 91%, 92%, 93%, 94%, 95%, 96%, 97%, 99% or greater sequence identity to SEQ ID NOs: 1-3 or SEQ ID NOs: 29-31. Further, the amino acid sequence encoding an isolated *Branchiostoma* fluorescent protein encodes a chromophore region including the amino acid residues LGYG (SEQ ID NO: 36) and has at least 60%, 65%, 70%, 75%, 80%, 85%. 90%, 95%, or more identity to SEQ ID NOs: 1-3, 29-31, or 38. Preferably, the amino acid sequence encoding an isolated *Branchiostoma* fluorescent protein encodes a chromophore region including the amino acid residues GYG and has at least 60%, 65%, 70%, 75%, 80%, 85%, 90%, 95%, or more identity to SEQ ID NOs: 1-3, 29-31, or 38. More preferably, the amino acid sequence encoding an isolated *Branchiostoma* fluorescent protein encodes a chromophore region including at least one of the amino acid residues G. Y, or G and has at least 60%, 65%, 70%, 75%, 80%, 85%, 90%, 95%, or more identity to SEQ ID NOs: 1-3, 29-31, or 38.

The amino acid sequence encoding a LanFP may be modified such that the protein remains capable of fluorescence. Modifications include amino acid substitutions or deletions at positions that do not alter protein function, but may alter excitation or emission spectral properties. As an example, an amino acid may be modified at positions 44, 57, 58, 59, 60, 61, 147, 157, 167, 177, or 201, relative to the starting ATG codon of each LanFP, in SEQ ID NOs: 1-3, 29-31, or 38. Modifications at positions 57, 58, 59, 60, or 61 may alter the spectral properties of the LanFP, while modifications at positions 44, 147, 157, 167, 177, or 201 may enhance the inherent properties without altering protein function.

Herein, the *Branchiostoma* fluorescent proteins, or their respective coding sequences, are collectively referred to as "LanFPs". It will be understood that "LanFPs" encompasses the proteins LanFP1, LanFP2, LanFP3, LanFP4, LanFP5, and LanFP6 and when referring to their respective coding sequences is inclusive of SEQ ID NOs: 1-3, 22-27, 29-31, 33-35, and their complementary sequences.

The polypeptides, or fluorescent proteins, provided by the invention are encoded by the nucleic acid sequences of SEQ ID NOs: 22 (LanFP1) and 25 (native LanFP1), SEQ ID NOs: 23 (LanFP2) and 26 (native LanFP2), SEQ ID NOs: 24 (LanFP3) and 27 (native LanFP3), SEQ ID NO: 33 (LanFP4), SEQ ID NO: 34 (LanFP5), SEQ ID NO: 35 (LanFP6), and SEQ ID NO: 38 (mutant LanFP2) respectively. LanFPs may also be encoded by nucleic acid sequences that hybridize under high stringency conditions to SEQ ID NO: 25, SEQ ID NO: 26, SEQ ID NO: 27, SEQ ID NO: 33, SEQ ID NO: 34, SEQ ID NO: 35, or SEQ ID NO: 37. It is anticipated that high stringent conditions, many of which are known in the art, will be such that nucleic acid sequences at least about 65%, 70%, 75%, 80%, 85%, 90%, 91%, 92%, 93%, 94%, 95%, 96%, 97%, 98%, or 99% homologous to each other typically remain hybridized to each other. For example, under high stringency conditions SEQ ID NO: 22 will hybridize to SEQ ID NO; 25; SEQ ID NO: 23 will hybridize to either SEQ ID NO: 26 or 37; and SEQ ID NO: 24 will hybridize to SEQ ID NO: 27. The invention also provides nucleic acid sequence encoding the polypeptide of SEQ ID NO: 2 by a nucleic acid sequence that includes at least one nucleotide substitution as compared with SEQ ID NO: 26. For example, as compared to SEQ ID NO: 26, SEQ ID NO: 37 include two mutations: A80T and C135T. The first mutation, A80T, results in an amino acid change from lysine to methionine. The second mutation, C135T, is a silent mutation, i.e. the encoded amino acid remains alanine. The resulting mutant. LanFP (see SEQ ID NO: 38), encoded by SEQ ID NO: 37, differs from native LanFP encoded by SEQ ID NO: 2 at position 27 (Lys→Met), yet both mutant and native LanFP2 exhibits similar fluorescence.

The invention includes harmonized nucleic acid sequences. Harmonizing refers to altering the nucleotide codons encoding specific amino acids to those more likely to be used in the host cell or organism without altering the encoded amino acid. Exemplary harmonized sequences include those of SEQ ID NO: 22 (harmonized LanFP1), SEQ ID NO: 23 (harmonized LanFP2), or SEQ ID NO: 24 (harmonized LanFP3), which encode the subject proteins of SEQ ID NO: 1, SEQ ID NO: 2, SEQ ID NO: 3, respectively. The listed sequences are harmonized for expression in mammalian and human cell expression systems. A skilled artisan will recognize that codons of the provided nucleic acid sequence may also be harmonized for expression in any species for which preferred codons have been identified. Exemplary hosts include, but not limited to, bacteria, yeast, fungus, plants, insects, fish, reptiles and other animals.

The sequences provided by the invention may be operatively linked to suitable expression control sequences comprising a vector, or plasmid, for introduction and expression in a host cell or organism. A suitable vector, or plasmid, includes those with the appropriate expression machinery such as, but not limited to, a promoter, polyadenylation sequence, and restriction enzyme sites. Such vectors include standard expression vectors well known in the art. A skilled artisan will recognize that the expression vector or plasmid used will depend upon the host cell or organism with which the expression vector will be used and the intended use of the subject protein. One skilled in the art will also recognize that combinations of more than one subject protein within a single expression vector or individual expression vectors may be used.

The sequences provided by the invention may also be included in an expression cassette. A suitable expression cassette contains at least a transcriptional initiation region functional in an expression host, at least one subject protein, and a transcriptional termination region functional in the expression host. The expression cassette may be contained within a vector or plasmid and may exist in a cell or progeny of a cell as an extrachromosomal element or integrated in the genome of a host cell following introduction into the host cell. A host cell may be isolated, for example in an in vitro culture, or it may be part of a population of cells that is located in an in vitro system or in vivo in a tissue, bodily fluid, organ, or whole organism.

Sequences that are contained within a vector, plasmid or expression cassette can be transformed or transfected into a host cell selected from the group consisting of mammalian, bacteria, yeast, fungus, plant, avian, reptilian, insect, fish, amphibian, and human cell. Exemplary host cells include, but are not limited to, cells from mice, rats, primates, humans, ungulates, lagomorphs, zebrafish, insects, *Drosophila*, amphibians, *Xenopus*, reptiles, yeast, *S. cerevisiae, S. pombe*, orchid, bacteria, and *E. coli*, A skilled artisan will recognize that after introducing the vector, plasmid or expression cassette provided, the introduced DNA may exist extrachromosomally or be integrated into the genome of the host cell.

LanFPs may be used in a fusion protein to tag a molecule of interest, such as a protein. To produce a fusion protein, a LanFP coding sequence may be operably linked to a nucleotide sequence encoding a protein of interest by using molecular cloning methods known in the art. A skilled artisan will recognize that the fusion of a tag to the N- or C.-terminus of a protein may sterically hinder proper folding or functionality of the protein of interest. As such, the placement of the LanFP as a tag may need to be optimized for an individual protein of interest.

The invention provides a recombinant fusion polypeptide comprising a first polypeptide bonded to a second polypeptide. Exemplary first and second polypeptides are found in nature as monomers of multimeric proteins that fluoresce when exposed to light of an excitation wavelength or when interactive with an excited donor fluorophore. Here, the first and second polypeptides of the recombinant fusion polypeptide are not fluorescent donor and acceptor to each other, but do fluoresce when excited. The first and second polypeptides are peptide bonded to each other via a linker sequence. Exemplary linker sequences are 5 to 50 amino acids in length and include, but are not limited to, SEQ ID NO: 32.

One or both of the first and second polypeptides described above may be a monomer of a LanFP, that is, a *Branchiostoma floridae* FP; alternatively, either the first or second polypeptide may be a monomer of a LanFP combined with a *Renilla reniformis* GFP, *Renilla mulleri* GFP, *Aequorea victoria* GFP, other multimeric fluorescent protein, or their variant.

The provided recombinant fusion polypeptide may further comprise a third polypeptide. The third polypeptide can be peptide bonded to the N-terminus of the first polypeptide or C-terminus of the second polypeptide of the recombinant fusion polypeptide either directly or through a peptide linker sequence. The third polypeptide may be a member of a specific binding pair. A specific binding pair refers to a pair of polypeptides that physically interact in a specific manner that gives rise to a biological activity to the substantial exclusion of other polypeptides. Members of a specific binding pair interact through complementary interaction domains. Exemplary specific binding pair members include, but are not limited to, antibody-antigen pairs, enzyme-substrate pairs, dimeric transcription factors, and receptor-ligand pairs.

LanFPs may also be used as reporters of promoter activation. A nucleic acid sequence of SEQ ID NO: 22, SEQ ID NO: 23, SEQ ID NO: 24, SEQ ID NO: 25, SEQ ID NO: 26, SEQ ID NO: 27, SEQ ID NO: 33, SEQ ID NO: 34, or SEQ ID NO: 35, or SEQ ID NO: 37, or homologs or variants thereof, can be positioned under the transcriptional control of a promoter. For example, a LanFP coding sequence can be operably linked to a nucleotide sequence encoding a promoter of interest by molecular cloning methods known in the art. The expression pattern of a gene can be determined by placing a LanFP downstream of the promoter of that gene. The transcriptional activation of the gene will result in the expression of the LanFP, therefore providing localization, as well as, expression intensity information for the gene. Suitable promoters include those found in prokaryotic and eukaryotic organisms, specifically including bacterial and mammalian species. One skilled in the art will recognize that LanFPs can be used in vitro or in vivo to determine the expression pattern of a promoter of interest.

The present invention provides a method of monitoring the interaction of two POIs, the method comprising the steps of: a) contacting a fluorescent polypeptide fusion protein and a second polypeptide wherein: 1) the fluorescent polypeptide fusion protein is the recombinant fusion polypeptide described above with a first, second and third polypeptides peptide bonded, and the third polypeptide is a first POI; ii) the second polypeptide of interest comprises a second POI that is fluorescently labeled; and iii) the fluorophores comprised by the fluorescent polypeptide fusion and the second POI are fluorescent donor and fluorescent acceptor to each other; b) exciting the donor fluorophore; and c) detecting fluorescent emission from the fluorescent acceptor, wherein the emission is indicative of the interaction of the first and the second polypeptides of interest. The contacting step may be performed in vitro or in a cell. Additionally, the contacting step may also consist of introducing a nucleic acid sequence encoding the fluorescent polypeptide fusion protein and the second polypeptide of interest into the cell. Alternatively, the fluorescent polypeptide fusion protein can instead be a first POI fused to a monomeric LanFP.

A method of screening for a compound that modulates the interaction of a first and a second member of a specific binding pair is provided. The method comprises a) contacting a first polypeptide and a second polypeptide in the presence and absence of a candidate modulator wherein: i) the first polypeptide is a fluorescent polypeptide fusion protein, as described above, wherein the third polypeptide is the first member of a specific binding pair; ii) the second polypeptide is fluorescently labeled with a *Branchiostoma* fluorescent polypeptide and comprises the second member of a specific binding pair; and iii) the fluorophores comprised by the first and second polypeptides are fluorescent donor and acceptor to each other; b) exciting the donor fluorophore; and c) detecting the fluorescence of the acceptor fluorophore, such that emission of the spectrum characteristic of the fluorescent acceptor indicates interaction of the first and second members of the specific binding pair, and wherein a change in their interaction in the presence of the candidate modulator indicates that the candidate modulator modulates the interaction of the members of the specific binding pair. Alternatively, the fluorescent polypeptide fusion protein can be a first member of the binding pair fused to a monomeric LanFP.

A transgenic organism, such as a mouse, comprising a LanFP is also provided. The transgenic organism contains at least one LanFP and is suitable for in vivo characterization of LanFP tagged proteins, LanFP reporters of promoters, and identifying LanFP labeled cells within a population of cells among other uses, The skilled artisan will recognize that such transgenic organisms will have a wide variety of uses. Transgenic organisms of the invention will express a LanFP having at least 50%, 55%, 60%, 65%, 70%, 75%, 80%, 85%, 90%, 91%, 92%, 93%, 94%, 95%, 96%, 97%, 98%, 99%, or 100% identity to SEQ ID NOs: 1-3, or SEQ ID NOs: 29-31, or a fluorescent protein encoded by a nucleic acid sequence having at least 50%, 55%, 60%, 65%, 70%, 75%, 80%, 85%. 90%, 91%, 92%, 93%, 94%, 95%, 96%, 97%, 98%, 99%, or 100% homology to any of SEQ ID NOs: 22-27 or 37. or a sequence that hybridizes under high stringency conditions to any of SEQ ID NOs: 25-27 or 37 and includes at least one nucleotide difference from SEQ ID NO: 26 within the hybridized region. The organism may be a mammal, bacteria, yeast, bird, reptile, insect, fish, plant, or amphibian. Exemplary organisms include, but are not limited to mice, rats, non-human primates, swine, cattle, sheep, horses, goats, ungulates, lagomorphs, rodents, worms, fish, zebrafish, *Drosophila, Xenopus, S. cerevisiae, S. pombe*, and *E. coli*.

The present invention provides transgenic plants that express a nucleic acid encoding a LanFP. The nucleic acid will encode a polypeptide having at least 50%, 55%, 60%, 65%, 70%, 75%, 80%, 85%, 90%, 91%, 92%, 93%, 94%, 95%, 96%, 97%, 98%, 99%, or 100% identity to SEQ ID NOs: 1-3, or SEQ ID NOs: 29-31, or a fluorescent protein with a nucleic acid sequence having at least 50%, 55%, 60%, 65%, 70%, 75%, 80%, 85%, 90%, 91%, 92%, 93%, 94%, 95%, 96%, 97%, 98%, 99%, or 100% similarity to any of SEQ ID NOs: 22-27 or 37, or a sequence that hybridizes under high stringency conditions to SEQ ID NO: 22-27 or 37 and includes at least one nucleotide difference from SEQ ID NO: 26 within the hybridized region. While a skilled artisan will appreciate that the transgenic plant may be any species of plant, preferred plant species include, but are not limited to, monocotyledonous plants, dicotyledonous plants, flowering plants, and ornamental plants. Exemplary plants are members of Orchidaceae, such as the genus *Phalaenopsis*, or *Solinaceae*.

The present invention provides a method of producing a LanFP by cultivating a host cell expressing the LanFP and isolating the LanFP from a population of such cells. Methods to express and isolate a LanFP are known in the art. It is envisioned that host cells containing a LanFP extrachromosomally or integrated within its genome can be cultured and grown such that the LanFP is expressed. The LanFP can be isolated from the host cells by conventional methods known in the art.

The *Branchiostoma* fluorescent polypeptides provided (LanFP) may be used in combination with nucleic acids encoding at least one component of a bioluminescence generating system. Such components include, but are not limited to, luciferases or luciferins. It is envisioned that the described combination will result in a fusion protein of the component and at least one LanFP. The nucleotide sequence encoding a LanFP will comprise a nucleic acid sequence that encodes a polypeptide having at least 50%, 55%, 60%, 65%, 70%, 75%, 80%, 85%, 90%, 91%, 92%, 93%, 94%, 95%, 96%, 97%, 98%, 99%, or 100% identity to SEQ ID NOs: 1-3, 29-31, or 38, or a fluorescent protein encoded by a nucleic acid molecule of *Branchiostoma floridae* having at least 50%, 55%, 60%, 65%, 70%, 75%, 80%, 85%, 90%, 91%, 92%, 93%, 94%, 95%, 96%, 97%, 98%, 99%, or 100% similarity to any of SEQ ID NOs: 22-27, 37 or their respective complementary sequences, or a sequence that hybridizes under high stringency conditions to SEQ ID NO: 22-27 or 37 and includes at least one nucleotide difference from SEQ ID NO: 26 within the hybridized region. It is envisioned that the LanFP sequence may be fused to a *Renilla* luciferase or other components of bioluminescence generating systems. Such bioluminescence generating systems include those isolated from an insect system, a coelenterate system, a ctenophore system, a bacterial system, a mollusk system, a crustacean system, a fish system, an annelid system, an amphibian system, an avian system, a yeast system, an earthworm system, and a mammalian system. Exemplary systems include those isolated from fireflies, *Mnemiopsis, Beroe ovata, Branchiostoma, Aequorea, Obelia, Vargula, Pelagia, Renilla, Pholas, Poriethys, Cyprindina, Aristostomias, Pachystomias, Malacosteus, Gonadostomias, Gaussia, Watensia, Halisturia, Vampire squid, Glyphus, Mycotophids, Vinciguerria, Howella, Florenciella, Chaudiodus, Melanocostus, Sea Pens, Chiroteuthis, Eucleoteuthis, Onychoteuthis, Watasenia, cuttlefish, Sepiolina, Oplophorus, Acanthophyra, Sergestes, Gnathophausia, Argyropelecus, Yarella, Diaphus, Gonadostomias, Neoscopelus,* mice, rat, primate, human cells, zebrafish, *Drosophila, Xenopus, Saccharomyces cerevisiae, Saccharomyces pombe* and *Escherichia coli*.

The invention provides antibodies that specifically bind to the subject fluorescent proteins. It is envisioned that such antibodies, or antigen-binding fragments, will specifically bind to a polypeptide that comprises an amino acid sequence having at least 50%, 55%, 60%, 65%, 70%, 75%, 80%, 85%, 90%, 91%, 92%, 93%, 94%, 95%, 96%, 97%, 98%, 99%, or 100% identity to any of SEQ ID NOs: 1-3, 29-31, or 37. Such antibody may be monoclonal, polyclonal, an antigen-binding fragment, an IgG antibody, or an IgM antibody. A suitable antigen binding fragment is an scFv, Fv, Fab', Fab, diabody, linear antibody or F(ab')2, antigen-binding fragment of an antibody. The antibody may also exist as a dimer, trimer or multimer. It may be a human, harmonized, hybrid antibody, or antigen-binding fragment comprising one or more fragments or regions from a different organism such a human fragment combined with a mouse fragment The antibody or antigen-binding fragment may also be operatively attached to one or more therapeutic or diagnostic agents. Of course, which agent is attached will depend upon the intended use of the antibody.

The present invention includes kits comprising at least one LanFP and instructions for its use. Combinations of more than one LanFP may be provided in a kit or used in practicing the invention. Further, the supplied LanFP may be contained within an expression vector or plasmid and combinations of more than one LanFP within a single expression vector or individual expression vectors may be provided in a kit or used in practicing the invention. Other biological agents or components may also be included, such as those for expressing and isolating the protein. In such kits, the components are maintained separately in containers within a container that holds all the components.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF DRAWINGS

The application file contains at least one drawing executed in color. Copies of this patent application publication with color drawing(s) will be provided by the Office upon request and payment of the necessary fee. The following drawings form part of the present specification and are included to further demonstrate certain aspects of the present invention. The invention may be better understood by reference to one or more of these drawings in combination with the detailed description of specific embodiments presented herein.

FIG. 1 shows an alignment of assembled LanFP1 (SEQ ID NO: 25) and muranized LanFP1 (SEQ ID NO: 22). The shaded nucleotides indicate nucleotides shared by the two sequences. The nucleotides not shaded indicate nucleotide positions that were altered during the harmonization process to generate a muranized LanFP1, which is expressed more efficiently in mammalian expression systems.

FIGS. 8A-D show the average fluorescence lifetime for muranized LanFP1. The intensity image (FIG. 8A) and corresponding lifetime image (FIG. 8B) demonstrate significant variations in fluorescence intensity, but a single fluorescence lifetime. The resultant curves are fit to a single exponential decay (FIG. 8C), and the average pixel histogram for lifetimes (FIG. 8D) demonstrates muranized LanFP 1 has a lifetime of about 2.5 nanoseconds.

FIG. 13B provides a phylogenetic relationship and shows that LanFP1, LanFP2, and LanFP3 are distantly related to EGFP (humanized GFP). Homology was determined using Align X protein alignment tool in the Vector NTI suite.

FIG. 21 illustrates a multiple sequence alignment of known fluorescent proteins and LanFPs of the invention including amino acid sequences of GFP_Aequorea_17026382 (SEQ ID NO: 4), KillerRed_63253819 (SEQ ID NO: 5), G-to-R_55667942 (SEQ ID NO: 6), 2BTJ_71042772 (SEQ ID NO: 7), All_ancestor_55824502 (SEQ ID NO: 8), R_G_ancestor_55824468 (SEQ ID NO: 9), pre-R_anc_55824524 (SEQ ID NO: 10), Azami_Green_52839539 (SEQ ID NO: 11), Cyan 16508125 (SEQ ID NO: 12), Discosoma_G_20086758 (SEQ ID NO: 13), Chromo_51593136 (SEQ ID NO: 14), Orange_55420615 (SEQ ID NO: 15), Plum_55792809 (SEQ ID NO: 16), dsRED_1G7K_12084494 (SEQ ID NO: 17), wtYellow_1XAE_61680324 (SEQ ID NO: 18), kindling_red_28629493 (SEQ ID NO: 19), GFP_Renilla_14161475 (SEQ ID NO: 20), GFP2_Pontellina_33243028 (SEQ ID NO: 21), LanFP3 (SEQ ID NO: 3), LanFP2 (SEQ ID NO: 2), and LanFP1 (SEQ ID NO: 1).

FIG. 22 provides an alignment of the LanFP proteins LanFP 1-6 as compared with EGFP. Shading indicates the level of similarity between amino acids based on polarity, hydropathy, and charge.

DETAILED DESCRIPTION

Figure 2:
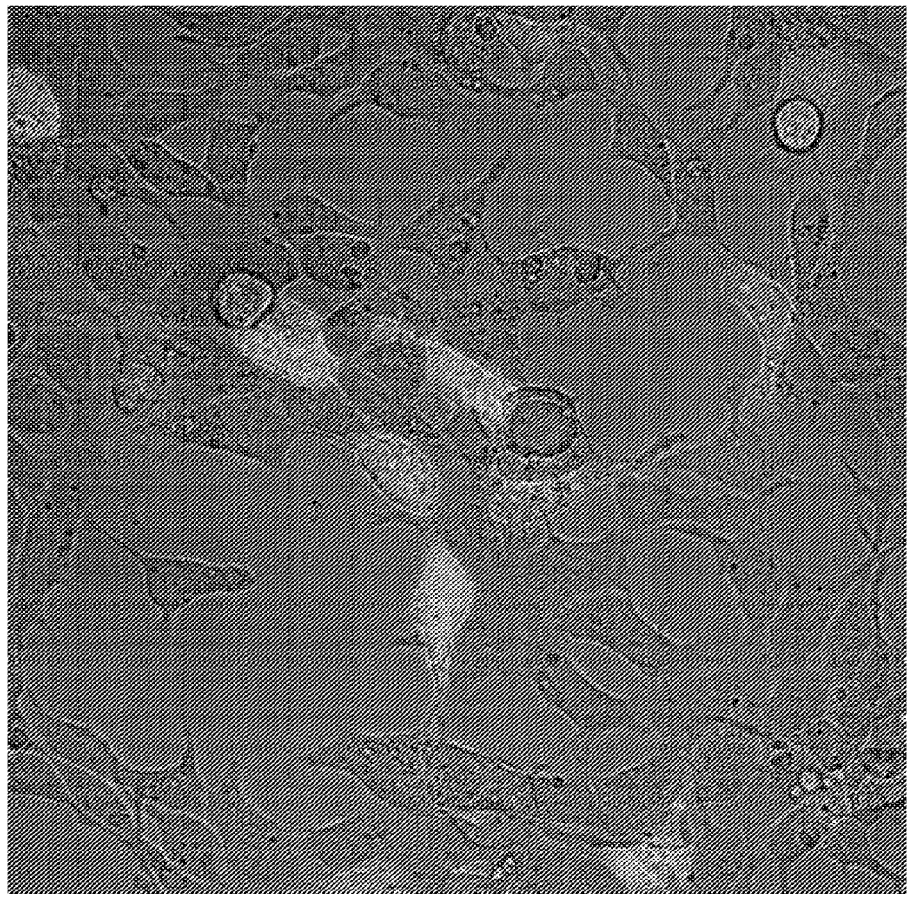
FIG. 2 shows that muranized LanFP1 (green, SEQ ID NO: 22) is efficiently expressed in human embryonic kidney (HEK-293) cells. Cells were analyzed by confocal microscopy 24-72 hours post transfection using excitation at 488 nm and a 505 nm long pass filter. The cell outlines were identified with DIC imaging.

The present invention relates to novel fluorescent proteins isolated from *Branchiostoma* species and uses thereof. The invention includes new nucleic acid sequences and fluorescent proteins derived from a close relative to vertebrae species with inherent characteristics ideal for use with vertebrae derived expression systems. As such, methods for improving the use of fluorescent proteins in mammalian systems are also contemplated.

1. Lancelet Fluorescent Proteins
A. Nucleic Acids Encoding Lancelet Fluorescent Proteins Nucleic acids encoding bioluminescent proteins (LanFPs) isolated from the *Branchiostoma* species are disclosed. A LanFP nucleotide sequence includes an open reading frame that encodes a fluorescent polypeptide. In particular, a LanFP nucleic acid is capable, under appropriate conditions, of expressing a fluorescent protein such as that illustrated by SEQ ID NOs: 1-3, 29-31, and 37.

LanFP nucleotides further include nucleic acid sequences that hybridize under high stringency conditions to SEQ ID NOs: 22, 23, 24, 25, 26, 27, 33, 34, 35, or 37 such as those that are homologous, substantially similar, or identical to the nucleic acids of the present invention. Homologous nucleic acid sequences will have a sequence similarity of at least about 50%, 55%, 60%, 65%, 70%, 75%, 80%, 85%, 90%, 91%, 92%, 93%, 94%, 95%, 96%, 97%, 98%, 99%, or 100% to any of SEQ ID NOs: 22-27, 33-35, 37 or the respective complementary sequences. Sequence similarity may be calculated using a number of algorithms known in the art, such as BLAST, described in Altschul, S. F., et al., J. Mol. Biol. 215:403-10, 1990 (using default settings, i.e. parameters w=4 and T=17). The nucleic acids may differ in sequence from the above-described nucleic acids due to the degeneracy of the genetic code. In general, a reference sequence will be 18 nucleotides, more usually 30 or more nucleotides, and may comprise an entire LanFP sequence for comparison purposes.

Nucleotide sequences that can express a LanFP or related protein and hybridize to the listed nucleotide sequences are contemplated herein. Stringent hybridization conditions include conditions such as hybridization at 50° C. or higher and 0.1×SSC (15 mM sodium chloride/1.5 mM sodium citrate). Another example is overnight incubation at 42° C. in a solution of 50% formamide, 5×SSC (150 mM NaCl, 15 mM trisodium citrate), 50 mM sodium phosphate (pH7.6), 5×Denhardt's solution, 10% dextran sulfate, and 20 µg/ml denatured, sheared salmon sperm DNA, followed by washing in 0.1×SSC at about 65° C. Exemplary stringent hybridization conditions are hybridization conditions that are at least about 80%, 85%, 90%, or 95% as stringent as the above specific conditions. Other stringent hybridization conditions are known in the art and may also be employed to identify homologs of the nucleic acids of the invention (Current Protocols in Molecular Biology, Unit 6, pub. John Wiley & Sons, N.Y., 1989).

Mutant nucleotides of the LanFP proteins may be used, so long as mutants include nucleic acid sequences that encode functional LanFP proteins as described herein. The subject nucleic acids may be mutated to alter properties of the encoded protein such as the maturation rate, emission/excitation spectra, expression properties, folding properties, and other fluorescent properties. A skilled artisan will recognize that chromo- or fluorescent proteins encoded by nucleic acids encoding homologues or mutants may have the same fluorescent properties as the wild-type fluorescent protein or may have altered spectral properties. The DNA sequence or protein product of such a mutation will usually be substantially similar to the sequences provided herein and will differ by one or more nucleotides or amino acids. The sequence changes may be substitutions, insertions, deletions, or a combination thereof. Techniques for mutagenesis of cloned genes are known in the art. Methods for site specific mutagenesis may be found in Gustin et al., Biotechniques 14:22, 1993; Barany, Gene 37:111-23, 1985; Colicelli et al., Mol. Gen. Genet. 199:537-9, 1985; and Sambrook et al., Molecular Cloning: A Laboratory Manual, CSH Press 1989, pp. 15.3-15.108 and all incorporated herein by reference. Such mutated nucleic acid derivatives may be used to study structure-function relationships of a particular fluorescent protein, or to alter properties of the protein that affect its function or regulation. In summary, the invention relates to LanFP coding sequences such as those of SEQ ID NOs: 22-27, 33-35, 37, and variants or mutants thereof. Also, the invention encompasses the intermediatary RNAs encoded by the described nucleic acid sequences and that translates into a LanFP of the invention.

1. Harmonization of Nucleic Acid Sequences Encoding LanFPs

To circumvent problems associated with poor translation efficiency of non-mammalian derived mRNA in mammalian systems, strategies to humanize, or harmonize, proteins are often used. Harmonizing a protein involves optimizing the nucleotide codons encoding specific amino acids to those more likely to be used in mammalian genes. For example, GCC, GCT, GCA and GCG all encode the amino acid Alanine; however, GCC is more often used to encode Alanine in human genes than GCG (Table 1). To increase translation efficiency in human cells, at the Alanine position, GCG should be replaced with GCC. Strategies to humanize proteins are described in U.S. Pat. No. 5,968,750, filed Oct. 9, 1998, and incorporated herein by reference.

The present invention provides nucleic acid sequences encoding muranized fluorescent proteins of the invention. The nucleic acids SEQ ID NO: 22, SEQ ID NO: 23, and SEQ ID NO: 24 have been optimized using the preferred codons of mouse genes (Table 2) in order to increase protein translation in mammalian systems. One skilled in the art will recognize that coding sequences may be optimized for use in any species through codon harmonization.

Preferred codons for protein expression for a wide variety of organisms can be obtained from publicly available codon usage databases. The Codon Usage Database is an extended worldwide web version of CUTG (Codon Usage Tabulated from GenBank) developed and maintained by Yasukazu Nakamura at The First Laboratory for Plant Gene Research, Kazusa DNA Research Institute, Japan. The KEGG (Kyoto Encyclopedia of Genes and Genomes) Database is another database and is described in Aoki and Kanehisa, Current Protocols in Bioinformatics, (2005) 1.12.1-1.12.54, which is incorporated herein by reference.

TABLE 1

Preferred DNA Codons for Human Use.

| Amino Acid[1] | | | Codons Preferred in Human Genes | | | | | |
|---|---|---|---|---|---|---|---|---|
| Alanine | Ala | A | GCC | GCT | GCA | GCG | | |
| Cysteine | Cys | C | TGC | TGT | | | | |
| Aspartic acid | Asp | D | GAC | GAT | | | | |
| Glutamic acid | Glu | E | GAG | GAA | | | | |
| Phenylalanine | Phe | F | TTC | TTT | | | | |
| Glycine | Gly | G | GGC | GGG | GGA | GGT | | |
| Histidine | His | H | CAC | CAT | | | | |
| Isoleucine | Ile | I | ATC | ATT | ATA | | | |
| Lysine | Lys | K | AAG | AAA | | | | |
| Leucine | Leu | L | CTG | CTC | TTG | CTT | CTA | TTA |
| Methionine | Met | M | ATC | | | | | |
| Asparagine | Asn | N | AAC | AAT | | | | |
| Proline | Pro | P | CCC | CCT | CCA | CCG | | |
| Glutamine | Gln | Q | CAG | CAA | | | | |
| Arginine | Arg | R | CGC | AGG | CGG | AGA | CGA | CGT |
| Serine | Ser | S | AGC | TCC | TCT | AGT | TCA | TCG |
| Theronine | Thr | T | ACC | ACA | ACT | ACG | | |
| Valine | Val | V | GTG | GTC | GTT | GTA | | |
| Tryptophan | Trp | W | TGG | | | | | |
| Tyrosine | Tyr | Y | TAC | TAT | | | | |

[1]The codons at the left, in the above chart, represent those codons most preferred for use in human genes, with human usage decreasing towards the right.

TABLE 2

Preferred DNA Codons for Mouse Use.

| Amino Acid[1] | | | Codons Preferred in Mouse Genes | | | | |
|---|---|---|---|---|---|---|---|
| Alanine | Ala | A | GCC | GCT | GCA | GCG | |
| Cysteine | Cys | C | TGC | TGT | | | |
| Aspartic acid | Asp | D | GAC | GAT | | | |
| Glutamic acid | Glu | E | GAG | GAA | | | |
| Phenylalanine | Phe | F | TTC | TTT | | | |
| Glycine | Gly | G | GGC | GGA | GGG | GGT | |
| Histidine | His | H | CAC | CAT | | | |
| Isoleucine | He | I | ATC | ATT | ATA | | |
| Lysine | Lys | K | AAG | AAA | | | |
| Leucine | Leu | L | CTG | CTC | TTG | CTT | CTA |
| Methionine | Met | M | ATG | | | | |
| Asparagine | Asn | N | AAC | AAT | | | |
| Proline | Pro | P | CCC | CCT | CCA | CCG | |
| Glutamine | Gln | Q | CAG | CAA | | | |
| Arginine | Arg | R | AGG | AGA | CGG | CGC | CGA |
| Serine | Ser | S | AGC | TCC | TCT | AGT | TCA |
| Theronine | Thr | T | ACC | ACA | ACT | ACG | |
| Valine | Val | V | GTG | GTC | GTT | GTA | |
| Tryptophan | Trp | W | TGG | | | | |
| Tyrosine | Tyr | Y | TAC | TAT | | | |

[1]The codons at the left, in the above chart, represent those codons most preferred for use in murine genes, with murine usage decreasing towards the right.

B. Protein/Polypeptide Compositions

The invention contemplates fluorescent proteins and mutants thereof which include those proteins encoded by the subject nucleic acids, as well as polypeptides comprising the fluorescent proteins. The isolated *Branchiostoma* fluorescent proteins of the invention are exemplified by the sequences of SEQ ID NOs: 1-3, 29-31, and 38. Further, the invention includes both the full-length proteins, as well as portions or fragments thereof. Additionally, the invention includes variations of the naturally occurring proteins, where such variations are homologous or substantially similar to the naturally occurring proteins, and mutants of the naturally occurring proteins, as described herein.

Homologs or proteins (or fragments thereof) that vary in sequence from the amino acid sequences SEQ ID NOs: 1-3, 29-31, and 38 are also included in the invention. By homolog is meant a protein having at least about 10%, usually at least about 25%, 30%, 40%, 45%, 50%, 55%, 60%, 65%, 70%, 75%, 80%, 85%, 90%, 95%, 99% or higher amino acid sequence identity to the proteins encoded by SEQ ID NOs: 1-3 or SEQ ID NOs: 29-31, as determined using MegAlign, DNAstar (1998) clustal algorithm as described in Higgins, D. G. and Sharp, P. M., Fast and Sensitive Multiple Sequence Alignments on a Microcomputer, CABIOS, 5: 151-153, 1989, both incorporated herein by reference.

LanFPs of the invention may be mutated, or altered, to enhance, or change, biological properties of the protein. Such biological properties include spectral properties, such as absorbance maximum, emission maximum, maximum extinction coefficient, brightness (e.g., as compared to the wild-type protein or another reference protein such as GFP from *A. victoria*), and the like; in vivo and/or in vitro stability (e.g., half-life); etc. Suitable mutations include single amino acid changes (compare SEQ ID NO: 2 with SEQ ID NO: 38), deletions of one or more amino acids, N-terminal truncations, C-terminal truncations, insertions, etc. Mutants can be generated using standard techniques of molecular biology, including random mutagenesis and targeted mutagenesis as described in Current Protocols in Molecular Biology, Unit 8, pub, John Wiley & Sons, Inc., 2000 and incorporated herein by reference.

Suitable mutants include an amino acid sequence encoded by an open reading frame (ORF) of the gene encoding the subject isolated protein, including the full length protein and fragments thereof, particularly biologically active fragments and/or fragments corresponding to functional domains, and the like; and including fusions of the subject polypeptides to other proteins or parts thereof. Fragments of interest will typically be at least about 10 amino acids (aa) in length, usually at least about 30, 40, or 50 aa in length, more preferably 60, 70, 80, 90, 100, 110, 120, 130, 140, or 150 aa in length and may be as long as 160, 170, 180, 190, 200, 220, 240, 260, 280 or 300 aa in length or even longer, but will usually not exceed about 1000 aa in length, where the fragment will have a stretch of amino acids that is identical to the subject protein of at least about 10 aa, and usually at least about 15 aa, and in many embodiments at least about 50, 60, 70, 80, 90, 100, 110, 120, 130, 140, or 150 aa in length. The subject polypeptides can be about 25 aa, about 50 aa, about 75 aa, about 100 aa, about 125 aa, about 150 aa, about 200 aa, about 210 aa, about 220 aa, about 230 aa, or about 240 aa in length, up to and including the entire protein. A skilled artisan will recognize that a protein fragment can retain all or substantially all of a biological property of the isolated protein.

1. LanFP Characteristics

Figure 22:
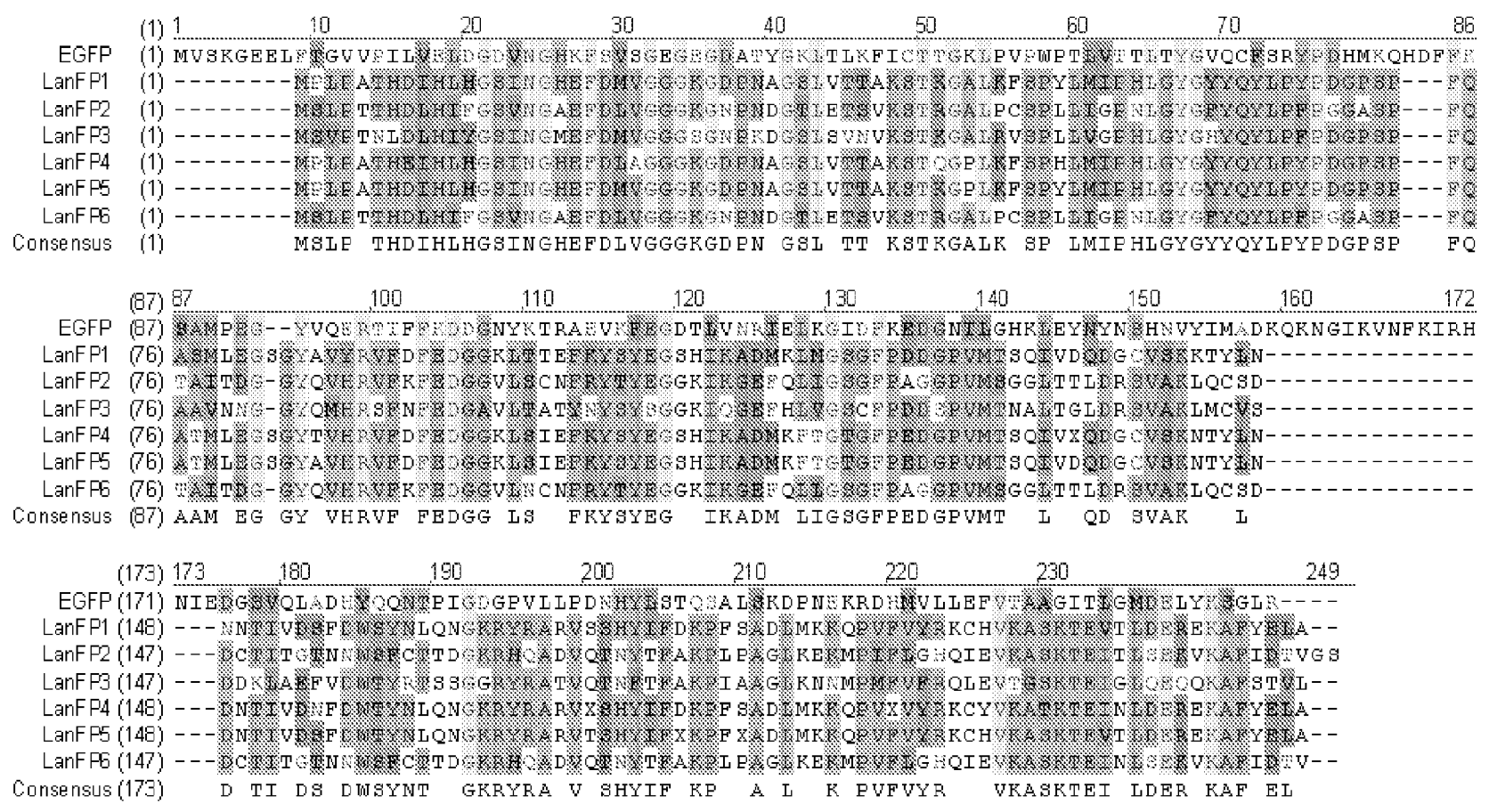

The proteins and polypeptides of the invention are characterized by the ability to fluoresce. A fluorescent protein may or may not be spontaneously fluorescent. For example, it may exhibit low, medium, or high fluorescence, only upon irradiation with light of an excitation wavelength. The fluorescent characteristic, in part, is dependent upon the chromophore structure. The chromophore structure of LanFPs includes the amino acid residues GYG at about positions 58, 59, and 60 found in SEQ ID NOs: 1-3 and 29-31. A skilled artisan will recognize the similarity between the chromophore region of wild type GFP and the LanFPs (FIG. 21); however, the ability of wild type GFP to fluoresce with this chromophore is very limited compared to LanFPs. To enhance the fluorescence of GFP, the chromophore region was altered from GYG to TYG (FIG. 22, EGFP). While the LanFPs fluoresce efficiently with the GYG. chromophore, a skilled artisan will appreciate that the chromophore region may be mutated to alter spectral properties.

The LanFPs of the invention have an absorbance maximum ranging from about 300 to 700, usually from about 350 to 650 and more usually from about 400 to 600 nm. Where the subject proteins are fluorescent proteins, by which is meant that they can be excited at one wavelength of light following which they will emit light at another wavelength, the excitation spectra of the subject proteins typically ranges from about 300 to 700, usually from about 350 to 650 and more usually from about 400 to 600 nm while the emission spectra of the subject proteins typically ranges from about 400 to 800, usually from about 425 to 775 and more usually from about 450 to 750 nm. The subject proteins generally have a maximum extinction coefficient that ranges from about 20,000 to 180,000 $M^{-1}cm^{-1}$ and usually from about 50,000 to 175,000 $M^{-1}cm^{-1}$. The subject proteins typically range in length from about 150 to 300 residues and included herein are specific examples that are 210, 215, 216, 217, 218, 219, 220, and 225 amino acid residues in length. The subject proteins include both shorter and longer variants that range in length from as short as about 155, 160, 165, 170, 175, 180, 185, 190, 200. or 205 to as long as about 230, 235, 240, 245, 250, 255, 260, 265, 270, 275, 280, 285, 290, 295 or even longer. The subject proteins generally have a molecular weight ranging from about 15 to 35 kDa, including specifically 24.52, 23.1, and 23.63 kDa.

The subject proteins fold rapidly following expression in the host cell. By rapidly folding is meant that the proteins achieve their tertiary structure that gives rise to their fluorescent quality in a short period of time, In these embodiments, the proteins fold in a period of time that generally does not exceed about 1 day, usually does not exceed about 8 hours, and more usually does not exceed about 2 hours.

2. LanFP Production

The present invention includes a method of producing a LanFP by cultivating a host cell expressing a LanFP and then isolating the protein. Such methods include the introduction of an expression vector containing at least one protein of the invention into a host cell, as described herein, cultivation of the subject protein containing host cell, and isolation of the subject protein from the cell extract. The expressed subject protein may or may not be linked to another protein of interest. Methods to cultivate host cells are known in the art. Methods to express and isolate a subject protein are described in Current Protocols in Protein Science, Units 5, pub. John Wiley & Sons, Inc., 2002 and Current Protocols in Protein Science, Units 6, pub. John Wiley & Sons, Inc., 2002 and both are incorporated herein by reference.

C. Expression System for LanFPs

1. Vectors

Methods for introducing a DNA sequence into eukaryotic cells are known in the art and typically include the use of a DNA vector or plasmid. There are many vectors known and available in the art that are useful for the polynucleotides provided by the invention. One of skill in the art will recognize that the selection of a particular vector depends upon the intended use of the polynucleotide. Preferably, the DNA sequences are introduced by a vector, or plasmid, capable of transforming and driving the expression of the components of the construct in the desired cell type, whether that cell type is prokaryotic or eukaryotic. Many vectors comprise sequences allowing both prokaryotic vector replication and eukaryotic expression of operably linked gene sequences.

Vectors useful according to the invention may be autonomously replicating, that is, the vector exists extrachromosomally, and its replication is not necessarily directly linked to the replication of the host genome. Alternatively, the replication of the vector may be linked to the replication of the host chromosomal DNA. For example, the vector may be integrated into a chromosome of the host cell as achieved by retroviral vectors.

A vector will comprise sequences operably linked to the coding sequence of the subject polypeptide that permits the transcription and translation of the components when. appropriate. Within the expression vector, a subject polynucleotide is linked to a regulatory sequence as appropriate to obtain the desired expression properties. These regulatory sequences can include promoters (attached either at the 5' end of the sense strand or at the 3' end of the antisense strand), enhancers, terminators, operators, repressors, and inducers. The promoters can be regulated or constitutive. In some situations it may be desirable to use conditionally active promoters, such as tissue-specific or developmental stage-specific promoters. In other words, the expression vector will provide a transcriptional and translational initiation region, which may be inducible or constitutive, where the coding region is operably linked. under the transcriptional control of the transcriptional initiation region, and a transcriptional and translational termination region. These control regions may be native to the subject species from which the subject nucleic acid is obtained, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for, among other things, the production of fusion proteins, as described herein.

A skilled artisan will recognize that the choice of vector for use with the invention is dependent on the host with which the invention will be utilized. Suitable vectors include, but are not limited to, bacteriophage-derived vectors, viral vectors, retroviral vectors, adenoviral vectors, adeno-associated viral vectors, herpesviral vectors, and insect vector systems. Such vectors are well known in the art.

2. Expression Cassettes

Expression cassettes may include a transcription initiation region, at least one polynucleotide of the invention, and a transcriptional termination region. Of particular interest is the use of sequences that allow for the expression of functional epitopes or domains, usually at least about 8 amino acids in length, more usually at least about 15 amino acids in length, to about 25 amino acids, and up to the complete open reading frame of the polynucleotides of the invention. After introduction of the DNA, the cells containing the construct may be selected by means of a selectable marker, the cells expanded and then used for expression.

3. Constructs

The term "construct" as used herein refers to a nucleic acid sequence containing at least one LanFP polynucleotide of the invention operably linked or fused to additional nucleic acids. Such constructs include vectors, plasmids, and expression cassettes encoding at least one polynucleotide of the invention. Constructs may be polynucleotides of the invention fused to other protein coding sequence to generate fusion proteins as described herein. For example, a polynucleotide may be operably linked or fused to a nucleotide sequence encoding a luciferase, luciferin, or other component of a bioluminescence generating system as described herein.

4. Host Cells

Any cell into which a construct of the invention may be introduced and expressed is useful according to the invention. That is, because of the wide variety of uses for the constructs of the invention, any cell in which a construct of the invention may be expressed, and preferably detected, is a suitable host. The construct may exist in a host cell as an extrachromosomal element or be integrated into the host genome.

Host cells may be prokaryotic, such as any of a number of bacterial strains, or may be eukaryotic, such as yeast or other fungal cells, insect, plant, amphibian, or mammalian cells including, for example, rodent, simian or human cells. Host cells may be primary cultured cells, for example primary human fibroblasts or keratinocytes, or may be an established cell line, such as N1H3T3, 293T or CHO cells among others. Further, mammalian cells useful for expression of the constructs may be phenotypically normal or oncogenically transformed. it is assumed that one skilled in the art can readily establish and maintain a chosen host cell type in culture.

For large scale production of the protein, a unicellular organism, such as *E. coli, B. subtilis, S. cerevisiae*, insect cells in combination with baculovirus vectors, or cells of a higher organism such as vertebrates, e.g. COS 7 cells, HEK 293, CHO, *Xenopus* Oocytes, etc., may be used as the expression host cells. In some situations, it is desirable to express the construct in eukaryotic cells, where the expressed protein will benefit from native folding and post-translational modifications. Small peptides can also be synthesized in the laboratory. Polypeptides that are subsets of the complete protein sequence may be used to identify and investigate parts of the protein important for function. Specific expression systems of interest include bacterial, yeast, insect cell and mammalian cell derived expression systems such as those described in U.S. Pat. No. 6,969,597 and incorporated herein by reference.

When any of the above host cells, or other appropriate host cells or organisms, are used to replicate and/or express the polynucleotides or nucleic acids of the invention, the resulting replicated nucleic acid, RNA, expressed protein or polypeptide, is within the scope of the invention as a product of the host cell or organism. The product is recovered by any appropriate means known in the art.

5. Introduction of Constructs to Host Cells.

Constructs provided by the invention, including vectors, plasmids, and expression cassettes containing polynucleotides of the invention, may be introduced to selected host cells by any of a number of suitable methods known to those skilled in the art. For example, constructs may be introduced to appropriate bacterial cells by infection, as in the case of *E. coli* bacteriophage vector particles such as lambda or M13, or by any of a number of transformation methods for plasmid vectors or for bacteriophage DNA. For example, standard calcium-chloride-mediated bacterial transformation is still commonly used to introduce naked DNA to bacteria (Sambrook et al., 1989, Molecular Cloning, A Laboratory Manual, Cold Spring Harbor Laboratory Press, Cold Spring Harbor, N.Y., incorporated herein by reference), electroporation may also be used (Current Protocols in Molecular Biology, pub. John Wiley & Sons, Inc., 1993 and incorporated herein by reference).

For the introduction of a construct containing vectors into yeast or other fungal cells, chemical transformation methods are generally used (as described by Rose et al., 1990, Methods in Yeast Genetics, Cold Spring Harbor Laboratory Press, Cold Spring Harbor, N.Y. and incorporated herein by reference). For transformation of *S. cerevisiae*, for example, the cells are treated with lithium acetate. Transformed cells are then isolated on selective media appropriate to the selectable marker used.

Constructs can be inserted into mammalian host cells by methods including, but not limited to, electroporation, transfection, microinjection, micro-vessel transfer, particle bombardment, biolistic particle delivery, liposome mediated transfer and other methods described in Current Protocols in Cell Biology, Unit 20, pub. John Wiley & Sons, Inc., 2004 and incorporated herein by reference.

For the introduction into insect cells, liposome-mediated transfection is commonly used, as is baculovirus infection. Cells such as Schneider-2 cells (*Drosophila melanogaster*), Sf-9 and Sf-21 cells (*Spodoptera frugiperda*) or High Five™ cells (*Trichoplusia ni*) may be transfected using any of a number of commercially available liposome transfection reagents optimized for use with insect cells. Additionally, particle bombardment, biolistic particle delivery, and microinjection are widely used to transform insects.

6. Host Organism

Non-human transgenic animals that express at least one polynucleotide of the invention may be generated. For example, a host cell containing at least one polynucleotide of the invention, such as a fertilized oocyte or an embryonic stem cell, can be used to create non-human transgenic animals in which a construct of the invention has been introduced into their genome. Such animals are useful for studying tracing cell lineages, randomly marking cells for further study, tracing neuronal circuitry, and studying gene therapy approaches, among other uses. As used herein, a "transgenic animal" is a non-human animal, preferably a mammal, more preferably a rodent such as a rat or mouse, in which one or more of the cells of the animal include a transgene. Other examples of transgenic animals include non-human primates, ungulates, sheep, dogs, cows, swine, horses, cats, fish, reptiles, worms, goats, chickens, amphibians, mollusks, and insects. A "transgene" is exogenous DNA that is integrated into the genome of a cell from which a transgenic animal develops and that remains in the genome of the mature animal, thereby directing the expression of an encoded gene product in one or more cell types or tissues of the transgenic.

A transgenic animal of the invention can be created by introducing construct-encoding nucleic acid into the male pronuclei of a fertilized oocyte (e.g., by microinjection, retroviral infection) and allowing the oocyte to develop in a pseudopregnant female foster animal. A construct of the invention can be introduced as a transgene into the genome of a non-human animal. Intronic sequences and polyadenylation signals can also be included in the transgene to increase the efficiency of expression of the transgene. Methods for generating transgenic animals via embryo manipulation and microinjection, particularly animals such as mice, have become conventional in the art and are described, for example, in U.S. Pat. No. 4,736,866, filed Jun. 22, 1984; U.S. Pat. No. 4,870,009, filed Dec. 15, 1983; and U.S. Pat. No. 4,873,191, filed Aug. 18, 1986; and Hogan, 1986. In: Manipulating The Mouse Embryo, Cold Spring Harbor Laboratory Press, Cold Spring Harbor, N.Y. Similar methods are used for production of other transgenic animals.

Clones of the non-human transgenic animals described herein can also be produced according to the methods described in Wilmut, et al., Nature 385: 810-813, 1997 and incorporated herein by reference. In brief, a cell (e.g., a somatic cell) from the transgenic animal can be isolated and induced to exit the growth cycle and enter Go phase. The quiescent cell can then be fused, through the use of electrical pulses, to an enucleated oocyte from an animal of the same species from which the quiescent cell is isolated. The reconstructed oocyte is then cultured such that it develops to morula or blastocyte stage and then is transferred to a pseudopregnant female foster animal. The offspring born of this female foster animal will be a clone of the animal from which the cell is isolated.

7. Host Plants

Polynucleotides of the invention can be used to generate transgenic plants including, but not limited to, flowering and ornamental plants, such as an orchid. The constructs provided by the invention can be used to produce transgenic plants by a variety of methods known in the art. Methods of preparing transgenic plant cells and plants are described in U.S. Pat. Nos. 5,767,367; 5,750,870; 5,739,409; 5,689,049; 5,689,045; 5,674,731; 5,656,466; 5,633,155; 5,629,470; 5,595,896; 5,576,198; 5,538,879; 5,484,956; 6,020,538; 6,121,512; 6,271,442; 6,770,799; and 7,049,489, the disclosures of which are incorporated by reference. Methods of producing transgenic plants are also reviewed in Plant Biochemistry and Molecular Biology (eds Lea & Leegood, John Wiley & Sons) (1993) pp 275-295 which is also incorporated by reference.

In brief, a suitable plant cell or tissue is harvested, depending on the nature of the plant species. As such, in certain instances, protoplasts will be isolated, where such protoplasts may be isolated from a variety of different plant tissues, e.g. leaf, hypoctyl, root, etc. For protoplast isolation, the harvested cells are incubated in the presence of cellulases in order to remove the cell wall, where the exact incubation conditions vary depending on the type of plant and/or tissue from which the cell is derived. The resultant protoplasts are then separated from the resultant cellular debris by sieving and centrifugation. Instead of using protoplasts, embryogenic explants comprising somatic cells may be used for preparation of the transgenic host. Following cell or tissue harvesting, exogenous DNA of interest is introduced into the plant cells, where a variety of different techniques are available for such introduction.

With isolated protoplasts, the opportunity arises for introduction via DNA-mediated gene transfer protocols, including: incubation of the protoplasts with naked DNA, e.g. plasmids, comprising the exogenous coding sequence of interest in the presence of polyvalent cations, e.g. PEG or PLO; and electroporation of the protoplasts in the presence of naked DNA comprising the exogenous sequence of interest. Protoplasts that have successfully taken up the exogenous DNA are then selected, grown into a callus, and ultimately into a transgenic plant through contact with the appropriate amounts and ratios of stimulatory factors, e.g. auxins and cytokinins. With embryogenic explants, a convenient method of introducing the exogenous DNA in the target somatic cells is through the use of particle acceleration or "gene-gun" protocols. The resultant explants are then allowed to grow into chimera plants, cross-bred and transgenic progeny are obtained. Instead of the naked DNA approaches described above, another convenient method of producing transgenic plants is *Agrobacterium* mediated transformation.

*Agrobacterium* mediated transfection can be utilized to create transgenic plants. Since most dicotyledonous plants are natural hosts for *Agrobacterium*, almost every dicotyledonous plant may be transformed by *Agrobacterium* in vitro. Although monocotyledonous plants are not natural hosts to *Agrobacterium*, work to transform them using *Agrobacterium* has also been carried out (Hooykas-Van Slogteren et al., Nature 311:763-764, 1984 and incorporated herein by reference). Plant genera that may be transformed by *Agrobacterium* include, but are not limited to, *Arabidopsis, Chrysanthemum, Dianthus, Gerbera, Euphorbia, Pelaronium, Ipomoea, Passiflora, Cyclamen, Malus, Prunus, Rosa, Rubus, Populus, Santalum, Allium, Lilium, Narcissus, Ananas, Arachis, Phaseolus* and *Pisum*.

For transformation with *Agrobacterium*, disarmed *Agrobacterium* cells are transformed with recombinant Ti plasmids of *Agrobacterium tumefaciens* or Ri plasmids of *Agrobacterium rhizogenes*, such as those described in U.S. Pat. No. 4,940,838, filed Feb. 23, 1984 and incorporated herein by reference. The construct of the invention, contained within the recombinant plasmid, can then be stably integrated into the plant genome by infection with the transformed *Agrobacterium* strain. For example, heterologous nucleic acid sequences have been introduced into plant tissues using the natural DNA transfer system of *Agrobacterium tumefaciens* and *Agrobacterium rhizogenes* bacteria (Klee et al, Ann. Rev. Plant Phys. 38:467-486, 1987 and incorporated herein by reference).

There are three common methods to transform plant cells with *Agrobacterium*. The first method is co-cultivation of *Agrobacterium* with cultured isolated protoplasts. This method requires an established culture system that allows culturing protoplasts and plant regeneration from cultured protoplasts. The second method is the transformation of cells or tissues with *Agrobacterium*. This method requires that *Agrobacterium* can transform the plant cells or tissues and that the transformed cells or tissues can be induced to regenerate into whole plants. The third method is transformation of seeds, apices or meristems with *Agrobacterium*. This method requires micropropagation.

One of skill in the art will recognize that the efficiency of transformation by *Agrobacterium* may be enhanced by using a number of methods known in the art. For example, the inclusion of a natural wound response molecule such as acetosyringone (AS) to the *Agrobacterium* culture has been shown to enhance transformation efficiency with *Agrobacterium tumefaciens* (Shahla et al., Plant Molec. Biol. 8:291, 1987 and incorporated herein by reference). Alternatively, wounding the target tissue to be transformed may enhance transformation efficiency. For example, the wounding of plant tissue may be achieved by punching, maceration, or bombardment with microprojectiles (Bidney et al., Plant Molec. Biol. 18:301, 1992 and incorporated herein by reference).

Plant cells can also be transfected with vectors via particle bombardment (i.e., with a gene gun). Particle mediated gene transfer methods are known in the art, are commercially available, and include, but are not limited to, the gas driven gene delivery instrument described in U.S. Pat. No. 5,584,807, filed Jan. 20, 1995 and incorporated herein by reference. This method involves coating the nucleic acid sequence of interest onto heavy metal particles, and accelerating the coated particles under the pressure of compressed gas for delivery to the target tissue.

Other particle bombardment methods are also available for the introduction of heterologous nucleic acid sequences into plant cells. Generally, these methods involve depositing a nucleic acid sequence of interest upon the surface of small, dense particles of a material such as gold, platinum, or tungsten. The coated particles are then coated onto either a rigid surface, such as a metal plate, or onto a carrier sheet made of a fragile material such as Mylar. The coated sheet is then accelerated toward the target biological tissue. The use of the flat sheet generates a uniform spread of accelerated particles that maximizes the number of cells receiving particles under uniform conditions, resulting in the introduction of a nucleic acid sequence of interest into the target tissue. The nucleic acid sequence of interest will encode a construct of the invention.

Plants, plant cells and tissues transformed with a construct of the invention can be readily detected using methods known in the art including, but not limited to, restriction mapping of the genomic DNA, PCR-analysis, DNA-DNA hybridization, DNA-RNA hybridization, and DNA sequence analysis.

E. Antibody Compositions

The invention also contemplates antibodies that specifically bind to the provided fluorescent proteins. Suitable antibodies are obtained by immunizing a host animal with peptides comprising all or a portion of the subject protein. Host animals suitable for immunization include mouse, rat, sheep, goat, hamster, rabbit, etc. The immunogen may comprise the complete protein, or fragments and derivatives thereof.

For preparation of polyclonal antibodies, the first step is immunization of the host animal with the target protein, where the target protein will preferably be in substantially pure form, comprising less than about 1% contaminant. The immunogen may comprise the complete target protein, fragments, or derivatives thereof. To increase the immune response of the host animal, the target protein may be combined with an adjuvant, where suitable adjuvants include alum, dextran, sulfate, large polymeric anions, oil & water emulsions, e.g. Freund's adjuvant, or Freund's complete adjuvant. The target protein may also be conjugated to synthetic carrier proteins or synthetic antigens, A variety of hosts may be immunized to produce the polyclonal antibodies. Such hosts include rabbits, guinea pigs, rodents (e.g. mice or rats), sheep, goats, pigs, ungulates, primates, and the like. The target protein is administered to the host, usually intradermally, with an initial dosage followed by one or more, usually at least two, additional booster dosages. Following immunization, the blood from the host will be collected, followed by separation of the serum from the blood cells. The Ig present in the resultant antiserum may be further fractionated using known methods, such as ammonium salt fractionation, DEAE chromatography, and the like.

Monoclonal antibodies can be produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies to the human protein include mouse, rat, hamster, etc. To raise antibodies against the mouse protein, the animal will generally be a hamster, guinea pig, rabbit, etc. The antibody may be purified from the hybridoma cell supernatants or ascites fluid by conventional techniques, e.g. affinity chromatography using protein bound to an insoluble support, protein A sepharose, etc.

The antibody may be produced as a single chain, instead of the normal multimeric structure. Single chain antibodies are described in Jost, et al., J. B. C. 269:26267-73, 1994. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

Also of interest are humanized antibodies. Methods of harmonizing antibodies are known in the art. The humanized antibody may be the product of an animal having transgenic human immunoglobulin constant region genes (for example International Patent Applications WO 90/10077 and WO 90/04036, both incorporated herein by reference). Alternatively, the antibody of interest may be engineered by recombinant DNA techniques to substitute the CH1, CH2, CH3, hinge domains, and/or the framework domain with the corresponding human sequence (WO 92/02190 and incorporated herein by reference).

The use of Ig cDNA for construction of chimeric immunoglobulin genes is known in the art (Liu et al., P.N.A.S. 84:3439, 1987 and incorporated herein by reference). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202, both incorporated herein by reference). Alternatively, a library is made and screened to isolate the sequence of interest. The DNA sequence encoding the variable region of the antibody is then fused to human constant region sequences. The sequences of human constant regions genes may be found in Kabat et al., Sequences of Proteins of Immunological Interest, N.I.H. publication no. 91¬3242, 1991. Human C region genes are readily available from known clones. The choice of isotype will be guided by the desired effector functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

Antibody fragments, such as Fv, F(ab').sub.2 and Fab may be prepared by cleavage of the intact protein, e.g. by protease or chemical cleavage. Alternatively, a truncated gene is designed. For example, a chimeric gene encoding a portion of the F(ab').sub.2 fragment would include DNA sequences encoding the CH1 domain and hinge region of the H chain, followed by a translational stop codon to yield the truncated molecule.

Consensus sequences of H, L, and J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like, that include one or more LanFP are also provided by the invention. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al., Mol. Cell. Bio. 3:280, 1983), Rous sarcoma virus LTR (Gorman et al., P.N.A.S. 79:6777, 1982), and moloney murine leukemia virus LTR (Grosschedl et al., Cell 41:885, 1985); native Ig promoters, etc.

II. Utility and Methods of Use

The fluorescent proteins of the present invention may be used in a variety of applications for which known fluorescent proteins are used. The multiple uses of fluorescent proteins have been extensively documented since the original cloning of wild type jellyfish GFP. Routine uses of fluorescent proteins have been described in U.S. Pat. No. 5,968,750, filed Oct. 9, 1999; U.S. Pat. No. 6,969,597, filed Feb. 20, 2002; U.S. Pat. No. 6,936,428, filed Dec. 13, 2001; U.S. Pat. No. 6,458,547, filed Oct. 1, 2002; U.S. Patent Application No. 0050272111, filed Jul. 6, 2005; U.S. Patent Application No. 2004/0138420, filed Jul. 15, 2004; and U.S. Patent Application No. 2005/0014223, filed Jan. 20, 2005 and all incorporated herein by reference. Such uses of fluorescent proteins, in general, stem from their ready detection using UV light sources, real-time detection in vivo, spontaneous fluorescence without additional substrates, and relatively small size. The Lancelet fluorescent proteins (LanFP) of the invention (SEQ ID NOs: 1-3, 29-31, and 38) can be used as described in the aforementioned patents and applications.

A. Tracing and Marking Cells

Fluorescent proteins, such as those of the present invention, can be used to identify transformed or transfected cells, label specific cells, label and locate proteins, measure gene expression in vitro or in vivo, and to study intracellular trafficking. Typically, such methods include the use of fluorescent proteins encoded by an expression vector as described herein. Since not all cells in a population of cells will be successfully transfected or transformed, those including a LanFP may be identified by fluorescence-activated cell sorting (FACS), fluorescence microscopy, or other fluorescence-based detection methods known in the art.

Cells can be traced and marked by pre-labeling cells with a fluorescent protein prior to exposing such cells to an environment in which different cell types are present. Detection of the fluorescent protein allows the location of only the original cells compared with the total population of cells. Likewise, cells transfected with exogenous DNA of interest can be identified by the presence of a fluorescent protein without sacrificing the cell population. This can be accomplished by fusing the protein of interest to the fluorescent protein creating a fusion protein or utilizing a plasmid that comprises at least two transcriptional or translational units. Further, a fusion protein comprising a protein of the invention and a member of a specific binding partner that binds to a cell-surface molecule (e.g., a ligand that binds to a cell surface receptor; an antibody that binds to a cell surface protein; a counter receptor that binds to a cell surface protein; and the like) can be used to identify and/or fractionate and/or isolate one or more cell populations from a mixture of cells in combination with FACs or other fluorescent based devices. Also, fusion of a fluorescent protein of the invention to a signal peptide or a peptide to be secreted, can allow secretion to be followed in living cells. Methods to trace and labels cells with fluorescent proteins are described in—U.S. Pat. No. 5,968, 750, U.S. Patent Application 2004/0138420, U.S. Patent Application 2005/0014223, U.S. Pat. No. 6,936,428 and U.S. Patent Application No. 60/261,448, all incorporated herein by reference. A skilled artisan will recognize the many uses of marking cells for in vitro and in vivo research purposes. Such additional marking methods are described in U.S. Pat. No. 6,969,597, including but not limited to, in vivo marking in animals, gene therapy, markers following injection into cells or animals, markers for oxygen biosensor devices for monitoring cell viability. Other applications of fluorescent proteins in transgenic animals are described in WO/2000/02997 and incorporated herein by reference.

B. Molecular Weight Markers

Standard biological applications may also employ the use of LanFPs. For example, LanFPs may be used as molecular weight markers in such applications as DNA gels, RNA gels, protein gels, Western blots, Southern blots, and Northern blots. Also, LanFPs can be used in calibration of fluorometers, FACS machines and other fluorescence based techniques known in the art. A skilled artisan will recognize that LanFPs can be used for any fluorescence-based method or technique and the specific parameters for use depend upon the method or technique. Methods for using fluorescent proteins in standard biological applications, such as those indicated above, are described in U.S. Pat. No. 5,968,750 and U.S. Patent Application 2005/0014223.

C. Gene Reporter

Gene expression can be monitored and promoter activity can be detected using LanFPs. The fluorescent protein nucleotide can be cloned under the control of a target promoter, whereby activity of the promoter can be monitored by the magnitude of the fluorescent signal. Numerous promoter activities can be analyzed using multiple distinct fluorescent colors simultaneously. For example, the period of promoter activity can be time-scale monitored using destabilized fluorescent proteins with short turnover rates. Fast-maturing fluorescent proteins are desirable to provide a minimal delay between promoter activation and fluorescent signal appearance. Also, a split fluorescent protein may be useful in monitoring promoter activity. A split fluorescent protein is expressed as two separate parts but capable of reconstituting the whole functional protein when cloned under the control of two promoters of interest. The fluorescent signal occurs only when both promoters are active. Variations on these methods to use fluorescent proteins as gene reporters are described in U.S. Pat. No. 5,968,750, U.S. Pat. No. 6,936,428, U.S. Patent Application 2004/0138420 and all incorporated herein by reference.

D. Protein Tag

The most widely used application of fluorescent proteins is protein tagging. LanFPs can be used efficiently as protein tags by cloning them in frame with the target protein at either its N- or C-terminus. The skilled artisan will recognize that while there are numerous experiments using fluorescent proteins as protein tags as described, in each particular case the natural function of the tagged protein must be determined Variations on methods to use fluorescent proteins as protein tags and fusion proteins are described in U.S. Pat. No. 5,968,750, U.S.

Patent Application No. 2005/0272111A1, U.S. Pat. Nos. 6,936,428, 5,968,750, U.S. Patent Application No. 2005/0014223, and U.S. Patent Application No. 2004/0138420, all incorporated by reference herein.

E. Intermolecular Dimerization of Fluorescent Proteins

It may be advantageous to express the fluorescent proteins provided by the invention as dimers to minimize heterodimerization with other fluorescent proteins and increase homodimerization. Such a method to increase homodimerization of fluorescent monomers includes the use of intermolecular dimerization of fluorescent proteins (IDFP) as described in U.S. Pat. No. 6,936,428, filed Dec. 13, 2001 and incorporated herein by reference. An IDFP comprises two copies of the fluorescent polypeptide, linked by a peptide linker sequence. Additionally, the LanFP IDFP may be fused in frame to a protein of interest.

Linker sequences useful according to the invention serve to join monomers in the dimeric fluorescent polypeptides of the invention are described in U.S. Pat. No. 6,936,428, A suitable linker is preferably about 5 to about 50 amino acids in length, and more preferably about 10 to about 20 amino acids in length. Exemplary linkers useful in the invention include, but are not limited to, the Gly-Ala linkers taught by Huston et al., U.S. Pat. No. 5,258,498 and incorporated herein by reference; (Arg-Ala-Arg-Asp-Pro-Arg-Val-Pro-Val-Ala-Thr)1-5 (SEQ ID NO: 32) (U.S. Pat. No. 6,936,428; Xu et al., Proc. Natl. Acad. Sci. U.S.A. 96: 151-156, 1999); (Gly-Ser)n (Shao et al., Bioconjug. Chem. 11: 822-826, 2000); (Thr-Ser-Pro)n (Kroon et al., Fur. J. Biochem. 267: 6740-6752, 2000); (Gly-Gly-Gly)n. (Kluczyk et al., Peptides 21; 1411-1420, 2000), and (Glu-Lys)n (Kluczyk et al., Peptides 21:1411-1420, 2000), wherein n is 1 to 15 (each of the preceding references is also incorporated herein by reference).

It may be advantageous to express an IDFP of the invention as a fusion with a protein of interest. The protein of interest can be any protein for which the nucleic acid sequence is known and for which that sequence or at least a relevant part of that sequence can be cloned into a vector encoding an IDFP. The fusion of an IDFP with a polypeptide of interest may be through linkage of the IDFP sequence to either the N or C terminus of the fusion partner. Fusions comprising IDFP polypeptides of the invention need not comprise only a single polypeptide or domain in addition to the IDFP. Rather, any number of domains of interest may be linked in any way as long as the IDFP coding region retains its reading frame and the encoded polypeptide retains fluorescence activity.

Exemplary proteins of interest include, but are not limited to receptors (transmembrane and intracellular) and cell surface proteins, growth factors, signal transduction proteins, transcription factors, structural proteins (e.g., cytoskeletal proteins, nuclear matrix proteins, histones, etc.), extracellular matrix proteins, immunoglobulins, bacterial proteins, plant proteins, viral or phage proteins, enzymes, therapeutic proteins, phosphoproteins, glycoproteins, and lipoproteins. Suitable proteins of interest also include antisense oligonucleotides that, when expressed, inhibit translation of a specific target. Such antisense oligonucleotides include siRNA, miRNA, single-stranded DNA phosphorothioate antisense, 2-O alkyl, peptide nucleic acid (PNA), locked nucleic acid (LNA) or Morpholino antisense.

IDFPs encoding LanFPs of the invention may be used to measure the interaction of two polypeptides of interest and screen for compounds that modulate the interaction of a specific binding pair. Such methods are described in U.S. Pat. No. 6,936,428, filed Dec. 13, 2001 and incorporated herein by reference. A skilled artisan will recognize that these methods may be altered to use LanFPs as monomeric proteins instead of multimeric proteins.

F. Microscopy and Spectroscopy Techniques

Fluorescent proteins have vastly expanded the art of imaging with techniques such as those based on fluorescence detection, bleaching recovery, and non-radioactive transfer. A skilled artisan will appreciate the utility of the subject fluorescent proteins in all fluorescent-based imaging, microscopy and spectroscopy techniques including variations on such.

1. Fluorescence Detection

Fluorescence detection techniques include those that involve detecting fluorescence generated within a system. Such techniques include, but are not limited to, fluorescence microscopy, fluorescence activated cell sorting (FACS), fluorescent flow cytometry, fluorescence correlation spectroscopy (FCS), fluorescence in situ hybridization (FISH), fluorescence imaging with one nanometer accuracy (FIONA), free radical initiated peptide. sequencing (FRIPs), and second harmonic retinal imaging of membrane potential (SHRIMP). For example, in FACS applications, a subject fluorescent protein is used as a label to mark a population of cells and the resulting labeled. population of cells is then sorted with a fluorescent activated cell sorting device, as is known in the art. FACS methods are described in U.S. Pat. Nos. 5,968,738 and 5,804,387, both incorporated herein by reference. A. skilled artisan will appreciate the ever-increasing number of fluorescent-based detection techniques available in the art of which the subject proteins may be utilized. Methods for such techniques are described in Current Protocols in Cytometry, pub. John Wiley & Sons, Inc., 1997-2006; Yildiz, A. and Selvin, P. R. Acc. Chem. Res. 38 (7), 574¬582, 2005; Campagnola P. J. et al., J Biomed Opt. 6(3): 277-86, July 2001, all of which are incorporated herein by reference.

2. Bleaching Recovery

The field of cell biology is rapidly being transformed by the application of fluorescent proteins as fusion tags to track dynamic behavior in living cells. In this regard, fluorescence recovery after photobleaching (FRAP) can be employed in combination with the subject fluorescent proteins to selectively destroy fluorescent molecules within a region of interest with a high-intensity laser, followed by monitoring the recovery of new fluorescent molecules into the bleached area over a period of time with low-intensity laser light. Variants of FRAP include, but are not limited to, polarizing FRAP (pFRAP), fluorescence loss in photo-bleaching (FLIP), fluorescence localization after photobleaching (FLAP). The resulting information from FRAP and variants of FRAP can be used to determine kinetic properties, including the diffusion coefficient, mobile fraction, and transport rate of the fluorescently labeled molecules. Methods for such photobleaching based techniques are described in Braeckmans, K. et al., Biophysical Journal 85: 2240-2252, 2003; Braga, J. et al., Molecular Biology of the Cell 15: 4749-4760, 2004; Haraguchi, T., Cell Structure and Function 27: 333-334, 2002; Gordon, G. W. et al., Biophysical Journal 68: 766-778, 1995, and all incorporated herein by reference.

3. Non-radioactive Energy Transfer Techniques

Non-radioactive energy transfer reactions are homogeneous luminescence assays based on energy transfer between a donor and an acceptor. Such techniques that may employ the use of the subject fluorescent proteins include, but are not limited to, FRET, FET, FP, HTRF, BRET, FLIM, FLI, TR-FRET, FLIE, smFRET, and SHREK. These techniques are all variations of FRET or BRET which are described in detail below.

a. FRET

Tagging proteins with fluorescent proteins not only allows visualization of proteins, but also the ability to detect interactions between proteins. Basic microscopy techniques do not permit the distinction between protein interactions or co-localization due to low spatial resolution, More advance microscopy techniques such as fluorescence resonance energy transfer (FRET), takes advantage of the properties of fluorescent proteins to allow the distinction to be resolved. FRET is the non-radioactive transfer of energy from an excited donor fluorophore to an acceptor fluorophore, which is in close proximity (<10 nm) to the donor and has an excitation spectrum that overlaps the donor emission spectrum. The result of FRET is the quenching of the donor fluorescence and enhanced fluorescence of the acceptor. The interaction of two proteins can be determined using FRET when the proteins of interest are fused with fluorescent proteins of different colors by monitoring the changes in the ratio of acceptor-donor fluorescence intensity. Furthermore, ternary interactions within a single complex can be deciphered by using three-fluorophore FRET. The skilled artisan will appreciate that as the palette of fluorescent proteins is expanded, more interactions can be deciphered at once.

Specific examples of where FRET assays employing the subject fluorescent proteins may be used include, but are not limited to: the detection of protein-protein interactions (e.g., mammalian two-hybrid system, transcription factor dimerization, membrane protein multimerization, multiprotein complex formation), as a biosensor for a number of different events where a peptide or protein covalently links a FRET fluorescent combination, including the subject fluorescent proteins, and the linking peptide or protein (e.g., a protease specific substrate for caspase mediated cleavage), a linker that undergoes conformational change upon receiving a signal which increases or decreases FRET (e.g., PKA regulatory domain (cAMP-sensor)), phosphorylation (e.g., where there is a phosphorylation site in the linker, the linker has binding specificity to phosphorylated/dephosphorylated domain of another protein, or the linker has Ca2+ binding domain). Representative fluorescence resonance energy transfer or FRET applications in which the subject proteins find use include, but are not limited to, those described in: U.S. Pat. Nos. 6,008,373; 5,998,146; 5,981,200; 5,945,526; 5,945,283; 5,911,952; 5,869,255; 5,866,336; 5,863,727; 5,728,528; 5,707,804; 5,688,648; 5,439,797; 6,936,428; 6,969,597; U.S. Patent Application No. 2005/0272111A1; the disclosures of which are herein incorporated by reference.

b. BRET

The fluorescent proteins may be used in BRET (Bioluminescence Resonance Energy Transfer). BRET is a protein-protein interaction assay based on energy transfer from a bioluminescent donor to a fluorescent acceptor protein. The BRET signal is measured by the amount of light emitted by the acceptor compared to the amount of light emitted by the donor. The ratio of these two values increases as the two proteins are brought into proximity. The BRET assay has been amply described in the literature. See, e.g., U.S. Pat. Nos. 6,020,192; 5,968,750; 6,969,597; 5,874,304; and Xu et al., Proc. Natl. Acad. Sci. U.S.A. 96:151-156, 1999. BRET assays may be performed by genetically fusing a bioluminescent donor protein and a fluorescent acceptor protein independently to two different biological partners to make partner A-bioluminescent donor and partner B-fluorescent acceptor fusions. Changes in the interaction between the partner portions of the fusion proteins, modulated, e.g., by ligands or test compounds, can be monitored by a change in the ratio of light emitted by the bioluminescent and fluorescent portions of the fusion proteins. BRET assays can be used in many of the assays as FRET, some of which are noted above and incorporated by reference.

G. Biosensors

The subject fluorescent proteins may be used as biosensors in prokaryotic and eukaryotic cells, e.g. as Ca2+ ion indicator; as pH indicator, as phosphorylation indicator, as an indicator of other ions, e.g., magnesium, sodium, potassium, chloride and halides. For example, for detection of Ca2+ ion, proteins containing an EF-hand motif are known to translocate from the cytosol to membranes upon Ca2+ binding. These proteins contain a myristoyl group that is buried within the molecule by hydrophobic interactions with other regions of the protein. Binding of Ca2+ induces a conformational change exposing the myristoyl group which then is available for the insertion into the lipid bilayer (called a "Ca2+-myristoyl switch"). Fusion of such an EF-hand containing protein to LanFPs could make an indicator of intracellular Ca2+ by monitoring the translocation from the cytosol to the plasma membrane by confocal microscopy. EF-hand proteins suitable for use in this system include, but are not limited to: recoverin (1-3), calcineurin B, troponin C, visinin, neurocalcin, calmodulin, parvalbumin, and the like.

For pH determinations, a system based on hisactophilins may be employed. Hisactophilins are myristoylated histidine-rich proteins known to exist in Dictyostelium. Their binding to actin and acidic lipids is sharply pH-dependent within the range of cytoplasmic pH variations. In living cells membrane binding seems to override the interaction of hisactophilins with actin filaments. At pH 6.5 they locate to the plasma membrane and nucleus. In contrast, at pH 7.5 they evenly distribute throughout the cytoplasmic space. This change of distribution is reversible and is attributed to histidine clusters exposed in loops on the surface of the molecule. The reversion of intracellular distribution in the range of cytoplasmic pH variations is in accord with a pK of 6.5 of histidine residues. The cellular distribution is independent of myristoylation of the protein. By fusing LanFPs to hisactophilin the intracellular distribution of the fusion protein can be followed by laser scanning, confocal microscopy or standard fluorescence microscopy. Quantitative fluorescence analysis can be done by performing line scans through cells (laser scanning confocal microscopy) or other electronic data analysis (e.g., using metamorph software (Universal Imaging Corp) and averaging of data collected in a population of cells. Substantial pH-dependent redistribution of hisactophilin-FP from the cytosol to the plasma membrane occurs within 1-2 min and reaches a steady state level after 5-10 min. The reverse reaction takes place on a similar time scale. As such, a hisactophilin-fluorescent protein fusion protein that acts in an analogous fashion can be used to monitor cytosolic pH changes in real time in live mammalian cells. Such methods have use in high throughput applications, e.g., in the measurement of pH changes as consequence of growth factor receptor activation (e.g. epithelial or platelet-derived growth factor), chemotactic stimulation/cell locomotion, in the detection of intracellular pH changes as second messenger, in the monitoring of intracellular pH in pH manipulating experiments, and the like.

For detection of PKC activity, the reporter system exploits the fact that a molecule called MARCKS (myristoylated alanine-rich C kinase substrate) is a PKC substrate. It is anchored to the plasma membrane via myristoylation and a stretch of positively charged amino acids (ED-domain) that bind to the negatively charged plasma membrane via electrostatic interactions. Upon PKC activation the ED-domain becomes phosphorylated by PKC, thereby becoming negatively charged, and as a consequence of electrostatic repulsion MARCKS translocates from the plasma membrane to the cytoplasm (called the "myristoyl-electrostatic switch"). Fusion of the N-terminus of MARCKS ranging from the myristoylation motif to the ED-domain of MARCKS to fluorescent proteins of the present invention can provide a detector system for PKC activity. When phosphorylated by PKC, the fusion protein translocates from the plasma membrane to the cytosol. This translocation is followed by standard fluorescence microscopy or confocal microscopy, e.g. using the Cellomics technology or other High Content Screening systems (e.g. Universal Imaging Corp./Becton Dickinson). The above reporter system has application in High Content Screening, e.g., screening for PKC inhibitors or as an indicator for PKC activity in many screening scenarios for potential reagents interfering with this signal transduction pathway.

Methods of using fluorescent proteins as biosensors also include those described in U.S. Pat. Nos. 5,824,485; 6,969,597; 6,936,428; 5,650,135 and U.S. Patent Application No. 2004/0138420 (as well as the references cited therein) the disclosures of which are herein incorporated by reference.

H. Screening Assays

The fluorescent proteins of the invention may also be utilized in applications involving the automated screening of arrays of cells expressing fluorescent reporting groups by using microscopic imaging and electronic analysis. Screening can be used for drug discovery and in the field of functional genomics. For example, they can be used where the subject proteins are used as markers of whole cells to detect changes in multicellular reorganization and migration, such as the formation of multicellular tubules (blood vessel formation) by endothelial cells, the migration of cells through a Fluoroblok Insert System (Becton Dickinson Co.), of to follow wound healing, neurite outgrowth, and the like. The LanFPs can also be used as markers, fused to peptides (e.g., targeting sequences) or proteins, to allow the detection of the change of intracellular location as an indicator for cellular activity. For example, they can be used to detect signal transduction, such as kinase and transcription factor translocation upon stimulius by protein kinase C, protein kinase A, transcription factor NFkB, and NFAT, cell cycle proteins (such as cyclin A, cyclin B1 and cyclin E), protease cleavage with subsequent movement of cleaved substrate, phospholipids, or with markers for the detection of intracellular structures such as endoplasmic reticulum, Golgi apparatus, mitochondria, peroxisomes, nucleus, nucleoli, plasma membrane, histones, endosomes, lysosomes, microtubules, and actin. The LanFPS can be used as tools for High Content Screening, co-localization of other fluorescent fusion proteins with these localization markers as indicators of movements of intracellular fluorescent fusion proteins/peptides or as a marker alone. Examples of applications involving the automated screening of arrays of cells in which the fluorescent proteins of the invention may find use include: U.S. Pat. No. 5,989,835; as well as WO/0017624; WO 00/26408; WO 00/17643; and WO 00/03246; the disclosures of which are herein incorporated by reference.

I. Protease Cleavage Assays

The subject fluorescent proteins may be used in protease cleavage assays as described in U.S. Pat. No. 6,969,597. For example, cleavage inactivated fluorescence assays can be developed using the subject proteins, where the subject proteins are engineered to include a protease specific cleavage sequence without destroying the fluorescent character of the protein. Upon cleavage of the fluorescent protein by an activated protease, fluorescence would sharply decrease due to the destruction of a functional chromophore. Alternatively, cleavage activated fluorescence can be developed using the subject proteins, where the subject proteins are engineered to contain an additional spacer sequence in close proximity/or inside the chromophore. This variant would be significantly decreased in its fluorescent activity, because parts of the functional chromophore would be divided by the spacer. The spacer would be framed by two identical protease specific cleavage sites. Upon cleavage via the activated protease the spacer would be cut out and the two residual "subunits" of the fluorescent protein would be able to reassemble to generate a functional fluorescent protein. Both of the above types of application. could be developed in assays for a variety of different types of proteases, e.g., caspases among others.

J. Bioluminescence Generating Systems

The present invention provides compositions and combinations comprising the LanFPs and components of bioluminescence generating systems. A bioluminescence generating system refers to the components that are necessary and sufficient to generate bioluminescence. These include a luciferase, luciferin, and any necessary co-factors or conditions. A skilled artisan will recognize that virtually any bioluminescent system know in the art will be amenable to use in the combinations and methods provided herein. One of skill in the art will also recognize that factors for consideration in selecting a bioluminescence generating system include, but are not limited to: the targeting agent used in combination with the bioluminescence; the medium in which the reaction is run; stability of the components, such as temperature or pH sensitivity; shelf life of the components; sustainability of the light emission, whether constant or intermittent; availability of components; desired light intensity; color of the light; and other such factors. Such bioluminescence generating systems are known (those described in U.S. Pat. Nos. 5,876,995; 6,152,358; and 6,113,886).

LanFPs can be combined with components of bioluminescence generating reactions in order to enhance or alter the color of the resulting bioluminescence. Such a system that includes fluorescent proteins and bioluminescence generating components is described in U.S. Patent Application 2005/0272111A1 and incorporated herein by reference.

1. Luciferases

The protein that catalyzes or initiates the bioluminescent reaction is referred to as a luciferase, and the oxidizable substrate is referred to as luciferin as defined and described in U.S. Patent Application 2005/0272111A1. Luciferases refer to any compound that, in the presence of any necessary activators, catalyze the oxidation of a bioluminescence substrate (luciferin) in the presence of molecular oxygen, whether free or bound, from a lower energy state to a higher energy state such that the substrate, upon return to the lower energy state, emits light. Luciferins are the substrates for the reaction or for inclusion in the conjugates and include any molecule(s) with which the luciferase reacts to produce light. The bioluminescent generating systems also require additional components known to those of skill in the art such as molecular oxygen, ATP, flavin reductase, $Ca^{2\pm}$, or other suitable metal ion. The desired production of light results from the reaction of combining all components of a bioluminescent generating system, therefore, all but one component, either the luciferase or luciferin, will be mixed or packaged with or otherwise combined. A LanFP can be included with at least one component of a bioluminescence generating system as described in U.S. Patent Application 2005/0272111A1 and used in the methods described therein. Such methods include use in conjunction with diagnostic systems for the in vivo detection of neoplastic tissues and other tissues, use in luminescent novelty items, immunoassays, FRET and FET assays, multi-well assay devices and other methods in which luciferases are used including, but not limited to those described in U.S. application Ser. Nos. 08/757,046; 08/597,274; 08/990,103 and U.S. Pat. No. 5,625,048; International Patent Application Publication Nos. WO 95/21191; WO 96/23810; WO 97/26333; WO 97/28261; WO 97/41228; WO 98/02571 and all incorporated herein by reference.

K. Kits

The present invention provides utility kits for use in practicing one or more of the above described applications are provided, where the subject kits typically include elements for making the subject proteins, e.g., a construct comprising a vector that includes a coding region for the subject protein. The subject kit components are typically present in a suitable storage medium, e.g., buffered solution, typically in a suitable container. Also present in the subject kits may be antibodies to the provided protein. The kits may comprise a plurality of different vectors each encoding the subject protein, where the vectors are designed for expression in different environments and/or under different conditions. Exemplary vectors include, but are not limited to, constitutive expression where the vector includes a strong promoter for expression in mammalian cells, or a promoterless vector with a multiple cloning site for custom insertion of a promoter and tailored expression.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, such as a piece or pieces of paper on which the information is printed, in the packaging of the kit, or in a. package insert. Yet another means would be a computer readable medium, such as diskette, or CD, on which the information has been recorded. Further, another means by which the instructions may be present is a website address used via the internet to access the information at a removed site. Any convenient means may be present in the kits.

The components of the kits may be packaged either in aqueous media or in lyophilized form. The container means of the kits will generally include at least one vial, test tube, flask, bottle, syringe or other container means, into which the described reagents may be placed, and preferably, suitably aliquoted. Where a second or third LanFP or additional component is provided, the kit will also generally contain a second, third or other additional container into which this ligand or component may be placed.

The kits of the present invention will also typically include a means for containing the reagent containers in close confinement for commercial sale. Such containers may include injection or blow-molded plastic containers into which the desired vials are retained.

DEFINITIONS

Unless defined otherwise, all technical and scientific terms used herein have the meaning commonly understood by a person skilled in the art to which this invention belongs. Standard recombinant DNA, molecular cloning, and immunology techniques that are used herein are well known in the art and are described more fully in Sambrook, J., Fritsch, E. F. and Maniatis, T. Molecular Cloning: A Laboratory Manual; Cold Spring Harbor Laboratory Press: Cold Spring Harbor, 1989 and Ausubel, et al., eds., Current Protocols in Molecular Biology, John Wiley & Sons, Inc., 1997. All patents and publications referred to herein are incorporated by reference to the extent that they provide exemplary procedural or other details supplementary to those set forth herein.

An "amino acid (aminocarboxylic acid)" is a component of proteins and peptides. All amino acids contain a central carbon atom to which an amino group, a carboxyl group, and a hydrogen atom are attached. Joining together amino acids forms polypeptides. "Polypeptides" are molecules containing up to 1000 amino acids. "Proteins" are polypeptide polymers containing 50 or more amino acids.

A "gene" is a hereditary unit that has one or more specific effects upon the phenotype of the organism; and the gene can mutate to various allelic forms. The gene is generally comprised of DNA.

The term "variant" relates to nucleotide or amino acid sequences which have similar sequences and that function in the same way.

A "host" is a cell or organism that receives a foreign biological molecule, including a genetic construct or antibody, such as a vector containing a gene.

A "nucleotide sequence" or "nucleic acid molecule" is a nucleotide polymer including genes, gene fragments, oligonucleotides, polynucleotides, and other nucleic acid sequences. "Nucleic acid" refers to the monomeric units from which DNA or RNA polymers are constructed, wherein the unit consists of a purine or pyrimidine base, a pentose, and a phosphoric acid group.

"Plasmids" are double-stranded, closed DNA molecules. Plasmids or "expression vectors" can contain coding sequences for expression machinery such as promoters, poly-A tails, stop codons, and other components necessary for expression of an inserted gene. Plasmids are used as vectors for transfecting a host with a nucleic acid molecule.

A "vector" is a replicon, such as plasmid, phage or cosmid, to which another DNA segment may be attached so as to bring about the replication of the attached segment.

"Wild type" is the most frequently observed phenotype in a population, or the one arbitrarily designated as "normal." Often symbolized by "+" or "Wt." The Wt phenotype is distinguishable from mutant phenotype variations.

A "population of cells" includes any cell or group of cells. A population of cells may include one or more stem cells and/or one or more progeny cells of a stern cell. Such population of cells can comprise a cell in culture, comprise in vitro tissue, or comprise a tissue within a living organism. The population of cells may be mammalian and includes, but is not limited to, murine, human, bovine, porcine, equine, ovine, or canine.

The term "identifying" refers to the detection of a label or marker, recognizing the difference between labeled and unlabeled cells. Identifying the label or marker is not limited to visual identity. It also includes separation without visual identity.

The term "harmonization" or "harmonizing" or their variants refer to altering the nucleotide codons encoding specific amino acids to those more likely to be used in the host cell or organism without altering the encoded amino acid.

The terms "tag" or "tagged" refer to linking proteins of interest with a detectable marker such as a fluorescent protein, his tag, myc tag, or FLAG tag. These detectable markers are small and easily detected by immunodetection techniques or fluorescent techniques.

As used herein, the term "protein of interest" refers to a protein for which expression is desired. For example, the term encompasses any recombinant forms of a protein that is desired. Such proteins may include proteins desired to be visualized in vivo or in vitro during expression.

As used herein, the term "fluorescently labeled" means, when referring to a polypeptide, that the polypeptide is covalently attached to a fluorescent moiety. A polypeptide may be fluorescently labeled by covalent attachment to a non-polypeptide fluorescent dye, or alternatively, by expression as a fusion protein with a fluorescent polypeptide.

As used herein, the term "linker sequence" refers to a sequence of peptide bonded amino acids that joins or links by peptide bonds two amino acid sequences or polypeptide domains that are not joined by peptide bonds in nature. A linker sequence is encoded in frame on a polynucleotide between the sequences encoding the two polypeptide domains joined by the linker. A linker is preferably 5 to 50 amino acids in length, more preferably 10 to 20 amino acids in length. Examples of linkers useful in the invention are the Gly-Ala linkers taught by Huston et al., U.S. Pat. No. 5,258, 498, incorporated herein by reference. Additional useful linkers include, but are not limited to (Arg-Ala-Arg-Asp-Pro-Arg-Val-Pro-Val-Ala-Thr)1-5 (SEQ ID NO: 32); Xu et al., 1999, Proc. Natl. Acad. Sci. U.S.A. 96: 151-156), (Gly-Ser)n (Shao et al., 2000, Bioconjug. Chem. 11: 822-826), (Thr-Ser-Pro)n (Kroon et al, 2000, Eur. 3. Biochem. 267: 6740-6752), (Gly-Gly-Gly)n (Kluczyk et al., 2000, Peptides 21: 1411-1420), and (Glu-Lys)n (Kluczyk et al., 2000), wherein n is 1 to 15.

A "DNA molecule" refers to the polymeric form of deoxyribonucleotides (adenine, guanine, thymine, or cytosine) in either single stranded form or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes.

A DNA "coding sequence" is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and synthetic DNA sequences. A polyadenylation signal and transcription termination sequence may be located 3' to the coding sequence.

As used herein, the term "hybridization" refers to the process of association of two nucleic acid strands to form an antiparallel duplex stabilized by means of hydrogen bonding between residues of the opposite nucleic acid strands.

The term "oligonucleotide" refers to a short. (under 100 bases in length) nucleic acid molecule.

"DNA regulatory sequences", as used herein, are transcriptional and translational control sequences, such as promoters, enhancers, polyadenylation signals, terminators, and the like, that provide for and/or regulate expression of a coding sequence in a host cell.

A "promoter sequence" is a DNA regulatory region capable of being bound by RNA polymerase, whereby the polymerase initiates transcription of a downstream (3' direction) coding sequence. For purposes of defining the present invention, the promoter sequence includes the minimum number of bases or elements necessary to initiate transcription at levels detectable above background. Within the promoter sequence will be found a transcription initiation site, as well as protein binding domains responsible for the binding of RNA polymerase. Various promoters, including inducible promoters, may be used to drive the various vectors of the present invention.

As used herein, the terms "restriction endonucleases" and "restriction enzymes" refer to enzymes that cut double-stranded DNA at or near a specific nucleotide sequence.

A cell has been "transformed" or "transfected" by exogenous or heterologous DNA when such DNA has been introduced inside the cell. The transforming DNA may or -may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, heterologous DNA includes coding sequence in a construct where portions of genes from two different sources have been brought together so as to produce a fusion protein product. Allelic variations or naturally-occurring mutational events do not give rise to a heterologous region of DNA as defined herein.

As used herein, the term "reporter gene" refers to a coding sequence attached to a promoter or enhancer elements and whose product may be assayed easily and quantifiably when the construct is introduced into tissues or cells.

The amino acids described herein are preferred to be in the "L" isomeric form. The amino acid sequences are given in one-letter code (A: alanine; C: cysteine; D: aspartic acid; E: glutamic acid; F: phenylalanine; G: glycine; H: histidine; I: isoleucine; K: lysine; L: leucine; M: methionine; N: asparagine; P: proline; Q: glutamine; R: arginine; S: serine; T: threonine; V: valine; W: tryptophan; Y: tyrosine; X: any residue).

The term "specific binding," in the context of antibody binding to an antigen, is a term well understood in the art and refers to binding of an antibody to the antigen to which the antibody was raised, but not other, unrelated antigens.

As used herein the term "isolated" is meant to describe a polynucleotide, a nucleic acid, a protein, a polypeptide, an antibody, or a host cell that is in an environment different from that in which the polynucleotide, nucleic acid, protein, polypeptide, antibody, or host cell naturally occurs. In reference to a sequence, such as nucleic acid or amino acid, "isolated" includes sequences that are assembled, synthesized, amplified, or otherwise engineered by methods known in the art.

"Bioluminescence" (BL) is defined as emission of light by living organisms that is well visible in the dark and affects visual behavior of animals (e.g., Harvey, E. N. (1952). Bioluminescence. New York: Academic Press; Hastings, J. W. (1995). Bioluminescence. In: Cell Physiology (ed. by N. Speralakis). pp. 651-681. New York: Academic Press; Wilson, T. and Hastings, J. W. (1998). Bioluminescence. Annu Rev Cell Dev Biol 14, 197-230). Bioluminescence does not include so-called ultra-weak light emission, which can be detected in virtually all living structures using sensitive luminometric equipment (Murphy, M. E. and Sies, H. (1990).

As used herein, the phrase "stringent hybridization conditions" refers to conditions under which a probe, primer or oligonucleotide will hybridize to its target sequence, but to no other sequences. Stringent conditions are sequence-dependent and will be different in different circumstances. Longer sequences hybridize specifically at higher temperatures than shorter sequences. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present in excess at Tm, 50% of the probes are occupied at equilibrium. Typically, stringent conditions will be those in which the salt concentration is less than about 1.0 M. sodium ion, typically about 0.01 to 1.0 M sodium ion (or other salts) at pH 7.0 to 8.3 and the temperature is at least about 30° C. for short probes, primers or oligonucleotides (e.g., 10 nt to 50 nt) and at least about 60° C. for longer probes, primers and oligonucleotides. Stringent conditions may also be achieved with the addition of destabilizing agents, such as formamide Preferably, the conditions are such that sequences at least about 65%, 70%, 75%, 85%, 90%, 95%, 98%, or 99% homologous to each other typically remain hybridized to each other.

As used herein, the term "specific binding pair" refers to a pair of polypeptides that physically interact in a specific manner that gives rise to a biological activity, that is, to the substantial exclusion of other polypeptides. Members of a specific binding pair interact through complementary interaction domains. Non-limiting examples of specific binding pairs include antibody-antigen pairs, enzyme-substrate pairs, dimeric transcription factors (e.g., AP-1, composed of Fos specifically bound to Jun via a leucine zipper interaction domain) and receptor-ligand pairs.

The term "identity" in the context of sequences refers to the relatedness of two sequences on a nucleotide-by-nucleotide basis or amino acid-by-amino acid basis over a particular comparison window or segment. Thus, identity is defined as the degree of sameness, correspondence, or equivalence between the same strands (either sense or antisense) of two DNA segments or the primary structure of two polypeptides.

"Similarity" between two amino acid sequences is defined as the presence of a series of identical as well as conserved amino acid residues in both sequences. The higher the degree of similarity between two amino acid sequences, the higher the correspondence, sameness or equivalence of the two sequences. "Identity between two amino acid sequences" is defined as the presence of a series of exactly alike or invariant amino acid residues in both sequences. The percentage of sequence identity is calculated by comparing two optimally aligned sequences over a particular region, determining the number of positions at which the identical base occurs in both sequence in order to yield the number of matched positions, dividing the number of such positions by the total number of positions in the segment being compared and multiplying the result by 100. Optimal alignment of sequences may be conducted by the algorithm of Smith & Waterman, Appl. Math. 2:482 (1981), by the algorithm of Needleman & Wunsch, J. Mol. Biol. 48:443 (1970), by the method of Pearson & Lipman, Proc. Natl. Acad. Sci. (USA) 85:2444 (1988) and by computer programs which implement the relevant algorithms (e.g., Clustal Macaw Pileup, FASTDB (Intelligenetics), BLAST (National Center for Biomedical Information; Altschul et al., Nucleic Acids Research 25:3389 3402 (1997)), PILEUP (Genetics Computer Group, Madison, Wis.) or GAP, BESTFIT, FASTA and TFASTA (Wisconsin Genetics Software Package Release 7.0, Genetics Computer Group, Madison, Wis.). (U.S. Pat. No. 5,912,120.)

For purposes of the present invention, "complementarity" is defined as the degree of relatedness between two DNA segments. It is determined by measuring the ability of the sense strand of one DNA segment to hybridize with the antisense strand of the other DNA segment, under appropriate conditions, to form a double helix. In the double helix, adenine appears in one strand, thymine appears in the other strand. Similarly, wherever guanine is found in one strand, cytosine is found in the other. The greater the relatedness between the nucleotide sequences of two DNA segments, the greater the ability to form hybrid duplexes between the strands of the two DNA segments.

The terms "homology", "homologous" "substantially similar" and "corresponding substantially" are used interchangeably. They refer to sequence fragments, nucleic acid or amino acid, wherein changes in one or more bases or residues does not affect the ability of the fragment to result in a specific functional protein. These terms also refer to modifications of the nucleic acid or amino acid sequences of the instant invention such as deletion or insertion of one or more nucleotides or residues that do not substantially alter the functional properties of the resulting sequence relative to the initial, unmodified sequence. It is therefore understood, as those skilled in the art will appreciate, that the invention encompasses more than the specific exemplary sequences.

The term "operably linked" or "operatively linked" refers to the association of nucleic acid sequences on a single nucleic acid fragment so that the function of one is regulated by the other or is not hindered by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, two proteins can be operably linked, such that the function of either protein is not compromised. Generally, operably linked means that the nucleic acid sequences being linked are contiguous and, where necessary to join two protein coding regions, contiguous and in the same reading frame.

The term "expression", as used herein, refers to the production of a functional end-product.

The terms "hybrid antibody", "humanized antibody" and "chimeric antibody" are used interchangeably to refer to antibodies made using recombinant DNA technology that recognize human polypeptides but are only partially based on human DNA. For example, using recombinant DNA technology, DNA that encodes the binding portion of monoclonal mouse antibodies is merged with human antibody producing DNA. Mammalian cell culture is then used to express this DNA and produce half-mouse and half-human antibodies, i.e. chimeric or humanized antibodies.

By "substantially the same length" is meant that any difference in length does not exceed about 20%, usually does not exceed about 10% and more usually does not exceed about 5%; and have sequence identity to any of these sequences of at least about 80%, 85%, 90%, 95%, and usually at least about 99% over the entire length of the nucleic acid.

The term "polypeptide composition" as used herein refers to both the full-length protein, as well as portions or fragments thereof. Also included in this term are variations of the naturally occurring protein, where such variations are homologous or substantially similar to the naturally occurring protein, and mutants of the naturally occurring proteins, as described herein.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Identification of the Novel Fluorescent Protein LanFP1

Branchiostoma fluorescent proteins were first identified from searching genome databases with the sequence of GFP in an attempt to discover unknown sources of fluorescent proteins. LanFP1 was discovered by searching the est_others division of NCBI Expressed Sequence Tags (EST) database, using TBLASTN routine of the BLAST suite (Altschul et al., 1997) and queried with the entire coding sequence of Aequorea victoria jellyfish GFP. The TBLASTN parameters were set as follows: the low-complexity filter was turned off; the default expect was set at 10; and the default word size was set at 3. The search resulted in the identification of 13 Branchiostoma ESTs (Table 3) sharing identity with the coding sequence of GFP. Regions of each identified EST sharing identity with GFP were assembled in silica to generate the coding sequence of LanFP1. The assembled nucleic acid sequence was synthesized by methods known in the art. The 732 bp transcript assembled from Lancelet (SEQ ID NO: 25) contained an open reading frame of 219 amino acids (SEQ ID NO: 1) starting from position 1 to 657 followed by a stop codon.

TABLE 3

ESTs For Assembly of LanFP1.

| EST | Position On Contig |
|---|---|
| gi_66511577_gb_BW893733.1_BW893733 | 27 –> 838 |
| gi_66485022_gb_BW870345.1_BW870345 | 16 –> 639 |
| gi_66486915_gb_BW872238.1_BW872238 | 16 –> 621 |
| gi_66512171_gb_BW894220.1_BW894220 | 16 –> 687 |
| gi_66495717_gb_BW881040.1_BW881040 | 16 –> 671 |
| gi_66327586_gb_BW740938.1_BW740938 | 14 –> 647 |
| gi_66513502_gb_BW895120.1_BW895120 | 13 –> 691 |
| gi_66320303_gb_BW733673.1_BW733673 | 12 –> 667 |
| gi_66323004_gb_BW736374.1_BW736374 | 10 –> 660 |
| gi_66512397_gb_BW894392.1_BW894392 | 10 –> 690 |
| gi_66318139_gb_BW731527.1_BW731527 | 13 –> 642 |
| gi_66406234_gb_BW798018.1_BW798018 | 6 –> 650 |
| gi_30921604_gb_B1386699.1_B1386699 | 0 –> 648 |

Known fluorescent protein coding sequences were used to identify sequences motifs in other organisms. Assembling the identified sequences resulted in the generation of a new fluorescent protein derived from a source phylogenetically closer than those sources from which known fluorescent proteins have been derived.

Example 2

Analysis of LanFP1 Coding Sequence

The assembled coding sequence of LanFP1 (SEQ ID NO. 25) showed variations in overlapping ESTs from the database at positions 133, 442, 472, 503, 533, and 603. To resolve these variations, the assembled sequence was compared to several other sequence types. The most likely conserved amino acid or nucleotide, based on Branchiostoma floridae codon usage, consensus in other known fluorescent proteins, and/or amino acid properties, was ultimately used for the variant positions. For example, position 133 in the coding sequence showed a variation between Guanine and Cytosine resulting in the coding of either an Alanine or Proline amino acid. According to protein conservation, Alanine is supported therefore Guanine was chosen. The variation at position 442 consisted of either an Adenine or Guanine. While the protein conservation supported Asparagine, three consecutive Asparagines are unusual. Adenine was chosen to encode Asparagine, since it was the most likely conserved amino acid for this position. The variation at position 472 consisted of AGT encoding Serine or ACC encoding Threonine. The nucleotides encoding Serine were chosen due to the bulkiness of the neighboring amino acids. The variation at position 503 consisted of a Guanine encoding Arginine or Adenine encoding Lysine. Protein conservation supported using Guanine to encode Arginine. The variation at position 533 consisted of an Adenine encoding Aspartic Acid or Guanine encoding Glycine. Protein conservation supported using Adenine to encode Aspartic Acid. The variation at position 603 consisted of Thymine encoding Serine or Adenine encoding Threonine. Protein conservation supported using Thymine to encode Serine.

The identification of the above-described variations indicated a tolerance by the coding sequence for alterations that do not alter the fluorescing properties of the encoded protein. As such, alterations may be generated at the above-described locations without altering fluorescent properties, but. possibly altering other characteristics such as protein stability, tolerance, or temperature sensitivity.

Example 3

Harmonizing Branchiostoma Fluorescent Protein Sequence

Each species has a tendency to use certain codons to encode a specific amino acid over other codons encoding the same amino acid. A host may not efficiently translate proteins having a coding sequence that does not use those codons likely used by the host. Harmonizing a coding sequence involves altering the nucleotide sequence, but not the amino acid sequence, such that the codons encoding the amino acid sequence are those most likely used by the host; thus, providing optimum expression capability in a host of interest, and minimizing poor translation efficiency. To harmonize the codons of LanFP1, for expression in mouse and other mammalian systems, the coding DNA sequence was back. translated from the predicted 219-amino acid peptide using a standard mouse codon set. The resulting muranized DNA sequence (SEQ ID NO: 22) is 76% identical to the original assembled transcript (SEQ ID NO: 25) from 1-657 base pairs (FIG. 1). The non-coding sequence in the original transcript was not included in the optimization and DNA synthesis. In order to facilitate subsequent cloning steps, restriction sites HindIII and BamHI at 5' and 3' ends of the 657 base pair sequence, respectively, were included. A stop codon was also included after the BamHI site in the initial submission of DNA sequence for synthesis. This stop codon was not incorporated into the final plasmid vector since it was eliminated during cloning. The synthesized gene was cloned into the commercially available p3XFlag-Myc-CMV plasmid HindIII and BamHI sites, which contained 5' and 3' tags plus a stop codon on the vector backbone.

Example 4

Expressing *Branchiostoma* Fluorescent Proteins in Mammalian Cells

Figure 3:
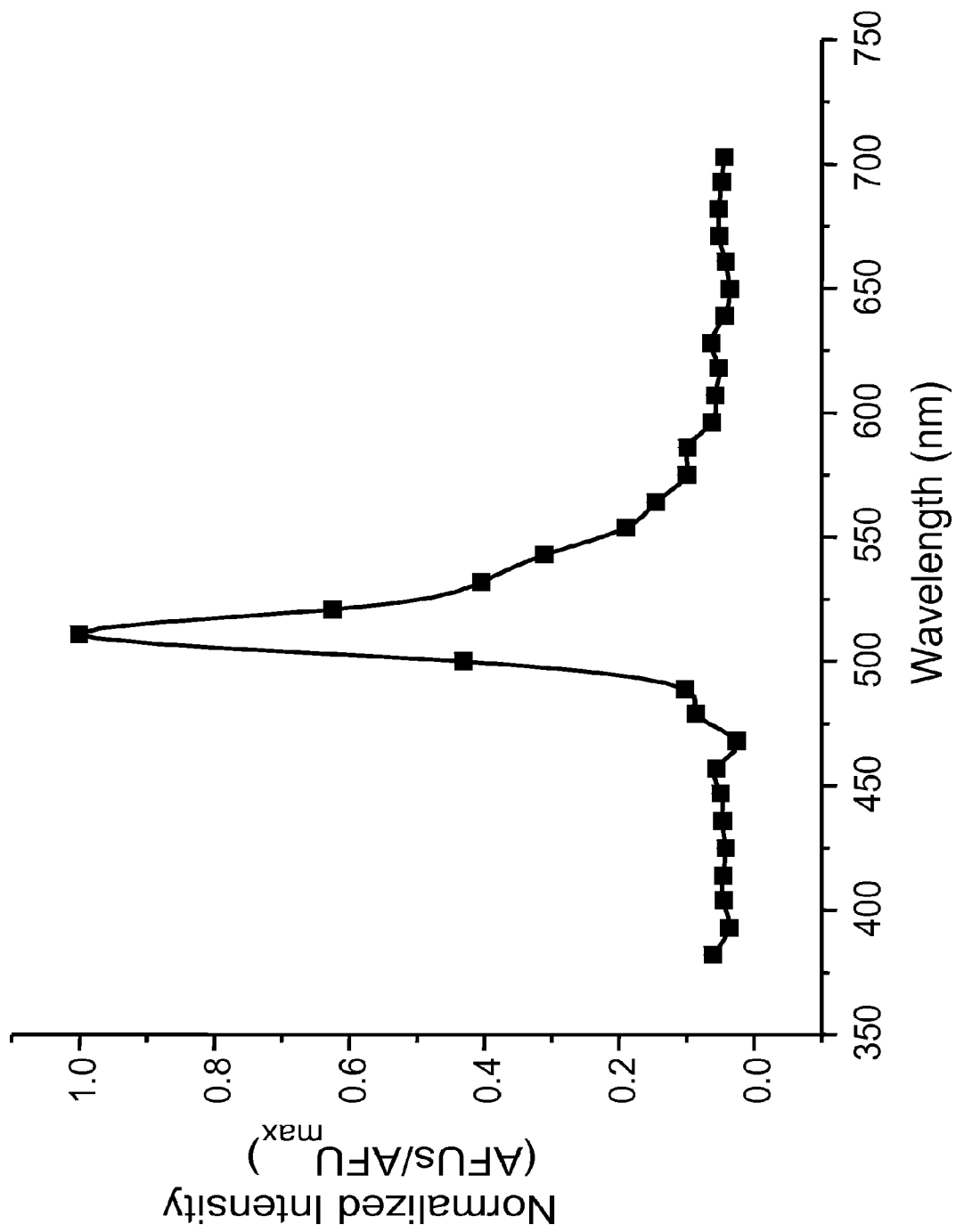
FIG. 3 graphically shows the LanFP1 spectra from HEK-293 cells transfected with an expression vector encoding muranized LanFP1 (SEQ ID NO: 22), and demonstrates the maximum fluorescence in the green spectral range (λ.max~520 nm). HEK-293 cells expressing muranized LanFP1 were examined using spectral detection on a Zeiss LSM 510 META system.

The harmonized LanFP1 (SEQ ID NO: 22) of Example 3 was expressed in HEK-293 human embryonic kidney cells. HEK-293 cells cultured in minimum essential media (MEM) supplemented with 5% fetal bovine serum (FBS) and 2 mM glutamine were plated 24 to 48 hours prior to transfection on 25 mm round coverslips coated with poly-D lysine. HEK-293 cells were transiently transfected with muranized LanFP1 cloned into the p3Xflag-Myc-CMV plasmid using a combination of the Nupherin (Biomol Research Laboratories, Plymouth Meeting, Pa.) and LipofectAMINE 2000 (Invitrogen) transfection reagents. Specifically, 2 μg of plasmid DNA was mixed with 12 μg of Nupherin in 300 μl of MEM containing no FBS or antibiotics for 15 minutes (min) and then combined with 300 μl of MEM containing 6 μl of LipofectAMINE 2000 for another 15 min at room temperature. The culture media was replaced with 600 μl of transfection media containing the LipofectAMINE-Nupherin-DNA. complex. After incubating for 0.5 to 1 hour, transfection media was replaced with 2 ml of culture media. Cells expressing muranized LanFP1 were imaged using confocal microscopy (FIG. 2). The LanFP1 spectra demonstrated a maximum fluorescence in the green range (λmax~520 nm) (FIG. 3).

Figure 4:
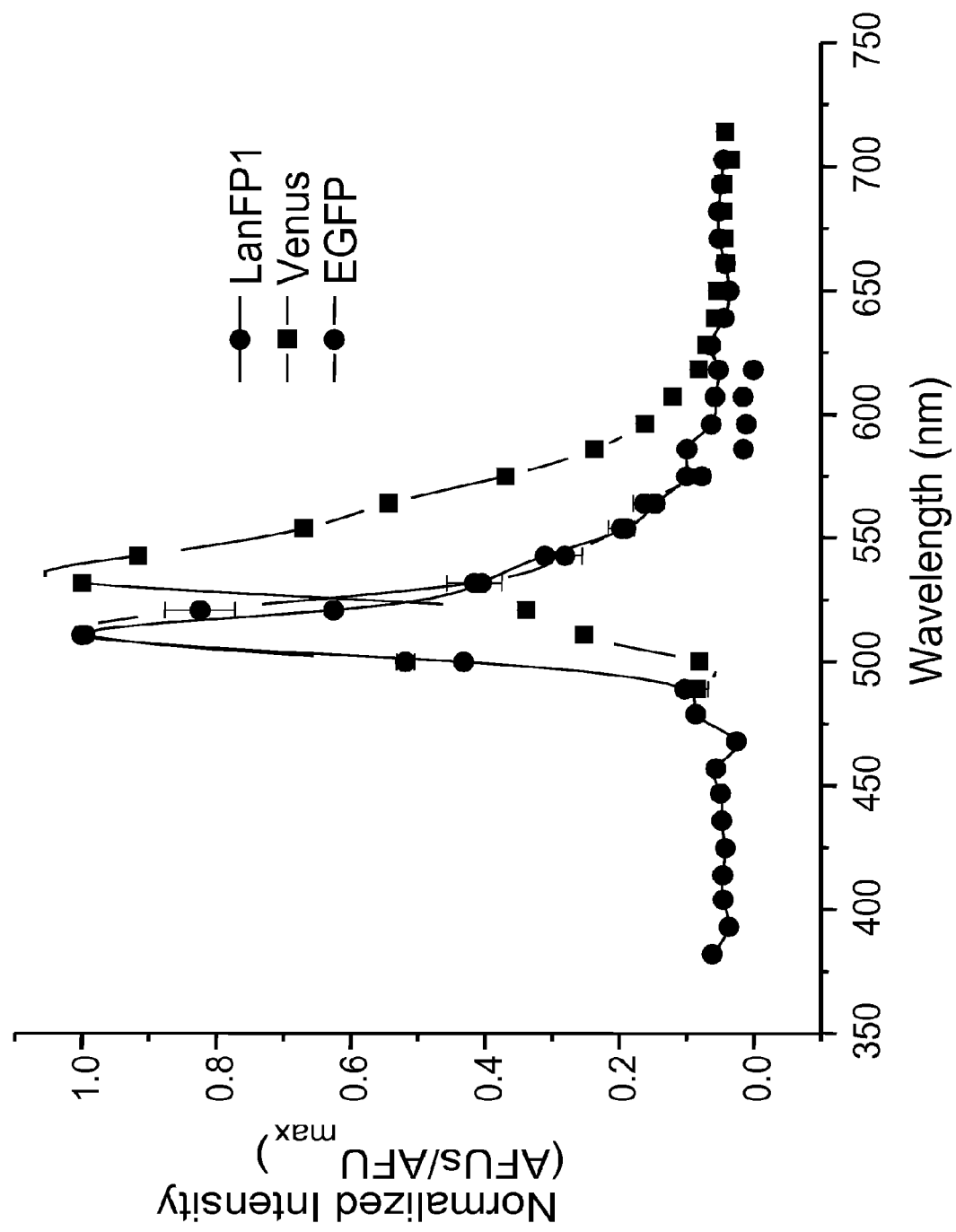
FIG. 4 illustrates the muranized LanFP1 spectra (circle, solid line) compared to the spectra of *Aequorea* derived counterparts EGFP, a green variant (circle, dashed line), and Venus, a yellow variant (square, dashed line).
Figure 5:
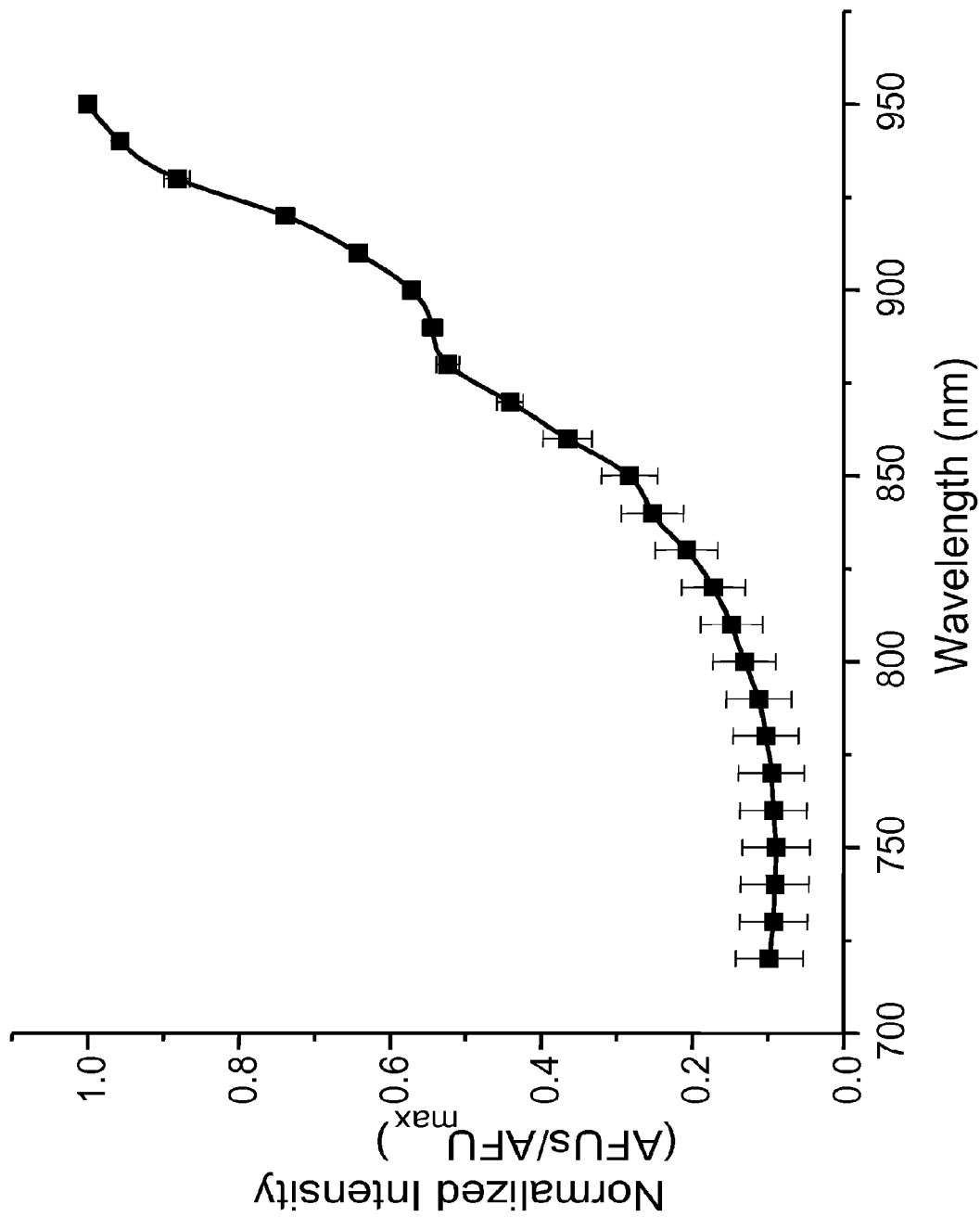
FIG. 5 shows that muranized LanFP1 expressed in HEK-293 cells has a maximum excitation of about 950 nm when exposed to increasing two-photon excitation. A calibration curve was used to account for differential transmittance of the objective, and increasing intensity was used to monitor the normalized two-photon excitation (n=6±Standard error of the mean, s.e.m.).
Figure 6:
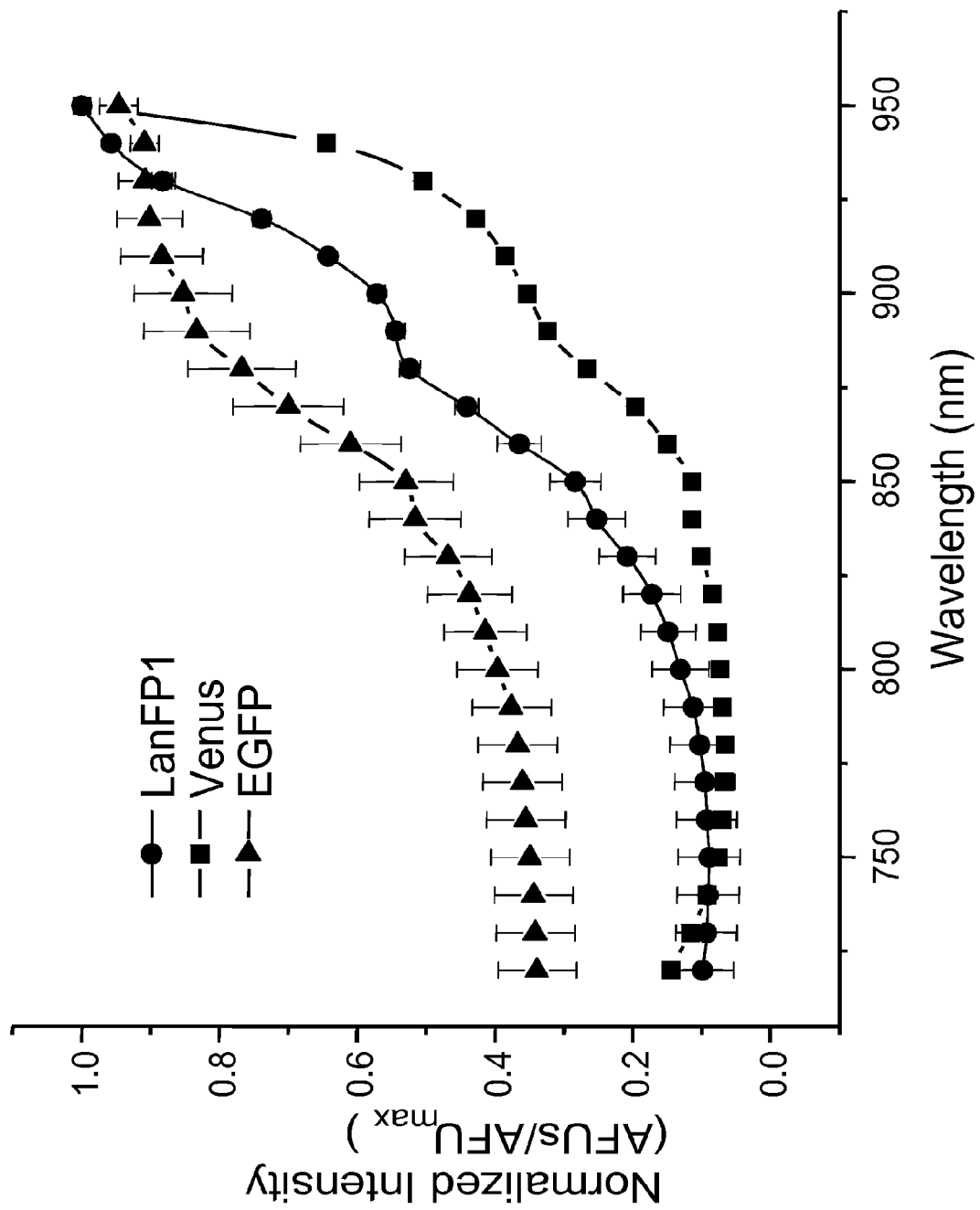
FIG. 6 shows that the excitation spectral of muranized LanFP1 (circle) falls between the excitation spectrals for EGFP (triangle) and Venus (square). HEK-293 cells expressing EGFP, Venus and muranized LanFP1 were all exposed to increasing two-photon wavelength. The spectra are connected for the objective transmittance, and normalized to maximum excitation (n>6±s.e.m.).

In comparison to other commercially available fluorescent proteins, LanFP1 has similar emission spectra to EGFP (FIG. 4). Muranized LanFP1 demonstrates more similarity in emission spectra to EGFP compared to Venus. Specifically, muranized LanFP1 excites efficiently with 458 nm, 488 nm and 514 nm (λmax=510+/−50 nm). HEK-293 cells expressing EGFP, Venus, and muranized LanFP1 were all imaged using spectral imaging on a Zeiss LSM 510 META system. The resultant spectra were normalized to the maximum fluorescence averaged over 10 cells. Using two-photon excitation, LanFP1 was found to have a maximum excitation at 950 nm (FIG. 5) and the excitation spectral for LanFP1 falls between *Aequorea* derived counterparts, EGFP and Venus (FIG. 6). The differing excitation spectral for LanFP I allows its use in combination with the two most widely used fluorescent proteins, EGFP and Venus.

Example 5

Analysis of *Branchiostoma* Fluorescent Proteins

Figure 7A:
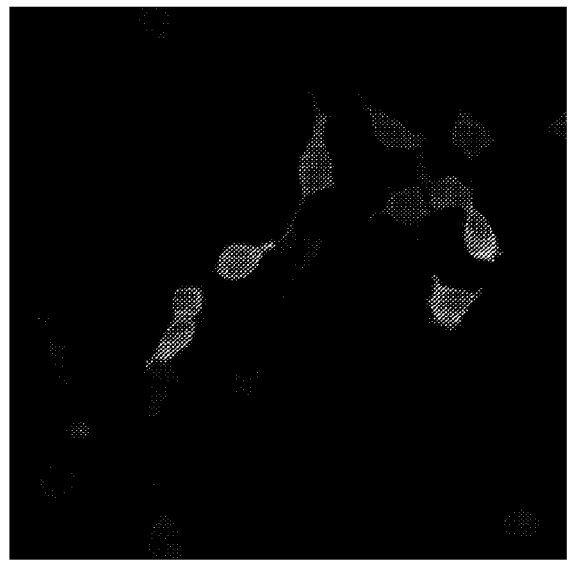
FIGS. 7A-D show that muranized LanFP1 is photo stabile. The ability to bleach muranized LanFP1 was evaluated by exposing LanFP1 expressing HEK-293 cells to increasing powers of 488 nm excitation. Muranized LanFP1 (green, FIG. 7A) does not demonstrate significant photobleaching between 1-6% laser power using a 6.1 Amp laser (FIG. 7B). Muranized LanFP1 (green, FIG. 7C) reached maximal photobleaching saturation at 50% laser power (FIG. 7D).
Figure 7B:
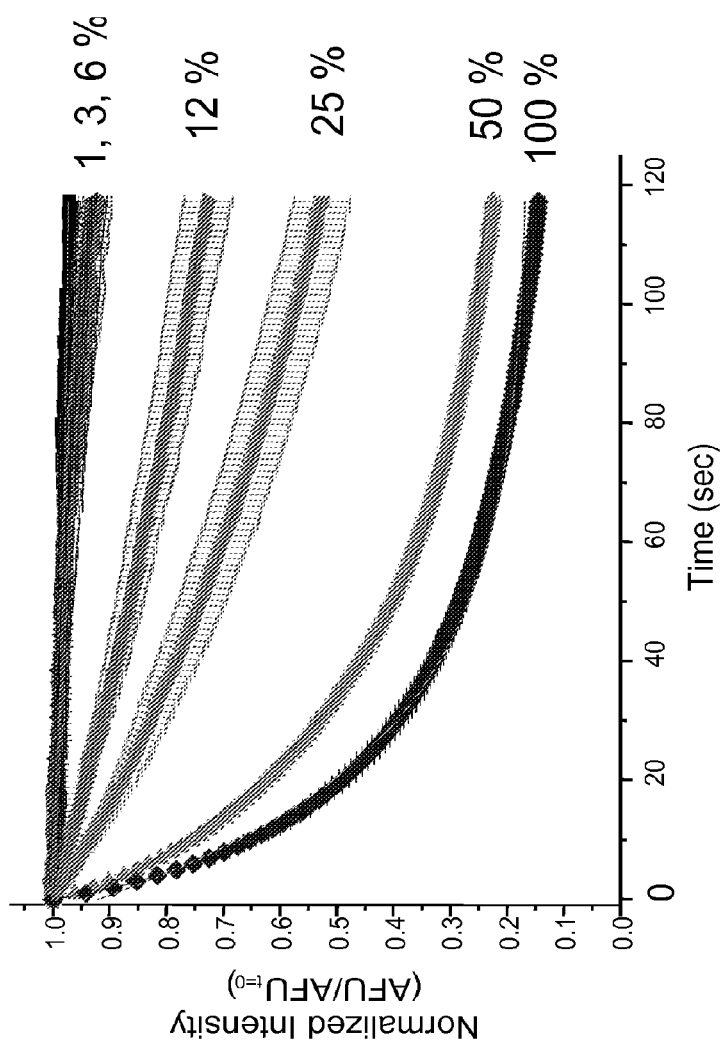
Figure 7D:
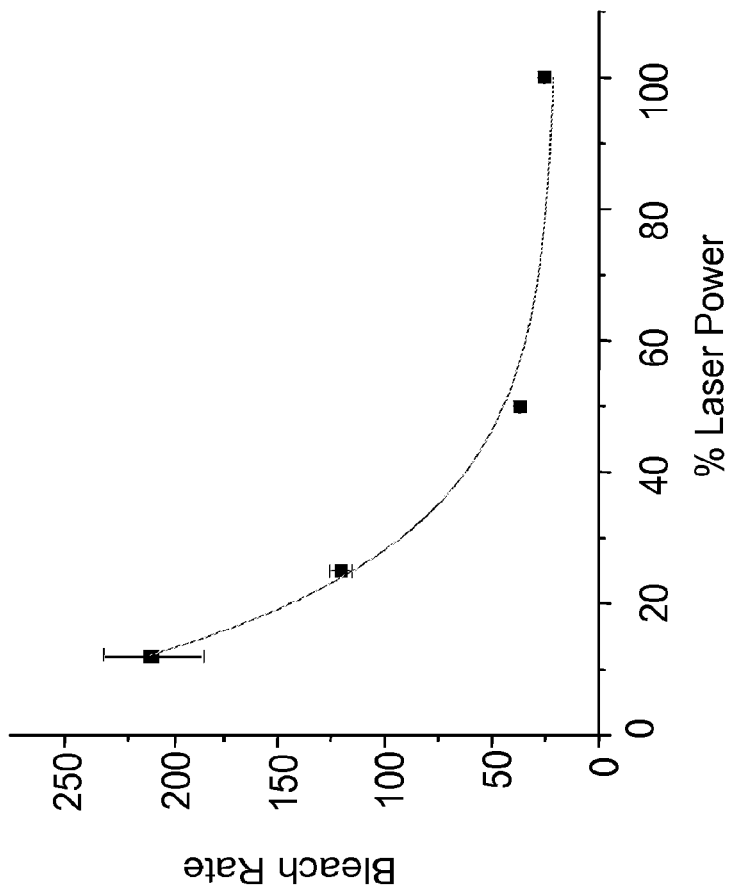
Figure 7C:
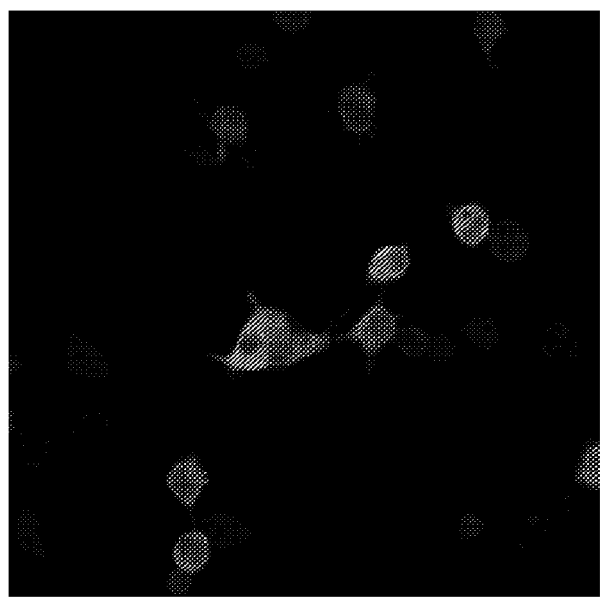

Photobleaching, which destroys the fluorescent molecule by exposure to high-intensity light, is often the limiting factor in fluorescent microscopy. LanFP1's resistance to photobleaching was analyzed by exposing LanFP1 expressing HEK-293 cells to increasing powers of 488=excitation using laser power between 1-6% of a 6.1 Amp laser. LanFP 1 did not demonstrate significant photo bleaching between 1-6% laser power using a 6.1 Amp laser (FIGS. 7A and 7B), but reached maximal photobleaching rate saturation at 50% laser power (FIGS. 7C and 7D).

Figure 8D:
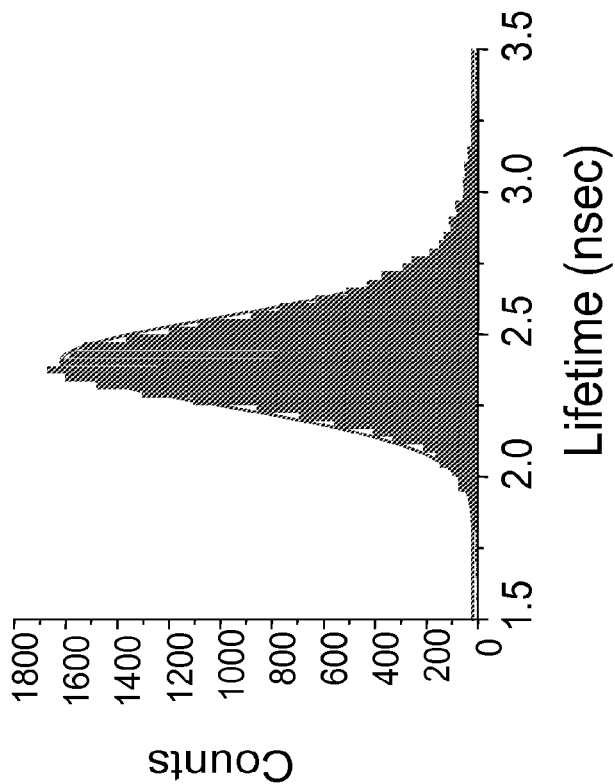
Figure 8C:
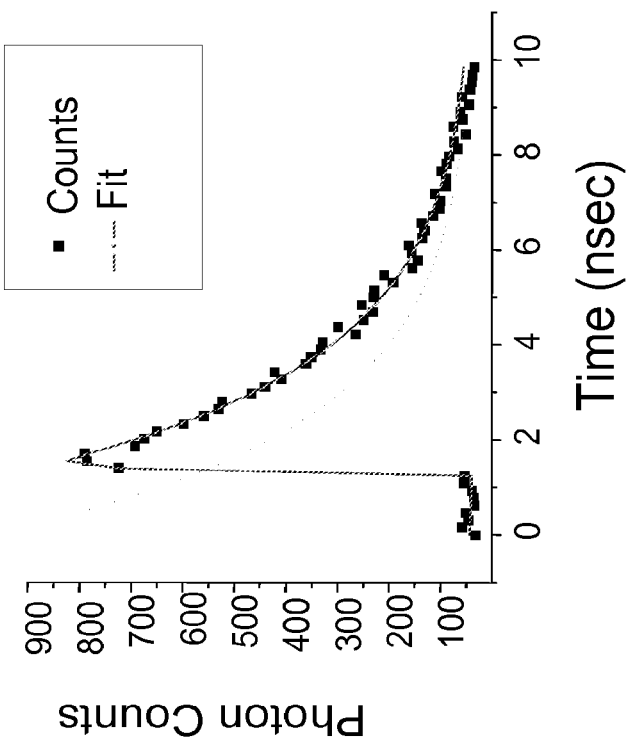
Figure 9B:
FIGS. 9A-B show images of the *Branchiostoma floridae* or Lancelet from which the nucleotide sequences of LanFP1 and LanFP3 (SEQ ID NO: 25 and SEQ ID NO: 27) were assembled and LanFP2 (SEQ ID NO: 26) was identified.
Figure 9A:
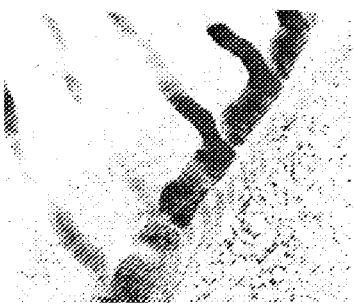
Figure 10A:
FIGS. 10A-C illustrate the bioluminescence of *Branchiostoma floridae*. The image of *Branchiostoma floridae* demonstrates the existence of two independent spectra (FIG. 10A). The green resultant spectra profile (FIG. 10B) is similar to the spectra of muranized LanFP1, but not an exact match. The red resultant spectra profile (FIG. 10C) is not similar to muranized LanFP1 (SEQ ID NO: 22), LanFP2 (SEQ ID NO: 23) or LanFP3 (SEQ ID NO: 24). The two independent spectra were analyzed by ACE (automated component extraction) using a META detection head on a Zeiss 510 confocal microscopy.
Figure 10C:
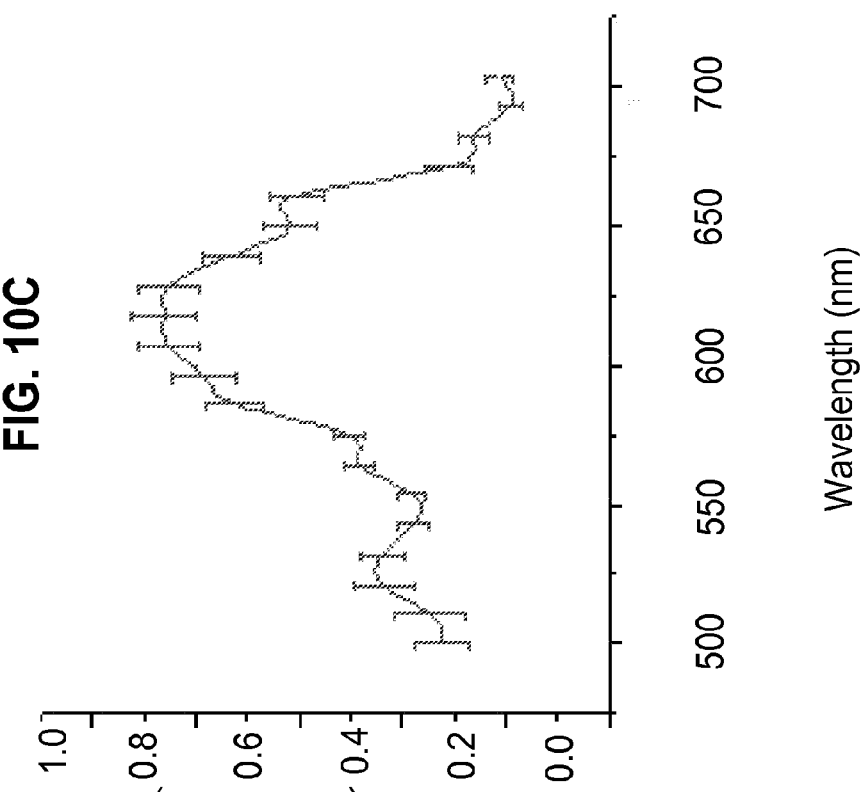
Figure 10B:
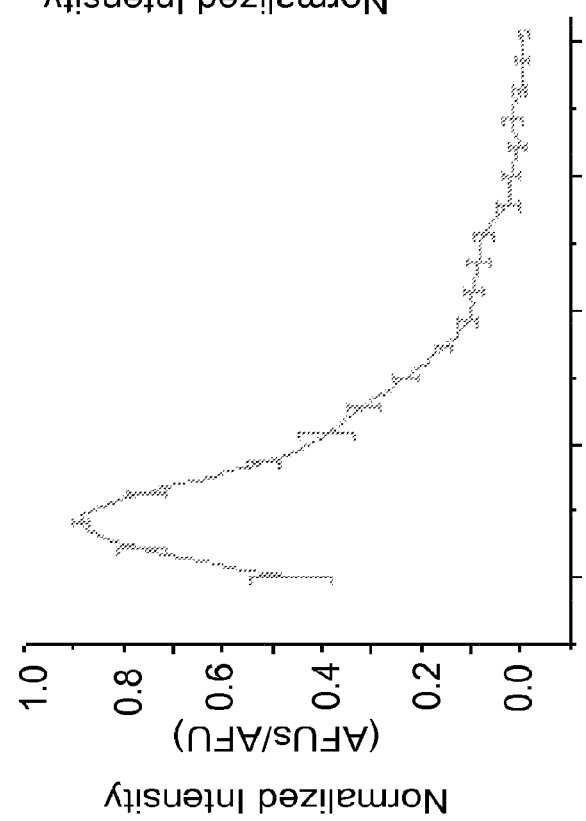
Figure 11:
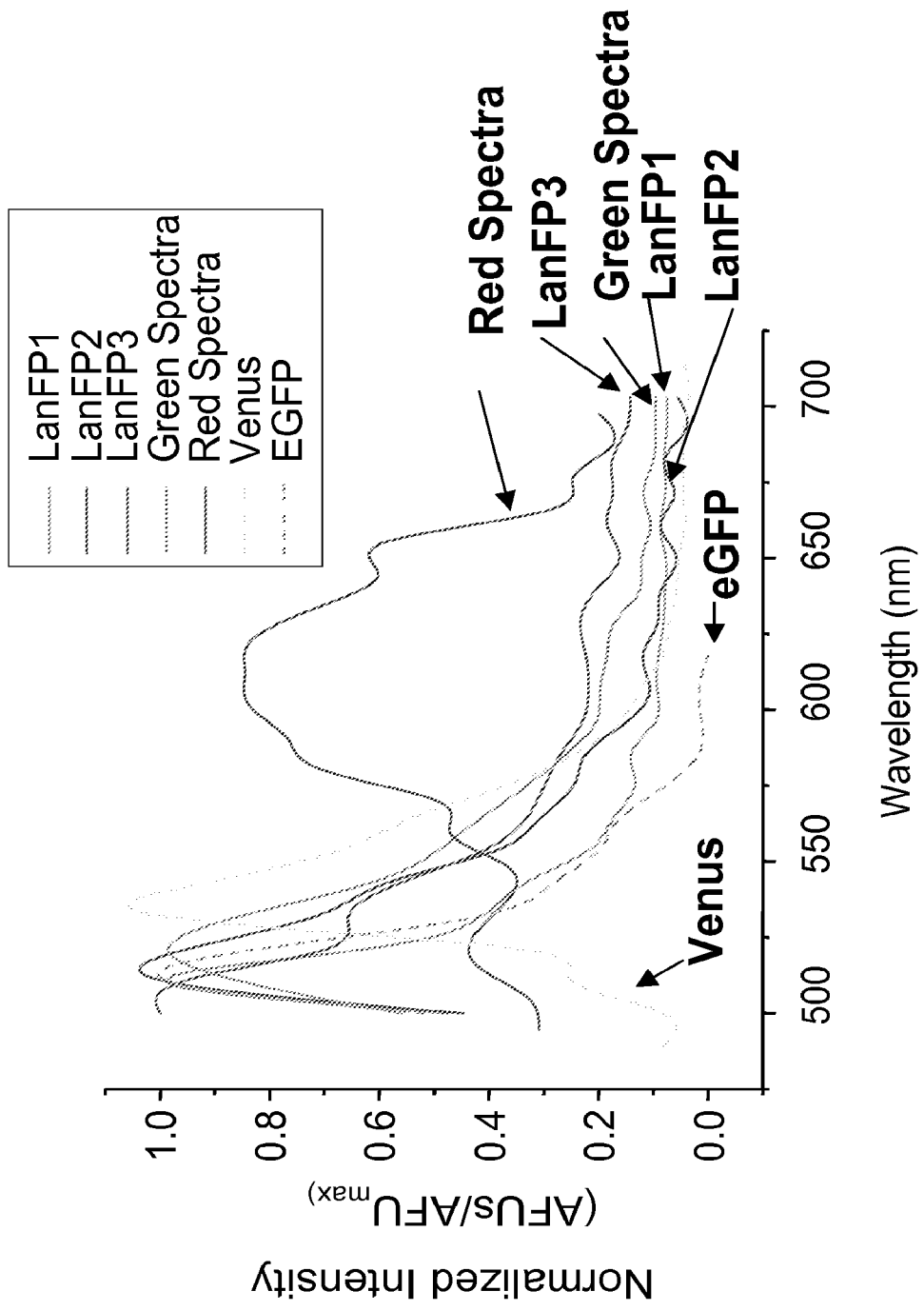
FIG. 11 graphically illustrates the fluorescence spectra of muranized LanFP1 (solid green line), muranized LanFP2 (solid dark green line), muranized LanFP3 (solid blue line), humanized *Aequorea* GFP (EGFP, green dashed line), endogenous Lancelet green spectra (green solid line), endogenous Lancelet red spectra (red solid line), and Venus (yellow dashed line). The spectra of muranized LanFP1, LanFP2 and LanFP3 are more similar to EGFP than Venus or native Lancelet red protein.

LanFP1 demonstrated significant variations in fluorescence intensity and only a single fluorescence lifetime. Fluorescence lifetime images were acquired using a Becker and Hickel acquisition card and a Zeiss LSM 510 META confocal system. The intensity image (FIG. 8A) and corresponding lifetime image (FIG. 8B) demonstrate significant variations in fluorescence intensity, but a single fluorescence lifetime. The resultant curves are fit to a single exponential decay (FIG. 8C), and the average pixel histogram for lifetimes (FIG. 8D) demonstrate that harmonized LanFP1 has a lifetime of about 2.5 nanoseconds.

The properties of LanFP1 are similar to those of GFP. The relative resistance to photobleaching and average lifetime make LanFP1 a suitable probe that may be used easily in place of GFP.

Example 6

Identification of Additional LanFPs

Once the LanFP1 sequence was assembled, it was then used as the query sequence to search the *Branchiostoma* EST database for other potential fluorescent proteins. Five additional proteins that may be potential fluorescent proteins were identified including LanFP2 (SEQ ID NO: 2), LanFP3 (SEQ ID NO: 3), LanFP4 (SEQ ID NO: 29), LanFP5 (SEQ ID NO: 30), and LanFP6 (SEQ ID NO: 31). The nucleic acid sequence of SEQ ID NO: 26, which encodes the LanFP2 fluorescent protein (SEQ ID NO: 2), was assembled from 1 EST (gi/66513208/gb/BW894938.1/BW894938 BW894938 Amphioxus *Branchiostoma floridae* unpublished cDNA library, cDNA clone bfne127p14). The assembled nucleic acid sequence of SEQ ID NO: 27, which encodes LanFP3 (SEQ ID NO: 3), was assembled from 12 ESTs (Table 4). LanFP4 (SEQ ID NO: 29) was assembled from 2 ESTs (Table 5) LanFP5 (SEQ ID NO: 30) was assembled from 13 ESTs (Table 6) and LanFP6 (SEQ ID NO: 31) was assembled from 19 ESTs (Table 7).

TABLE 4

ESTs For Assembly of LanFP3.

| EST | Position On Contig |
|---|---|
| gi_30921148_gb_B1386213.1_B1386213 | 70 –> 231 |
| gi_66412392_gb_BW804176.1_BW804176 | 47 –> 359 |
| gi_66412374_gb_BW804158.1_BW804158 | 47 –> 421 |
| gi_66481880_gb_BW867203.1_BW867203 | 49 –> 459 |
| gi_66416501_gb_BW808285.1_BW808285 | 73 –> 595 |
| gi_30919957_gb_BI384961.1_B1384961 | 33 –> 674 |
| gi_30917513_gb_B1382442.1_B1382442 | 0 > 721 |
| gi_30918384_gb_131383341.1_B1383341 | 450 –> 984 |
| gi_66434602_gb_BW826386.1_BW826386 | 216 <– 986 |
| gi_66556105_gb BW925317.1_BW925317 | 635 <– 986 |
| gi_66434576_gbBW826360.1_BW826360 | 232 <– 986 |
| gi_66438789_gb_BW830573.1_BW830573 | 328 <– 1000 |

TABLE 5

ESTs for assembly of LanFP4

| EST | Position On Contig |
|---|---|
| gi_30914617_gb_B1379468.1 | 1 <– 617 |
| gi_30922676_gb_B1387837.1 | 442 <– 1001 |

TABLE 6

ESTs for assembly of LanFP5

| EST | Position On Contig |
|---|---|
| gi_66459080_dbj_BW850864.1 | 1 <– 440 |
| gi_66452566_dbj_BW844350.1 | 3 <– 501 |
| gi_66453652_dbj_BW845436.1 | 3 <– 558 |
| gi_66328281_dbj_BW741633.1 | 1 <– 607 |
| gi_30922753_gb_BI387917.1 | 2 <– 658 |
| gi_30922844_gb_BI388023.1 | 11 <– 615 |
| gi 66323499_dbj_BW736869.1 | 9 <– 655 |
| gi_66325268_dbj_BW738638.1 | 3 <– 607 |
| gi_66322738_dbj_BW736108.1 | 3 <– 642 |
| gi_30920419_gb_BI385436.1 | 18 <– 666 |
| gi_66319319_dbj_BW732689.1 | 295 <– 944 |
| gi_30922999_gb_BI388191.1 | 451 <– 1038 |
| gi_30920521_gb_BI385546.1 | 451 <– 1091 |

TABLE 7

ESTs for assembly of LanFP6

| EST | Position On Contig |
|---|---|
| gi_66449929_dbj_BW841713.1 | 7 <– 540 |
| gi_66327445_dbj_BW740806.1 | 49 <– 599 |
| gi_66492735_dbj_BW878058.1 | 5 <– 595 |
| gi_66489993_dbj_BW875316.1 | 5 <– 588 |
| gi_66453275_dbj_BW845059.1 | 3 <– 547 |
| gi_66323701_dbj_BW737071.1 | 4 <– 599 |
| gi_66322827_dbj_BW736197.1 | 14 <– 596 |
| gi_66319309_dbj_BW732679.1 | 1 <– 599 |
| gi_66488533_dbj_BW873856.1 | 1 <– 599 |
| gi_66489207_dbj_BW874530.1 | 11 <– 547 |
| gi_66318082_dbj_BW731470.1 | 4 <– 635 |
| gi_66322601_dbj_BW735971.1 | 17 <– 602 |
| gi_66322698_dbj_BW736068.1 | 3 <– 632 |
| gi_66453535_dbj_BW845319.1 | 22 <– 607 |
| gi_66326163_dbj_BW739533.1 | 106 <– 713 |
| gi_66319274_dbj_BW732644.1 | 1 <– 670 |
| gi_66497089_dbj_BW882412.1 | 28 <– 670 |
| gi_66384032_dbj_BW781538.1 | 1 <– 787 |
| gi_66513453_dbj_BW895094.1 | 3 <– 834 |

Figure 12:
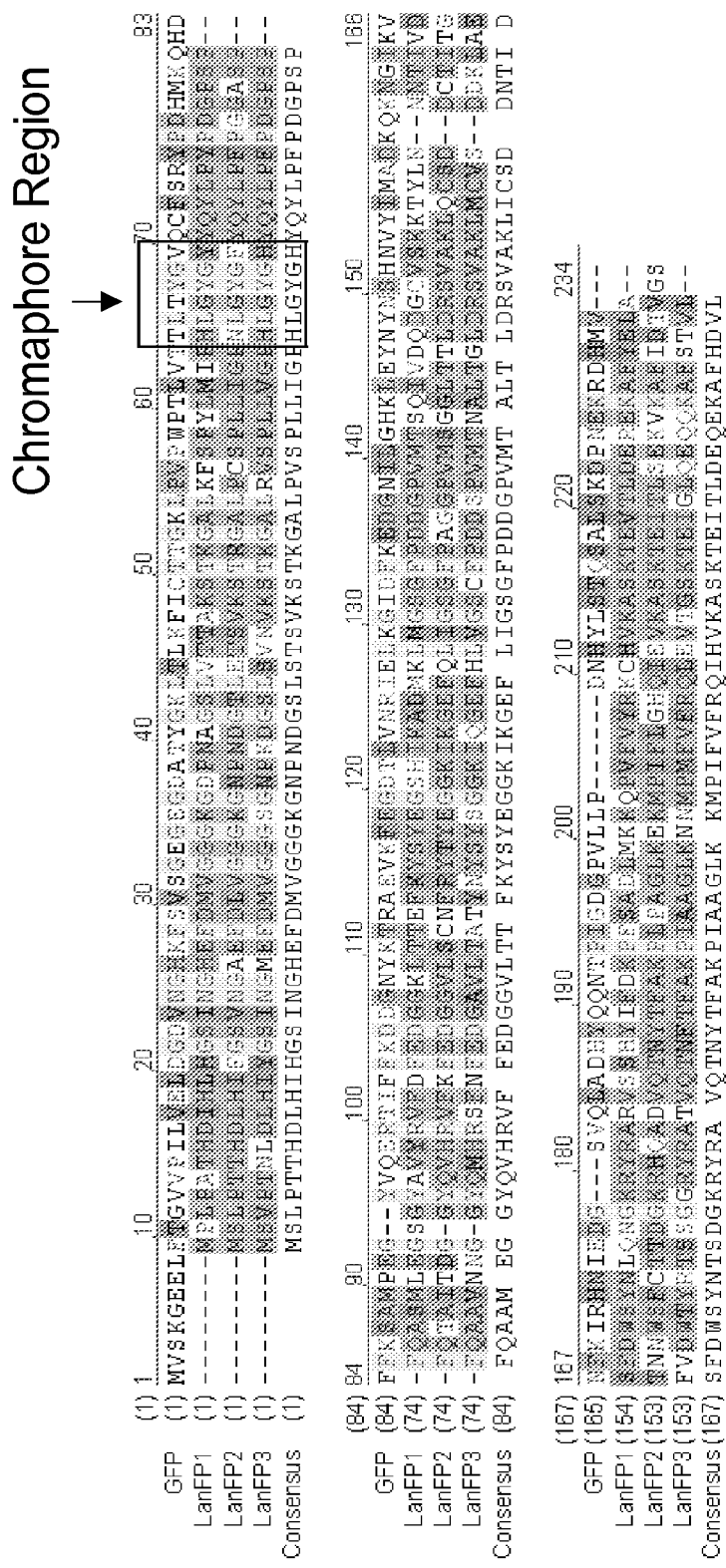
FIG. 12 aligns the protein sequences of humanized *Aequorea* GFP (EGFP Protein, SEQ ID NO: 28), LanFP1 (SEQ ID NO: 1), LanFP2 (SEQ ID NO: 2), and LanFP3 (SEQ ID NO: 3) and demonstrates that significant sequence divergence occurs between the LanFPs, The consensus of the sequences determined by shaded amino acids indicates that LanFPs share homology to the chromophore-forming region for *Aequorea* GFP (S65/T65, Y66, G67). Homology was determined using Align X protein alignment tool in the Vector NTI suite.
Figure 13A:
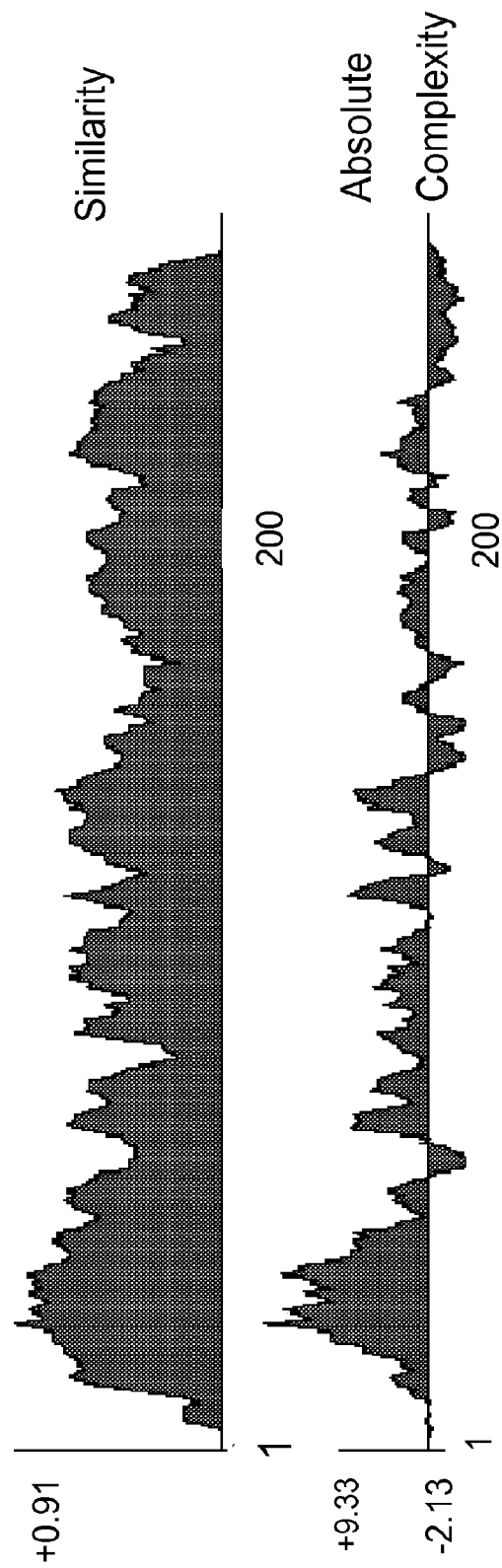
FIGS. 13A-B demonstrate the relationship between the muranized LanFP proteins. LanFP1 and LanFP2 are similar as indicated by FIG. 13A.
Figure 13B:
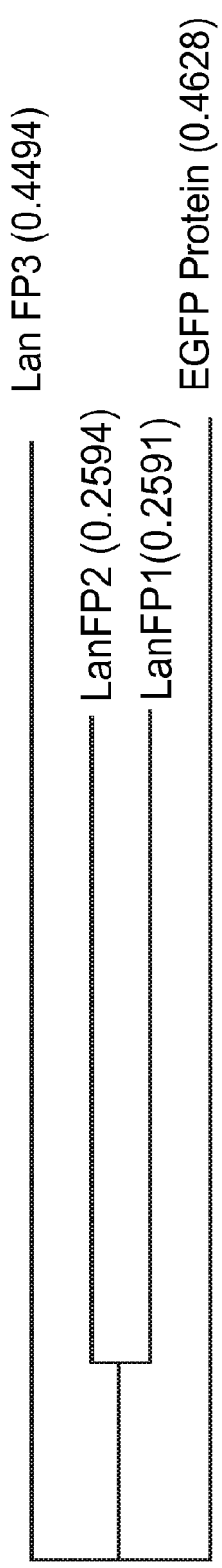
Figure 14:
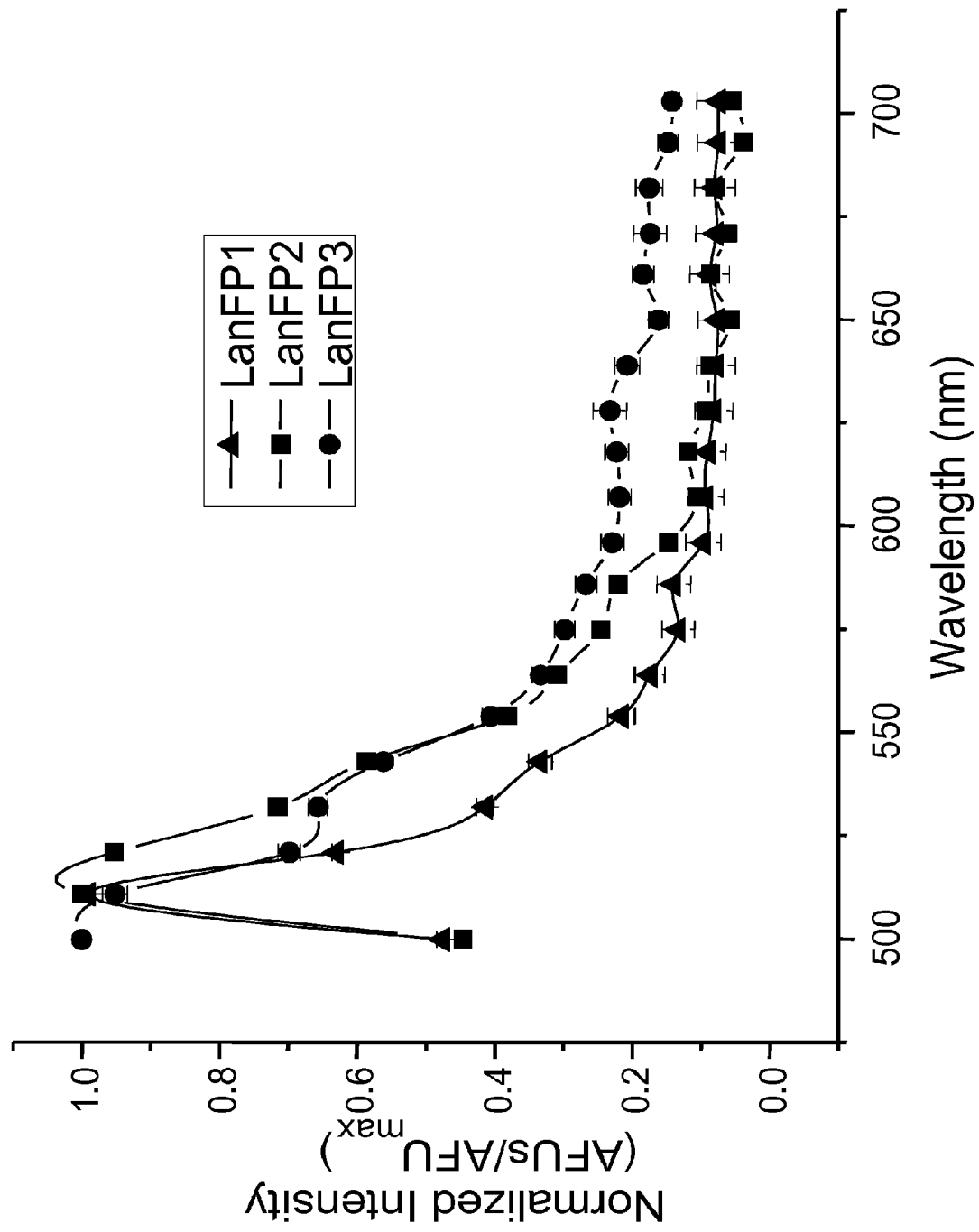
FIG. 14 provides the wavelength spectra for the muranized LanFPs. LanFP1 (triangle), LanFP2 (square), and LanFP3 (circle) demonstrate three distinct spectra. The three spectra are normalized to the maximum intensity for each protein. In general, LanFP1 was much brighter compared to LanFP2. LanFP2 and LanFP1 produced more light compared to LanFP3, These spectra were generated with 488 nm excitation on a LSM 510 META system using HEK-293 cells transiently transfected with LanFP plasmids.
Figure 15:
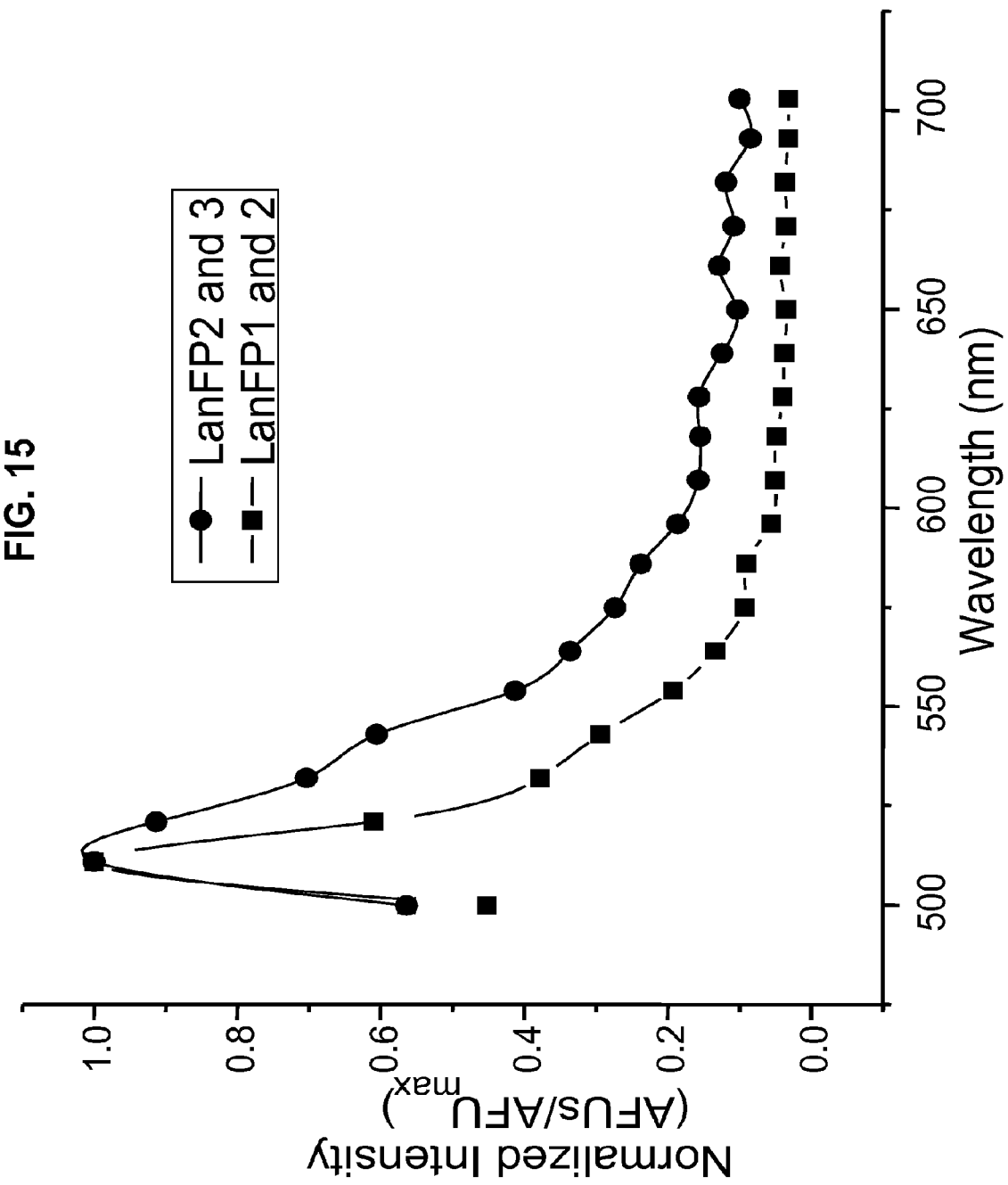
FIG. 15 graphically illustrates that LanFP1, LanFP2, and LanFP3 demonstrate comparative brightness, LanFP1 and LanFP2 (square) dominated over the cotransfected LanFP2 and LanFP3 (circle). These data do not discriminate the origin of the differential brightness. The spectra were generated with 488 nm excitation on a Zeiss LSM 510 META system using HEK-293 cells transiently transfected with plasmids containing LanFP.

While LanFP1, LanFP2, and LanFP3 are comparatively similar to each other and share a distant relation to EGFP (FIG. 13B), they demonstrate three distinct spectra (FIG. 14). The chromophore forming region of LanFP1, LanFP2, and LanFP3 remains homologous to that of wild type GFP (FIG. 12), suggestive of shared ancestry. LanFP1 and LanFP2 are most similar to each other (FIG. 13A). In general, LanFP1 is much brighter compared to LanFP2 and both produced more light compared to LanFP3. LanFP1, LanFP2, and LanFP3 demonstrate brightness in the aforementioned order. LanFP1 and LanFP2 dominate over the cotransfected LanFP2 and LanFP3 (FIG. 15).

Example 7

Identification of Endogenous Lancelet Fluorescent Proteins

Figure 16:
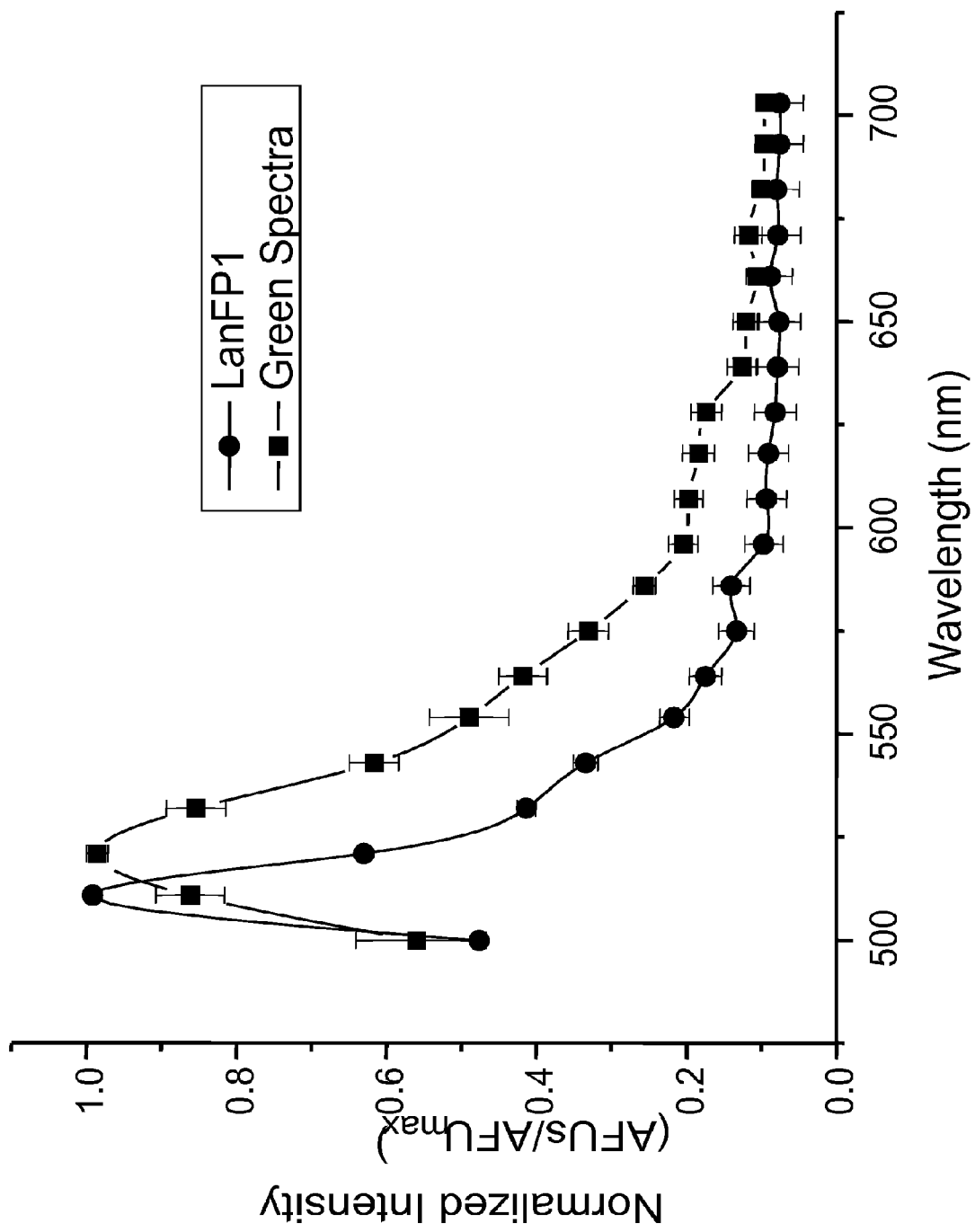
FIG. 16 shows that although muranized LanFP1 (circle) was very bright, it does not match the endogenous spectra from the Lancelet (square). The spectrum was generated with 488 nm excitation on a Zeiss LSM 510 META system using HEK-293 cells transiently transfected with a muranized LanFP 1 containing plasmid.
Figure 17:
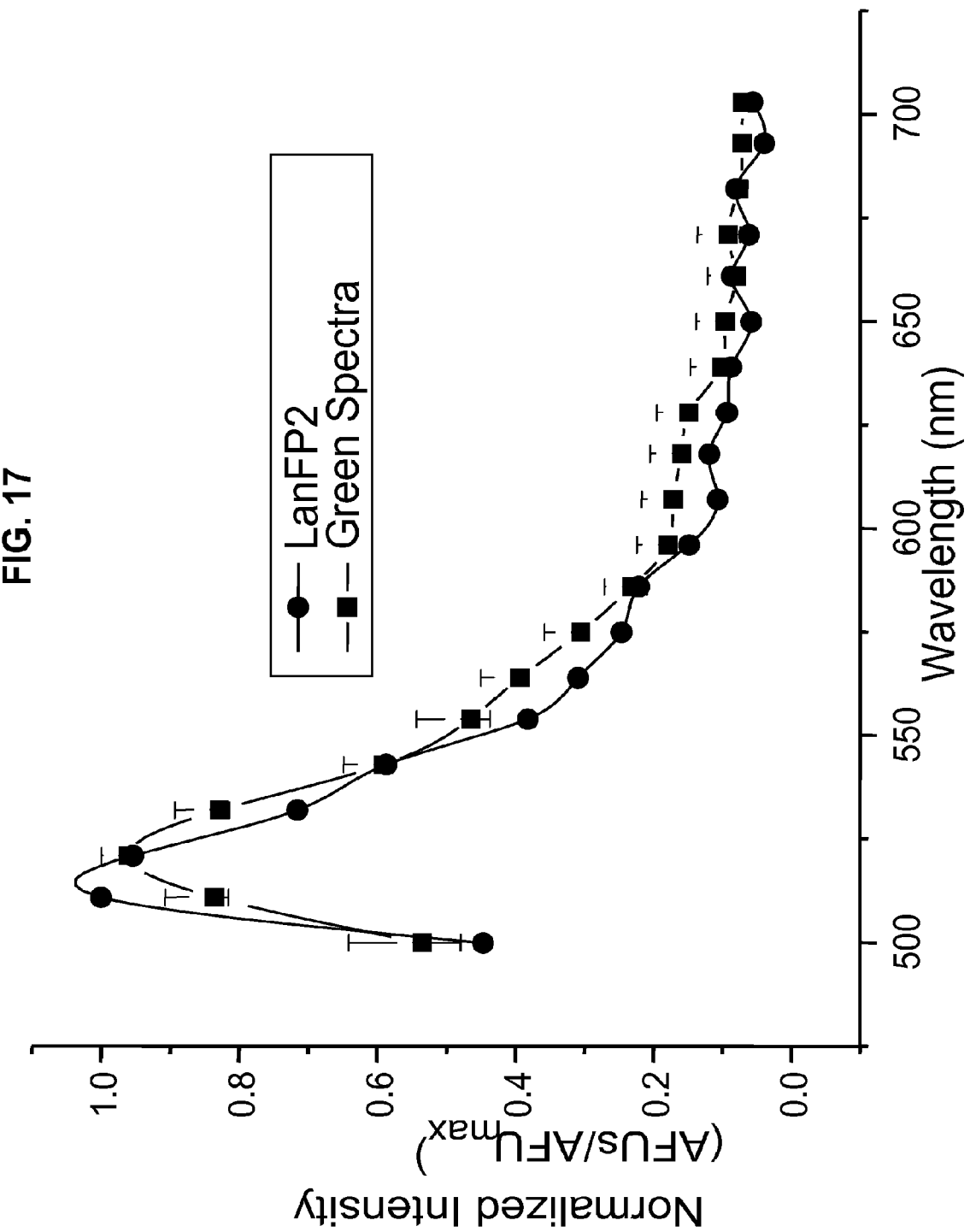
FIG. 17 shows that muranized LanFP2 (circle) was a strong spectral match to the endogenous green fluorescence signature from the Lancelet (square). The spectra were generated with 488 nm excitation on a Zeiss LSM 510 META system using HEK-293 cells transiently transfected with a muranized LanFP2 containing plasmid.

Upon examination of the lancelet under the microscope, the existence of an endogenous fluorescent protein was realized. The endogenous lancelet fluorescent protein cannot be directly attributed to those fluorescent proteins assembled in silico including SEQ ID NOs: 1-3 and 29-31. Although LanFP1 is very bright, it did not match the endogenous spectra from the lancelet (FIG. 16). LanFP2, however, had a similar spectral emission compared to the endogenous green fluorescence signature from the lancelet (FIG. 17).

Figure 18:
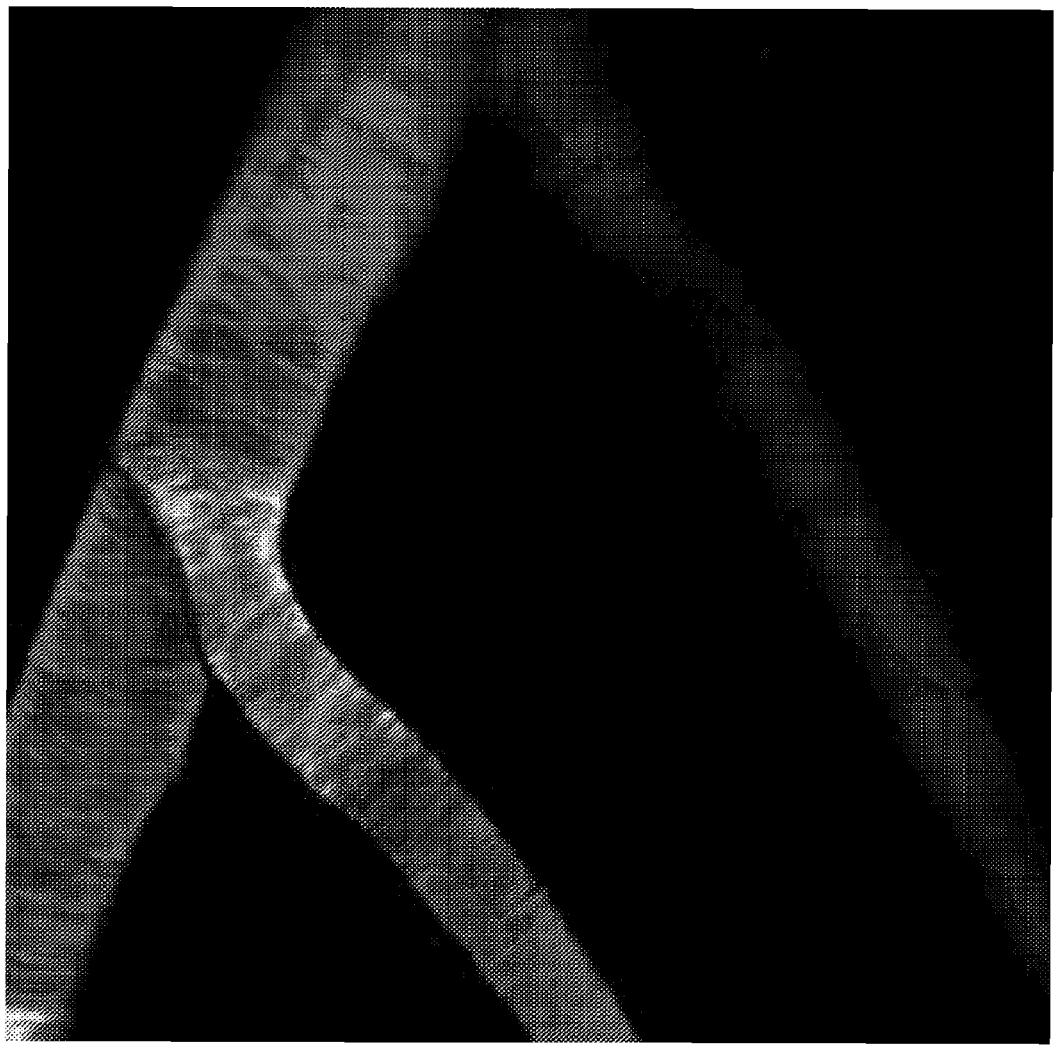
FIG. 18 reveals spectral imaging in a second red fluorescence in *Branchiostoma floridae*. The red fluorescence was localized between the lancelet filter organ and cirri. The red fluorescence cannot be directly attributed to the exogenous spectra from LanFP1, LanFP2, or LanFP3.
Figure 19:
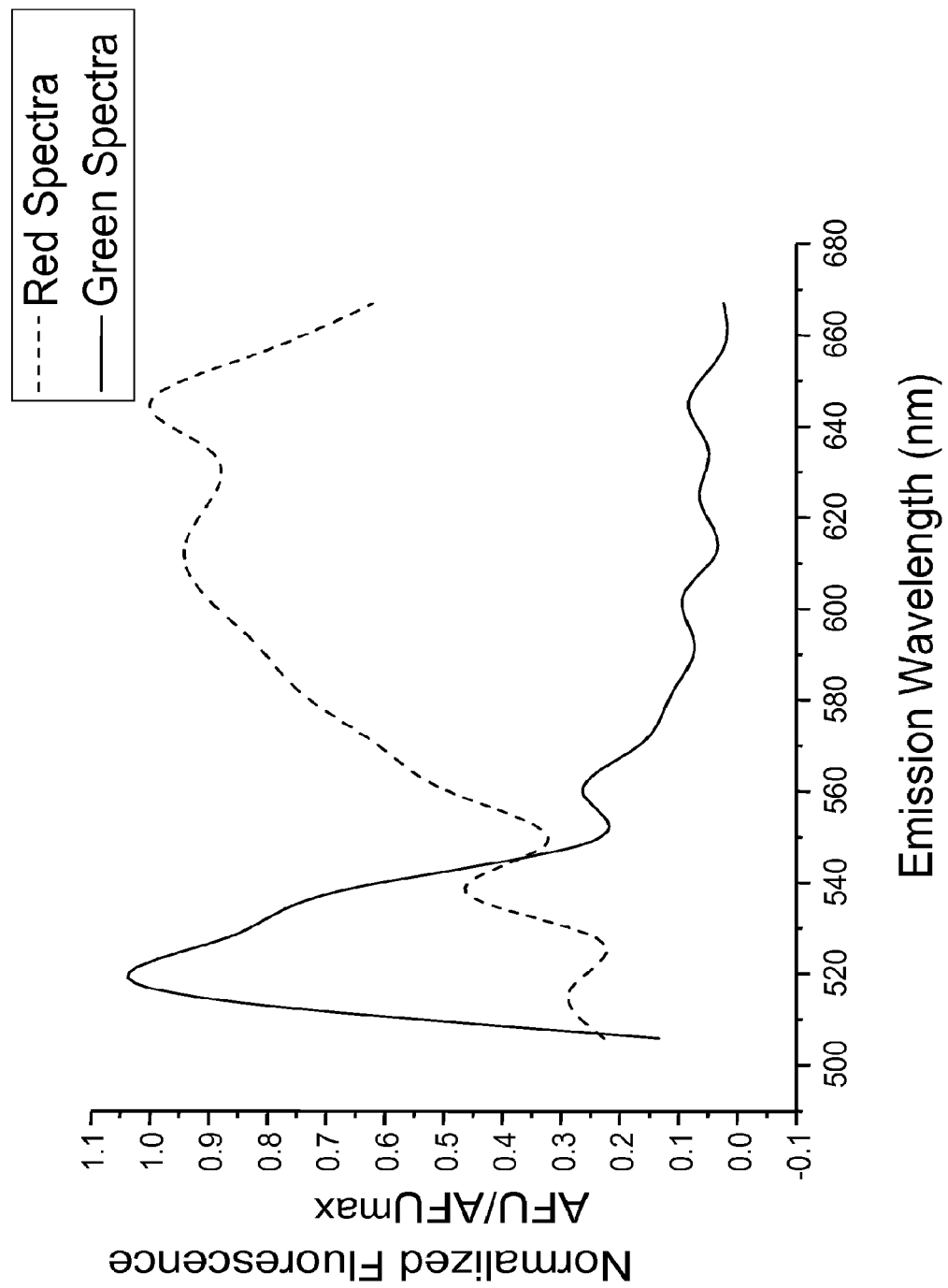
FIG. 19 graphically illustrates endogenous fluorescence exhibited by the lancelet. The red fluorescence (dashed line) demonstrated a wide spectrum compared to the green fluorescence (solid line). The resultant spectra were collected from spectral imaging of anesthetized lancelet. The emission was generated using 950 nm two-photon excitation.

Spectral imaging revealed a second red fluorescence in Branchiostoma floridae (FIG. 18). The red fluorescence is localized between the lancelet filter organ and cirri and cannot be directly attributed to the exogenous spectra from LanFP1, LanFP2, or LanFP3. The red fluorescence demonstrated a wide spectrum compared to the green fluorescence (FIG. 19).

Figure 20A:
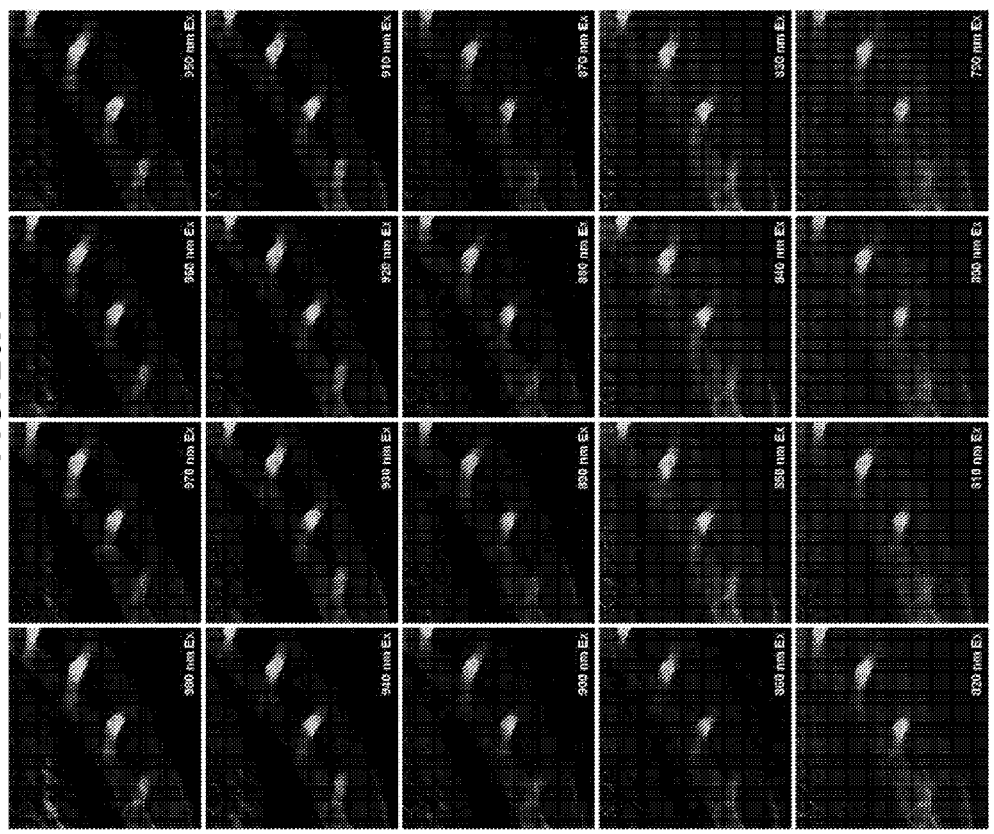
FIGS. 20A-D show that *Branchiostoma floridae* produced a second-harmonic generation (SHG) in definitive structures. The Two-photon excitation, ranging from 980 nm to 790 nm, was used to measure the changes in fluorescence protein excitation (FIG. 20A). Fluorescence was independent of excitation wavelength (FIG. 20B), while SHG was dependent on wavelength (FIG. 20C). *Branchiostoma floridae* fluorescence and SHG emission was simultaneously collected with spectral imaging using increasing two-photon excitation. Under these conditions a specific SHG that was exactly half the excitation wavelength was observed (FIG. 20D).
Figure 20B:
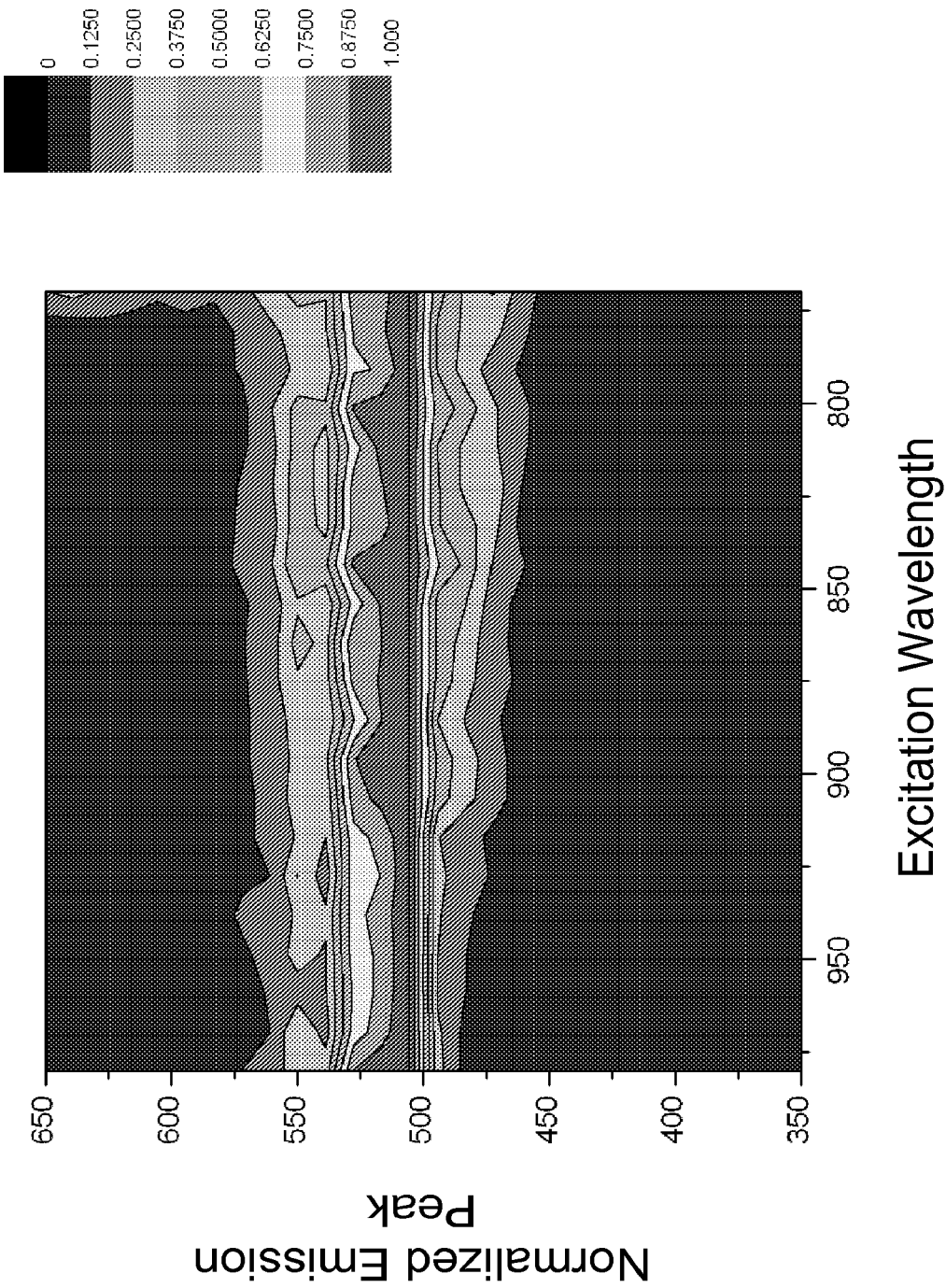
Figure 20C:
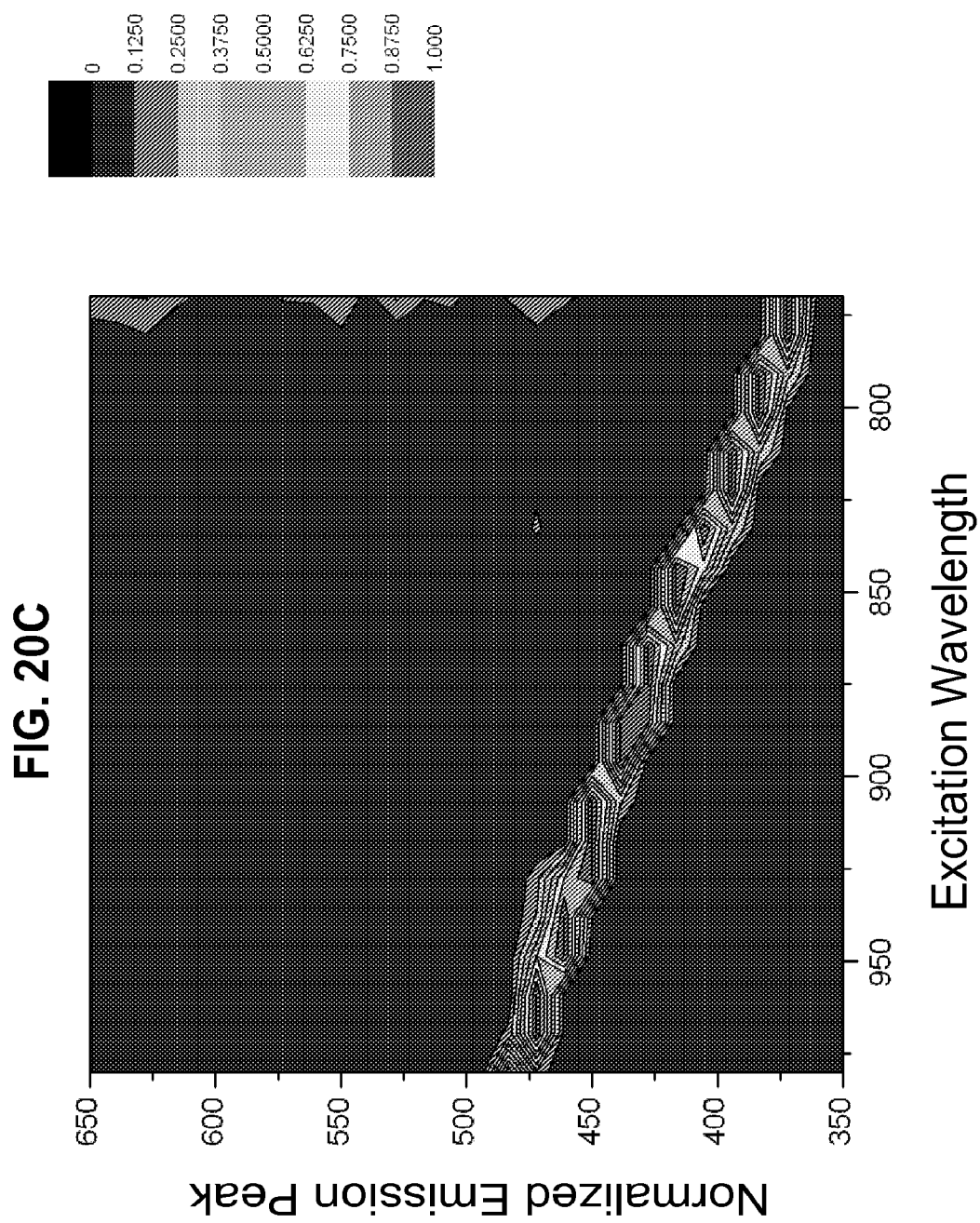
Figure 20D:
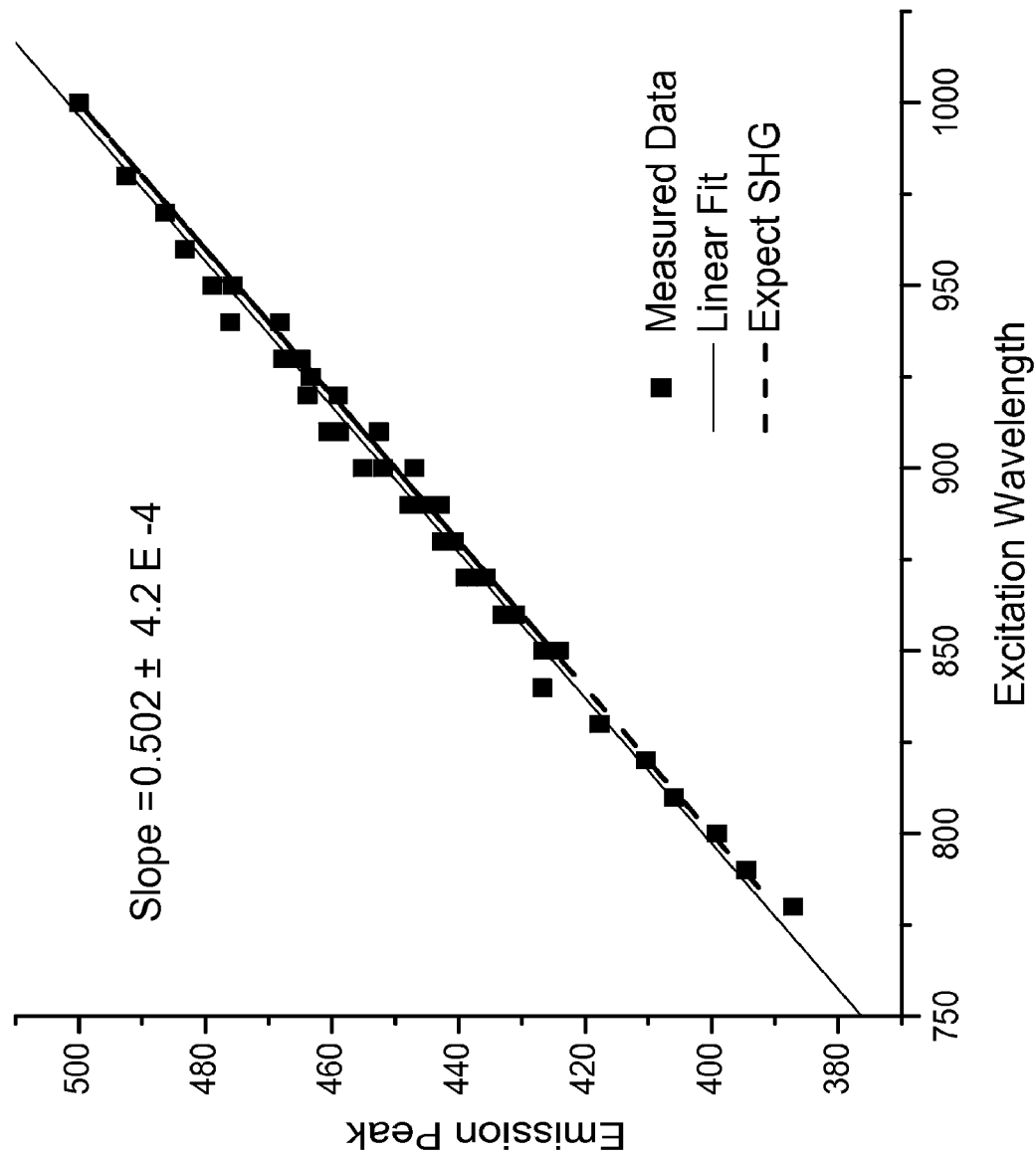
Figure 23:
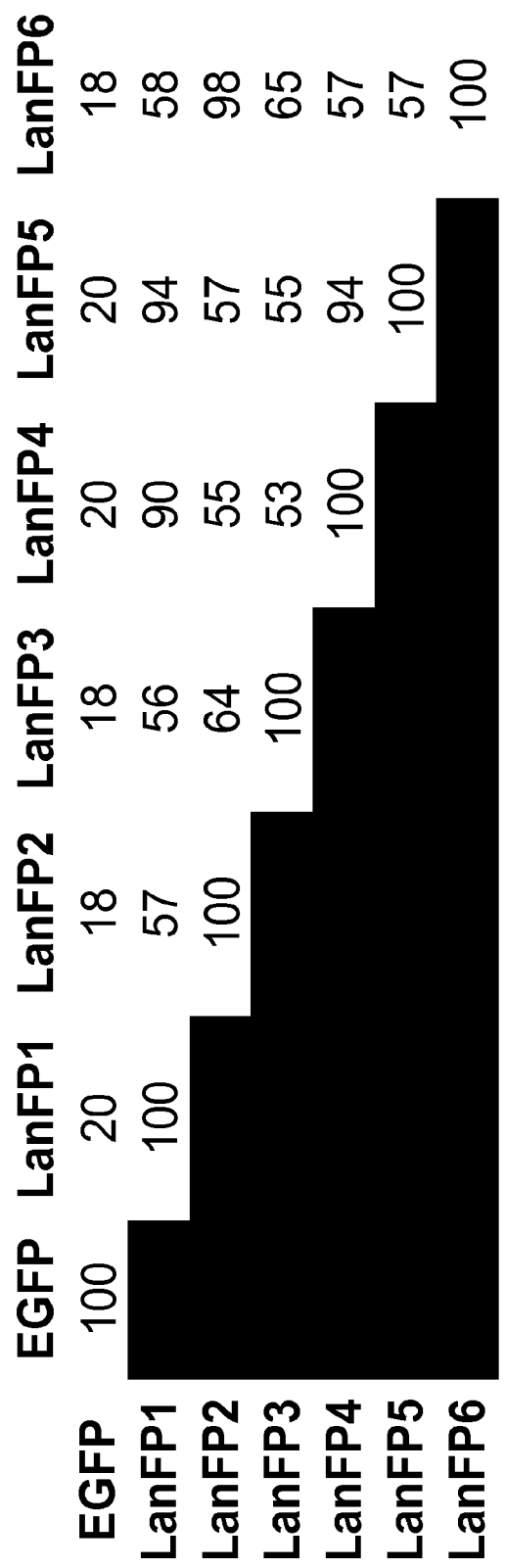
FIG. 23 shows the percentage of similarity between LanFP 1-6 to each other and to EGFP. As shown, the LanFP's are not very similar to EGFP.

Branchiostoma floridae was found to produce a second harmonic generation (SHG) in definitive structures. SGH is a nonlinear optical process, in which photons interacting with a nonlinear material are effectively combined to form new photons with twice the energy, and therefore twice the frequency and half the wavelength of the initial photons. Some molecules, such as collagen, are intrinsically second-harmonic-active in live cells. Two-photon excitation, ranging from 980 nm to 790 nm, was used to measure the changes in fluorescence protein excitation in anesthetized lancelet (FIG. 20A). Fluorescence was independent of excitation wavelength (FIG. 20B), while SHG was dependent on wavelength (FIG. 20C). Branchiostoma floridae fluorescence and SHG emission was simultaneously collected with spectral imaging using increasing two-photon excitation. Under these conditions a specific SHG that was exactly half the excitation wavelength was observed (FIG. 20D). These results are indicative of an intrinsic fluorescent molecule in the Lancelet that may or may not be attributable to an encoded fluorescent protein.

Example 8

LanFPs Exhibit Little Identity with Known Fluorescent Proteins

While the Branchiostoma fluorescent proteins of SEQ ID NO: 1, SEQ ID NO: 2, and SEQ ID NO: 3 (LanFPs) share identity between themselves, they exhibit very little identity with other known fluorescent proteins. The Branchiostoma fluorescent proteins share about 76% identity with each other at the amino acid level (FIG. 12). Compared to other known fluorescent proteins, LanFP1 (SEQ ID NO: 1) shares the highest identity with EGFP (SEQ ID NO: 4) of 29% at the nucleic acid level and only 19% identity at the amino acid level (FIG. 12). The distant identity between the LanFPs and other known fluorescent proteins (FIG. 21) indicates that the LanFPs belong to a distinct category of fluorescent proteins.

The identity of LanFPs with each other and other known fluorescent proteins was determined by aligning sequences using Vector NTI software with the following parameters: pairwise alignment with a gap opening penalty set at 10, gap extension penalty set at 0.1, gap penalty for helix core residue set at 4, gap penalty for core residue set at 4, gap penalty for structure termini set at 2, gap penalty for loop regions set at 1, number of residues inside helix to be treated as terminal set at 3, number of residues outside helix to be treated as terminal set at 0, number of residues inside strand to be treated as terminal set at 1, number of residue outside strand to treated as terminal set at 1.

Example 9

Expression of a LanFP1 in a Transgenic Animal Model

DNA Constructs

Figure 24:
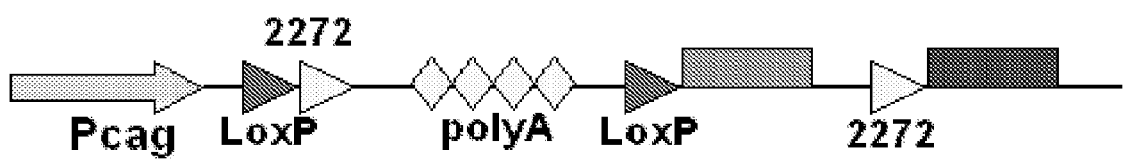
FIG. 24 shows the DNA construct used to generate transgenic mice expressing LanFP1. Pcag is the chicken actin promoter (light arrow). LoxP (dark triangles) and 2272 (lox2272, light triangles) indicate the two variants of the lox site used. The intervening poly A signal (diamonds) separates the lox sites prior to transformation. Rectangles represent the genes to be inserted into the animal genome upon transformation. The direction of the arrow and triangles indicates the orientation of the respective promoters and lox sites.

The DNA construct for transgenic mouse is generated using the chicken actin promoter to drive the expression of the fluorescent proteins. To produce tissue and cell type specific expression patterns using available Cre recombinase lines, a fragment of lox-stop-lox DNA is insert between the promoter and the fluorescent proteins (FIG. 24). Those of skill in the art will be familiar with the Cre-lox recombinase system, which is detailed in U.S. Pat. Nos. 4,959,317 and 6,890,726 and incorporated herein by reference.

Two lox sequences, loxP and lox2272, are used to create different recombination products by looping out the polyA stop signal through the loxP-loxP or lox2272-lox2272 sites. A total of four fluorescent proteins are used, including tdTomato, Venus, LanFP1 and Cerulean, on two separate DNA plasmids. Conventional molecular cloning techniques are used to produce these plasmids. Two plasmids are co-injected to produce co-integrated transgene lines.

Pronuclear Microinjection

DNA plasmid is linearized and purified for pronuclei injection by Stowers LASF facility. Methods of pronuclear microinjection are known in the art and patented under U.S. Pat. No. 4,873,191, which is incorporated herein by reference.

Superovulating donor female mice are produced by administering 0.1 ml PMS by intraperitoneal injection to female donor mice (C57BL/6 or FVB). Forty-seven hours after the PMS injection, 0.1 ml hCG is administered by intraperitoneal (IP) injection and the females are mated with stud males.

Twenty four hours after injection, female donors are sacrificed in groups of five or less, using cervical dislocation. Oviducts are collected and the egg/cumulus are flushed into a cell culture dish. Injection of DNA into the eggs is performed under a microscope using a micromanipulator. Injected eggs are incubated overnight prior to transfer into the females. The two-cell embryos are bilaterally transferred into the oviducts of a 0.5 day pregnant recipient. A total of 200 eggs are injected with the two DNA constructs for co-integration and ~80% of the cells are successfully transferred into the females.

Line Screening.

Figure 25:
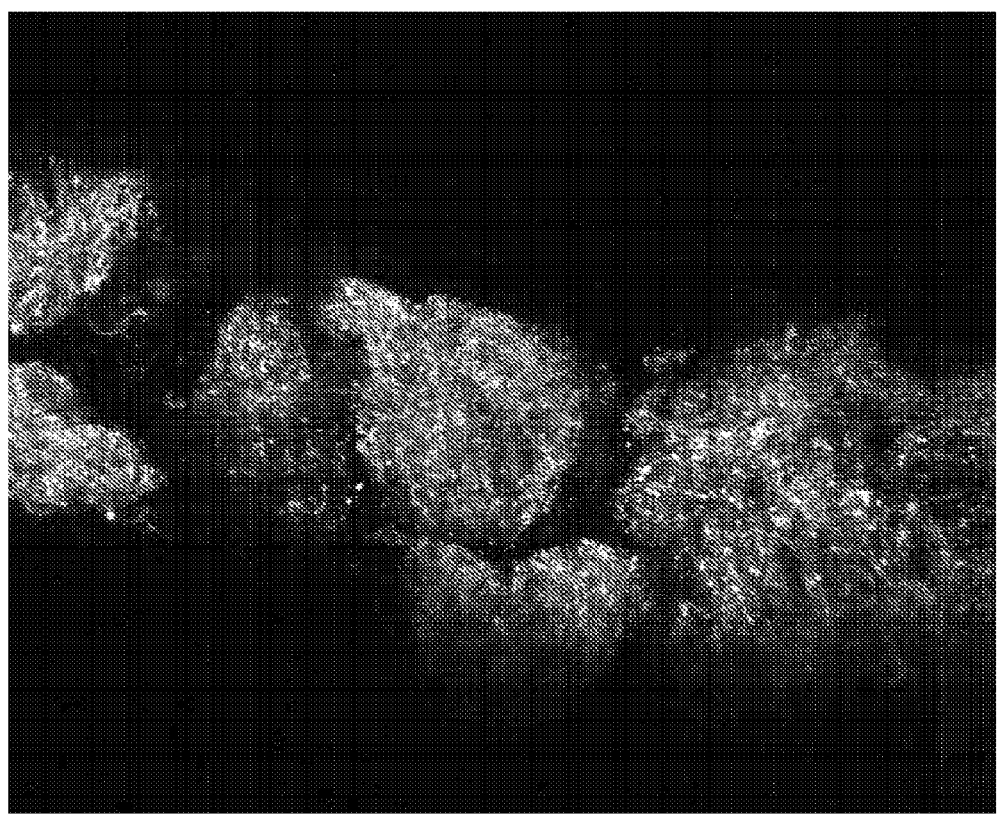
FIG. 25 shows the in vivo expression of LanFP fluorescence upon stimulation in the mitral cell dendrites in the brain forming glumeruli structure of a mouse transformed with LanFP1.

The resulting pups are born and tail DNA is genotyped for the presence of the transgene by polymerase chain reaction (PCR) using a standard protocol. Six founder lines were produced, and five of them are able to generate progenies carrying the transgene. One of the founder lines was mated to a transgenic Cre line to produce fluorescence in the mitral cells of the mouse olfactory bulb in the brain. Upon stimulation of the olfactory bulb, fluorescence is expressed in vivo in the mouse (FIG. 25). While the fluorescence is demonstrated in the olfactory bulb, the skilled artisan will recognize that a similar expression of fluorescence may be achieved upon stimulation of any other tissue or organ of the body as the LanFP will be inserted into the genome of the entire animal. Thus, other neurons, muscles, endothelial tissues, etc. may be caused to fluoresce if desired.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the claims.

REFERENCE LIST

The following references, to the extent that they provide exemplary procedural or other details supplementary to those set forth herein, are specifically incorporated herein by reference.

1. Altschul, S. F., et al., Nucleic Acids Res. 25(17): 3389-3402, Sep. 1, 1997
2. Altschul, S. F., et al., J. Mol. Biol. 215:403-10, 1990
3. Barany, Gene 37:111-23, 1985
4. Bidney et al., Plant Molec. Biol. 18:301, 1992
5. Braeckmans, K. et al., Biophysical Journal 85: 2240-2252, 2003
6. Braga, J. et al., Molecular Biology of the Cell 15: 4749-4760, 2004
7. Campagnola P. J. et al., J Biomed Opt. 6(3): 277-86, July 2001
8. Codon Usage Database provided by GenBank at http://www.kazusa.or.jp/codon1, released Nov. 25, 2005
9. Colicelli et al., Mol. Gen. Genet. 199:537-9, 1985
10. Current Protocols in Bioinformatics, (2005) 1.12.1-1.12.54
11. Current Protocols in Cell Biology, Unit 20, pub. John Wiley & Sons, Inc., 2004
12. Current Protocols in Cytometry, pub. John Wiley & Sons, Inc., 1997-2006
13. Current Protocols in Molecular Biology, pub. John Wiley & Sons, Inc., 1993
14. Current Protocols in Molecular Biology, pub. John Wiley & Sons, Inc., 1997
15. Current Protocols in Molecular Biology, Unit 6, pub. John Wiley & Sons, N.Y., 1989
16. Current Protocols in Molecular Biology, Unit 8, pub, John Wiley & Sons, Inc., 2000
17. Current Protocols in Protein Science, Unit 5, pub. John Wiley & Sons, Inc., 2002
18. Current Protocols in Protein Science, Unit 6, pub. John Wiley & Sons, Inc., 2002
19. Gordon, G. W. et al., Biophysical Journal 68: 766-778, 1995
20. Gorman et al., P.N.A.S. 79:6777, 1982
21. Grosschedl et al., Cell 41:885, 1985
22. Gustin et al., Biotechniques 14:22, 1993
23. Haraguchi, T., Cell Structure and Function 27: 333-334, 2002
24. Harvey, E. N. (1952). Bioluminescence. New York: Academic Press
25. Hastings, J. W. (1995). Bioluminescence. In: Cell Physiology (ed. by N. Speralakis) pp. 651-681. New York: Academic Press
26. Higgins, D. G. and Sharp, P. M., Fast and Sensitive multiple Sequence Alignments on a Microcomputer, CABIOS, 5: 151-153, 1989
27. Hogan, 1986. In: Manipulating The Mouse Embryo, Cold Spring Harbor Laboratory Press, Cold Spring Harbor, N.Y.
28. Hooykas-Van Slogteren et al., Nature 311:763-764, 1984
29. International Patent Application WO 00/02997, publication date Jan. 20, 2000
30. International Patent Application WO 00/03246, publication date Jan. 20, 2000
31. International Patent Application WO 00/17624, publication date Mar. 30, 2000
32. International Patent Application WO 00/17643, publication date Mar. 30, 2000
33. International Patent Application WO 00/26408, publication date May 11, 2000

34. International Patent Application WO 90/04036, publication date Apr. 19, 1990
35. International Patent Application WO 90/10077, publication date Sep. 7, 1990
36. International Patent Application WO 92/02190, publication date Feb. 20, 1992
37. International Patent Application WO 95/21191, publication date Aug. 10, 1995
38. International Patent Application WO 96/23810, publication date Aug. 8, 1996
39. International Patent Application WO 97/26333, publication date Jul. 24, 1997
40. International Patent Application WO 97/28261, publication date Aug. 7, 1997
41. International Patent Application WO 97/41228, publication date Nov. 6, 1997
42. International Patent Application WO 98/02571, publication date Jan. 22, 1998
43. Jost, et al., J. B. C. 269:26267-73, 1994
44. Kabat et al., Sequences of Proteins of Immunological Interest, N.I.H. publication no. 91-3242, 1991.
45. Klee et al., Ann. Rev. Plant Phys, 38:467-486, 1987
46. Kluczyk et al., Peptides 21:1411-1420, 2000
47. Kroon et al., 2000, Eur. 3. Biochem. 267: 6740-6752
48. Labas, Y. A. et al., PNAS 99(7) 4256-4261, Apr. 2, 2002
49. Li, S., et al., J Biol. Chem. 272(45): 28545-28549, 1997
50. Liu et al., P.N.A.S. 84:3439, 1987
51. Murphy, M. E. and Sies, H. (1990)
52. Nagai, T. et al., Nature Biotechnology 20(1): 87-90, January, 2002
53. Ogawa, H., et al., Proc. Natl. Acad. Sci. 92: 11899-11903, 1995
54. Okayama et al., Mal. Cell. Bio. 3:280, 1983
55. Oruro, M. et al., Science 273: 1392-1395, 1996
56. Plant Biochemistry and Molecular Biology (eds Lea & Leegood, John Wiley & Sons) (1993) pp 275-295
57. Rose et al., 1990, Methods in Yeast Genetics, Cold Spring Harbor Laboratory Press, Cold Spring Harbor, N.Y.
58. Sambrook et al., 1989, Molecular Cloning, A Laboratory Manual, Cold Spring Harbor Laboratory Press, Cold Spring Harbor, N.Y.
59. Shahla et al., Plant Molec. Biol. 8:291, 1987
60. Shao et al., Bioconjug. Chem. 11: 822-826, 2000
61. U.S. Patent Application No. 0050272111, filed Jul. 6, 2005
62. U.S. Patent Application No. 005968750A, filed Oct. 9, 1998
63. U.S. patent application Ser. No. 08/597,274, filed Feb. 6, 1996
64. U.S. patent application Ser. No. 08/757,046, filed Nov. 25, 1996
65. U.S. patent application Ser. No. 08/990,103, filed Dec. 12, 1997
66. U.S. Patent Application No. 2004/0138420, filed Jul. 15, 2004
67. U.S. Patent Application No. 2004/0138420A1, filed: Jan. 14, 2005
68. U.S. Patent Application No. 2005/0014223, filed Jan. 20, 2005
69. U.S. Patent Application No. 2005/0014223A1, filed: Apr. 1, 2004
70. U.S. Patent Application No. 2005/0272111A1, filed Dec. 8, 2005
71. U.S. Pat. No. 4,683,195, filed Jul. 28, 1987
72. U.S. Pat. No. 4,683,202, filed Jul. 28, 1987
73. U.S. Pat. No. 4,736,866, filed Jun. 22, 1984
74. U.S. Pat. No. 4,870,009, filed Dec. 15, 1983
75. U.S. Pat. No. 4,873,191, filed Aug. 18, 1986
76. U.S. Pat. No. 4,940,838, filed Feb. 23, 1984
77. U.S. Pat. No. 5,258,498, filed Nov. 2, 1993
78. U.S. Pat. No. 5,439,797, filed Aug. 8, 1995
79. U.S. Pat. No. 5,484,956, filed Jan. 16, 1996
80. U.S. Pat. No. 5,538,879, filed Jul. 23, 1996
81. U.S. Pat. No. 5,576,198, filed Nov. 19, 1996
82. U.S. Pat. No. 5,584,807, filed Jan. 20, 1995
83. U.S. Pat. No. 5,595,896, filed Jan. 21, 1997
84. U.S. Pat. No. 5,625,048, filed Apr. 29, 1997
85. U.S. Pat. No. 5,629,470, filed May 13, 1997
86. U.S. Pat. No. 5,633,155, filed May 27, 1997
87. U.S. Pat. No. 5,650,135, filed Jul. 22, 1997
88. U.S. Pat. No. 5,656,466, filed Aug. 12, 1997
89. U.S. Pat. No. 5,674,731, filed Oct. 7, 1997
90. U.S. Pat. No. 5,688,648, filed Nov. 18, 1997
91. U.S. Pat. No. 5,689,045, filed Nov. 18, 1997
92. U.S. Pat. No. 5,689,049, filed Nov. 18, 1997
93. U.S. Pat. No. 5,707,804, filed Jan. 13, 1998
94. U.S. Pat. No. 5,728,528, filed Mar. 17, 1998
95. U.S. Pat. No. 5,739,409, filed Apr. 14, 1998
96. U.S. Pat. No. 5,750,870, filed May 12, 1998
97. U.S. Pat. No. 5,767,367, filed Jun. 16, 1998
98. U.S. Pat. No. 5,804,387, filed Sep. 8, 1998
99. U.S. Pat. No. 5,824,485, filed Oct. 20, 1998
100. U.S. Pat. No. 5,863,727, filed Jan. 26, 1999
101. U.S. Pat. No. 5,866,336, filed Feb. 2, 1999
102. U.S. Pat. No. 5,869,255, filed Feb. 9, 1999
103. U.S. Pat. No. 5,874,304, filed Feb. 23, 1999
104. U.S. Pat. No. 5,876,995, filed Mar. 2, 1999
105. U.S. Pat. No. 5,911,952, filed Jun. 15, 1999
106. U.S. Pat. No. 5,945,283, filed Aug. 31, 1999
107. U.S. Pat. No. 5,945,526, filed Aug. 31, 1999
108. U.S. Pat. No. 5,968,738, filed Oct. 19, 1999
109. U.S. Pat. No. 5,968,750, filed Oct. 19, 1999
110. U.S. Pat. No. 5,981,200, filed Nov. 9, 1999
111. U.S. Pat. No. 5,989,835, filed Nov. 23, 1999
112. U.S. Pat. No. 5,998,146, filed Dec. 7, 1999
113. U.S. Pat. No. 6,008,373, filed Dec. 28, 1999
114. U.S. Pat. No. 6,020,192, filed Feb. 1, 2000
115. U.S. Pat. No. 6,113,886, filed Sep. 5, 2000
116. U.S. Pat. No. 6,152,358, filed Nov. 28, 2000
117. U.S. Pat. No. 6,458,547, filed Oct. 1, 2002
118. U.S. Pat. No. 6,936,428, filed Aug. 30, 2005
119. U.S. Pat. No. 6,969,597, filed Nov. 29, 2005
120. U.S. Patent No. 60/261,448, filed Jan. 12, 2001
121. Wilmut, et al., Nature 385: 810-813, 1997
122. Wilson, T. and Hastings, J. W. (1998). Bioluminescence. Annu Rev Cell Dev Biol 14, 197-230
123. Xu et al., Proc. Natl. Acad. Sci. U.S.A. 96: 151-156, 1999
124. Yang, T., et al., Nucleic Acids Research 24(22): 4592-4593
125. Yildiz, A. and Selvin, P. R. Ace. Chem. Res. 38 (7), 574-582, 2005

What is claimed:

1. A method of making an isolated *Branchiostoma* fluorescent protein, comprising
   (i) transfecting a cell with a nucleic acid sequence at least about 90% identical to a polynucleotide selected from the group consisting of SEQ ID NOs: 22-27, 37, and their respective complementary sequences;
   (ii) cultivating the cell expressing the fluorescent protein; and
   (iii) isolating the fluorescent protein.

2. The method according to claim 1, wherein the nucleic acid sequence is at least about 95% identical to a polynucleotide selected from the group consisting of SEQ ID NOs: 22-27, 37, and their respective complementary sequences.

3. The method according to claim 1, wherein the nucleic acid sequence is selected from the group consisting of SEQ ID NOs: 22-27, 37, and their respective complementary sequences.

4. The method according to claim 1, wherein the nucleic acid sequence is SEQ ID NO: 22.

5. The method according to claim 1, wherein the nucleic acid sequence is SEQ ID NO: 23.

6. The method according to claim 1, wherein the nucleic acid sequence is SEQ ID NO: 24.

7. The method according to claim 1, wherein the nucleic acid sequence is SEQ ID NO: 25.

8. The method according to claim 1, wherein the nucleic acid sequence is SEQ ID NO: 26.

9. The method according to claim 1, wherein the nucleic acid sequence is SEQ ID NO: 27.

10. The method according to claim 1, wherein the nucleic acid sequence is SEQ ID NO: 37.

* * * * *